(12) United States Patent
Kim et al.

(10) Patent No.: US 10,844,136 B2
(45) Date of Patent: Nov. 24, 2020

(54) METHOD FOR POSITIONING, IN CYTOPLASM, ANTIBODY HAVING COMPLETE IMMUNOGLOBULIN FORM BY PENETRATING ANTIBODY THROUGH CELL MEMBRANE, AND USE FOR SAME

(71) Applicant: ORUM THERAPEUTICS INC., Daejeon (KR)

(72) Inventors: Yong-Sung Kim, Gyeonggi-do (KR); Dong-Ki Choi, Gyeonggi-do (KR); Seung-Min Shin, Seoul (KR); Sung-Hoon Kim, Seoul (KR)

(73) Assignee: ORUM THERAPEUTICS INC., Daejeon (KR)

( * ) Notice: Subject to any disclaimer, the term of this patent is extended or adjusted under 35 U.S.C. 154(b) by 37 days.

(21) Appl. No.: 15/327,369

(22) PCT Filed: Jul. 22, 2015

(86) PCT No.: PCT/KR2015/007626
§ 371 (c)(1),
(2) Date: Jan. 18, 2017

(87) PCT Pub. No.: WO2016/013870
PCT Pub. Date: Jan. 28, 2016

(65) Prior Publication Data
US 2017/0218084 A1    Aug. 3, 2017

(30) Foreign Application Priority Data
Jul. 22, 2014    (KR) .................. 10-2014-0092673
Jul. 21, 2015    (KR) .................. 10-2015-0103163

(51) Int. Cl.
| | | |
|---|---|---|
| A61K 39/00 | (2006.01) | |
| C07K 16/32 | (2006.01) | |
| C07K 16/40 | (2006.01) | |
| C07K 16/28 | (2006.01) | |
| C07K 16/00 | (2006.01) | |
| C07K 16/46 | (2006.01) | |
| C07K 16/30 | (2006.01) | |
| G01N 33/574 | (2006.01) | |

(52) U.S. Cl.
CPC .............. *C07K 16/32* (2013.01); *C07K 16/00* (2013.01); *C07K 16/2863* (2013.01); *C07K 16/30* (2013.01); *C07K 16/40* (2013.01); *C07K 16/46* (2013.01); *G01N 33/574* (2013.01); *A61K 2039/505* (2013.01); *C07K 2317/24* (2013.01); *C07K 2317/515* (2013.01); *C07K 2317/56* (2013.01); *C07K 2317/565* (2013.01); *C07K 2317/569* (2013.01); *C07K 2317/73* (2013.01); *C07K 2317/77* (2013.01); *C07K 2317/82* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | |
|---|---|---|
| 9,815,866 B2 | 11/2017 | Shiba et al. |
| 2005/0288492 A1 | 12/2005 | Rabbitts et al. |
| 2011/0189206 A1 | 8/2011 | Barbas |
| 2011/0263829 A1 | 10/2011 | Kim et al. |
| 2013/0266570 A1 | 10/2013 | Weisbart et al. |
| 2014/0179543 A1 | 6/2014 | Rabbitts et al. |
| 2015/0246945 A1 | 9/2015 | Shiba et al. |
| 2016/0229892 A1 | 8/2016 | Hazlehurst et al. |
| 2017/0158777 A1 | 6/2017 | Kim et al. |
| 2019/0144566 A1 | 5/2019 | Kim et al. |
| 2019/0231872 A1 | 8/2019 | Kwon et al. |
| 2019/0389910 A1 | 12/2019 | Kim et al. |

FOREIGN PATENT DOCUMENTS

| | | |
|---|---|---|
| CN | 1241574 A | 1/2000 |
| CN | 101402675 A | 4/2009 |
| CN | 102209726 A | 10/2011 |
| CN | 103874710 A | 6/2014 |
| JE | H 8-511162 A | 11/1996 |
| JP | 2006521088 A | 9/2006 |
| JP | 2006523086 A | 10/2006 |
| JP | 2011519370 A | 7/2011 |
| KR | 1020090008290 A | 1/2009 |
| KR | 10-2010-0045683 | 5/2010 |
| KR | 10-2010-0053466 A | 5/2010 |
| KR | 10-2016-0011598 A | 2/2016 |
| KR | 10-1790669 B1 | 10/2017 |
| KR | 10-2019-0056340 A | 5/2019 |
| WO | WO 2003077945 A1 | 9/2003 |

(Continued)

OTHER PUBLICATIONS

Marchisio et al. (Exp. Cell Res. Sep. 1984; 154 (1): 112-24).*
Garrigues et al. (Am. J. Pathol. Feb. 1993; 142 (2): 607-22).*
Sapra et al. (Cancer Res. Dec. 15, 2002; 62 (24): 7190-4).*
Yamaguchi et al. (Biochem. Biophys. Res. Commun. Nov. 1, 2014; 454 (4): 600-603).*
Stuible et al. (J. Biol. Chem. Mar. 7, 2014; 289 (10): 6498-512).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*

(Continued)

*Primary Examiner* — Stephen L Rawlings
(74) *Attorney, Agent, or Firm* — Jones Day

(57) ABSTRACT

A method is described of localizing an intact immunoglobulin-format antibody in cytosol by permeating the cell membrane, thereby avoiding the necessity to use a special external protein delivery system. The method achieves high effects on the treatment and diagnosis of tumor and disease-related factors that show structurally complex interactions through a wide and flat surface between protein and protein.

12 Claims, 23 Drawing Sheets
(20 of 23 Drawing Sheet(s) Filed in Color)
Specification includes a Sequence Listing.

(56) References Cited

FOREIGN PATENT DOCUMENTS

| WO | WO 2004046186 A2 | 6/2004 |
| --- | --- | --- |
| WO | WO 2004046186 A3 | 6/2004 |
| WO | WO 2004046188 A2 | 6/2004 |
| WO | WO 2004046188 A3 | 6/2004 |
| WO | WO 2007133835 A2 | 11/2007 |
| WO | WO 2007133835 A3 | 11/2007 |
| WO | 2009-134025 | 11/2009 |
| WO | 2009134027 A2 | 11/2009 |
| WO | 2010-056043 | 5/2010 |
| WO | WO 2011026641 A1 | 3/2011 |
| WO | WO 2011026641 A9 | 3/2011 |
| WO | WO 2011140151 A1 | 11/2011 |
| WO | WO 2012135831 A1 | 10/2012 |
| WO | WO 2014042209 A1 | 3/2014 |
| WO | WO 2016013871 A1 | 1/2016 |
| WO | WO 2016161390 A1 | 10/2016 |
| WO | WO 2017204606 A1 | 11/2017 |

OTHER PUBLICATIONS

Caldas et al. (Mol. Immunol. May 2003; 39 (15): 941-952).*
Winkler et al. (J. Immunol. Oct. 15, 2000; 165 (8): 4505-4514).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Choi et al. (MAbs. 2014; 6 (6): 1402-14).*
Avrameas, A., et al., "Polyreactive Anti-DNA Monoclonal Antibodies and a Derived Peptide as Vectors for the Intracytoplasmic and Intranuclear Translocation of Macromolecules", "PNAS, Proceedings of the National Academy of Sciences", May 1998, pp. 5601-5606, vol. 95.
Baek, D.S., et al., "Construction of a Large Synthetic Human Fab Antibody Library on Yeast Cell Surface by Optimized Yeast Mating", "Journal of Microbiology and Biotechnology", Jan. 7, 2014, pp. 408-420, vol. 24, No. 3.
Blundell, T.L., et al., "Structural Biology and Bioinformatics in Drug Design: Opportunities and Challenges for Target Identification and Lead Discovery", "Philosophical Transactions of the Royal Society B", Feb. 3, 2006, pp. 413-423, vol. 361.
Cabantous, S., et al., "Protein Tagging and Detection with Engineered Self-Assembling Fragments of Green Fluorescent Protein", "Nature Biotechnology", Dec. 5, 2004, pp. 102-107, vol. 23, No. 1.
Chauhan, A., et al., "The Taming of the Cell Penetrating Domain of the HIV Tat: Myths and Realities", "Journal of Controlled Release", Nov. 17, 2006, pp. 148-162, vol. 117.
Ehrenstein, M.R., et al., "Human IgG Anti-DNA Antibodies Deposit in Kidneys and Induce Proteinuria in SCID Mice", "Kidney International", May 1, 1995, pp. 705-711, vol. 48.
Falnes, P.O., et al., "Ability of the Tat Basic Domain and VP22 to Mediate Cell Binding, but Not Membrane Translocation of the Diphtheria Toxin A-Fragment", "Biochemistry", Jan. 3, 2001, pp. 4349-4358, vol. 40.
Gerber, H.P., et al., "The Antibody-Drug Conjugate: an Enabling Modality for Natural Product-Based Cancer Therapeutics", "The Royal Society of Chemistry 2013", Mar. 25, 2013, pp. DOI: 10.1039/c3np20113a, Publisher: RSC Publishing.
Horth, M., et al., "Theoretical and Functional Analysis of the SIV Fusion Peptide", "The EMBO Journal", May 27, 1991, pp. 2747-2755, vol. 10, No. 10.
Imai, K., et al., "Comparing Antibody and Small-Molecule Therapies for Cancer", "Nature Reviews", Sep. 2006, pp. 714-727, vol. 6.
Jenssen, H., et al., "Peptide Antimicrobial Agents", "Clinical Microbiology Reviews", Jul. 2006, pp. 491-511, vol. 19, No. 3.

Kabat, E.A., et al., "Sequences of Proteins of Immunological Interest", 1991, pp. 1-24, vol. 1.
Kim, A., et al., "Interfering Transbody-Mediated Her2 Gene Silencing Induces Apoptosis by G0/G1 Cell Cycle Arrest in Her2-overexpressing SK-BR-3 Breast Cancer Cells", "Biotechnology and Bioprocess Engineering", Dec. 12, 2011, pp. 413-419, vol. 17.
Kim, S.J., et al., "Antibody Engineering for the Development of Therapeutic Antibodies", "Molecules and Cells", Aug. 18, 2005, pp. 17-29, vol. 20, No. 1.
Kim, Y-R, et al., "Heavy and Light Chain Variable Single Domains of an Anti-DNA Binding Antibody Hydrolyze Both Double- and Single-Stranded DNAs Without Sequence Specificity", "The Journal of Biological Chemistry", Jun. 2, 2006, pp. 15287-15295, vol. 281, No. 22.
Koivunen, E., et al., "Phage Libraries Displaying Cyclic Peptides with Different Ring Sizes: Ligand Specificities of the RGD-Directed Integrins", "Nature Biotechnology", Mar. 1995, pp. 265-270, vol. 13.
Lee, J., et al., "Functional Consequences of Complementarity-determining Region Deactivation in a Multifunctional Anti-nucleic Acid Antibody", "The Journal of Biological Chemistry", Dec. 13, 2013, pp. 35877-35885, vol. 288, No. 50.
Lee, W-R, et al. "Gene Silencing by Cell-Penetrating, Sequence-Selective and Nucleic-Acid Hydrolyzing Antibodies", "Nucleic Acids Research", Dec. 9, 2009, pp. 1596-1609, vol. 38, No. 5.
Lin, C. et al., "Effect of Chemical Functionalities in Poly(Amido Amine)s for Non-viral Gene Transfection", "Journal of Controlled Release", Jul. 3, 2008, pp. 267-272, vol. 132.
Madaio, M.P., et al., "Spontaneously Produced Anti-DNA/DNase I Autoantibodies Modulate Nuclear Apoptosis in Living Cells", "European Journal of Immunology", Sep. 24, 2006, pp. 3035-3041, vol. 26.
Magdelaine-Beuzelin, C., et al., "Structure-function Relationships of the Variable Domains of Monoclonal Antibodies Approved for Cancer Treatment", "Critical Reviews in Oncology/Hematology", Apr. 20, 2007, pp. 210-225, vol. 64.
Manikandan, J., et al., "Protein i: Interference at Protein Level by Intrabodies", "Fronteirs in Bioscience", Jan. 1, 2007, pp. 1344-1352, vol. 12.
Nakajima, O., et al., "Method for Delivering Radiolabeled Single-Chain Fv Antibody to the Brain", "Journal of Health Science", Jan. 5, 2004, pp. 159-163, vol. 50, No. 2.
Patel, L.N., et al., "Cell Penetrating Peptides: Intracellular Pathways and Pharmaceutical Perspectives", "Pharmaceutical Research", Apr. 19, 2007, pp. 1977-1992, vol. 24, No. 11.
Scheffzek, K., et al., "The Ras-RasGAP Complex: Structural Basis for GTPase Activation and Its Loss in Oncogenic Ras Mutants", "Science Magazine", Jul. 18, 1997, pp. 333-338, vol. 277.
Tanaka, T., et al., "Tumour Prevention by a Single Antibody Domain Targeting the Interaction of Signal Transduction Proteins with RAS", "The EMBO Journal", Jun. 14, 2007, pp. 3250-3259, vol. 26.
Weisbart, R.H., et al., "A Cell-Penetrating Bispecific Antibody for Therapeutic Regulation of Intracellular Targets", "Molecular Cancer Therapeutics", Oct. 2012, pp. 2169-2173, vol. 11, No. 10.
Zack, D.J., et al., "Mechanisms of Cellular Penetration and Nuclear Localization of an Anti-Double Strand DNA Autoantibody", "The Journal of Immunology", Jun. 18, 1996, pp. 2082-2088, vol. 157.
Note: For the non-patent literature citations that no month of publication is indicated, the year of publication is more than 1 year prior to the effective filing date of the present application.
J.Y. Jang et al., "A nucleic acid-hydrolyzing antibody penetrates into cells via caveolae-mediated endocytosis, localizes in the cytosol and exhibits cytotoxicity", Cellular and Molecular Life Sciences, vol. 66, No. 11-12, Apr. 14, 2009, pp. 1985-1997.
D. Choi et al., "A general strategy for generating intact, full-length IgG antibodies that penetrate into the cytosol of living cells", MABS, vol. 6, No. 6, Nov. 2, 2014, pp. 1402-1414.
EPO, the extended European Search Report of EP 15825418.5 dated Jan. 4, 2018.
Barrette-NG, I., et al., "The structure of the SBP-Tag-streptavidin complex reveals a novel helical scaffold bridging binding pockets on seperate subunits", "Acta Cryst.", 2013, pp. 879-887, vol. D69, Publisher: International Union of Crystallography.

(56) References Cited

OTHER PUBLICATIONS

Cao, L., et al., "Enhancement of antitumor properties of TRAIL by targeted delivery to the tumor neovasculature", "Mol Cancer Ther", Apr. 2008, vol. 7, No. 4, Publisher: The American Association for Cancer Research.

Hu, S., et al., "Comparison of the Inhibition Mechanisms of Adalimumab and Infliximab in Treating Tumor Necrosis Factor-Associated Diseases from a Molecular View", "The Journal of Biological Chemistry", Sep. 20, 2013, pp. 27059-27067, vol. 288, No. 38, Publisher: The American Society for Biochemistry and Molecular Biology, Inc.

Madaio, M., et al., "Spontaneously produced anti-DNA/DNase I autoantibodies modulate nuclear apoptosis in living cells", "Eur. J. Immunol.", 1996, pp. 3035-3041, vol. 26, Publisher: VCH Verlagsgesellschaft mbH.

Vargas-Madrazo, E., et al., "An improved model of association for VH-VL immunoglobulin domains: Asymmetries between VH and VL in the packing of some interface residues", "Journal of Molecular Recognition", 2003, pp. 113-120, vol. 16, Publisher: John Wiley & Sons, Ltd.

Al-Lazikani et al., 1997, "Standard conformations for the canonical structures of immunoglobulins," J Mol Biol, 273(4):927-948.

Altmann et al., 2017, "Identification of a Novel ITGαvβ6-Binding Peptide Using Protein Separation and Phage Display," Clin Cancer Res., 23(15):4170-4180.

Baek et al., 2014, "DNA Assembly Tools and Strategies for the Generation of Plasmids," Microbiol Spectr, 2(5), pp. 1-12.

Baek et al., 2015, "Humanization of a phosphothreonine peptide-specific chicken antibody by combinatorial library optimization of the phosphoepitope-binding motif," Biochem Biophys Res Commun., 463(3):414-420.

Barbas et al., 2007, "Quantitation of DNA and RNA," Cold Spring Harb. Protoc., retreived from internet: http://cshprotocols.cshlp.org/content/2007/11/pdb.ip47.long on Nov. 1, 2019 (2 pages).

Benatuil et al., 2010, "An improved yeast transformation method for the generation of very large human antibody libraries," Protein Eng Des Sel., 23(4):155-159.

Bissig et al., 2013, "Lipid sorting and multivesicular endosome biogenesis," Cold Spring Harb Perspect Biol., 5(10):a016816.

Bonvin et al., 2015, "De novo isolation of antibodies with pH-dependent binding properties," Mabs, 7(2):294-302.

Chen et al., 1995, "Enhancement and destruction of antibody function by somatic mutation: unequal occurrence is controlled by V gene combinatorial associations," EMBO J., 14(12):2784-2794.

Colman, 1994, "Effects of amino acid sequence changes on antibody-antigen interactions," Res Immunol., 145(1):33-36.

Cross et al., 2001, "Mechanisms of Cell Entry by Influenza Virus," Expert Review in Molecular Medicine, Aug. 2001, pp. 1-18.

Devanaboyina et al., 2013, "The effect of pH dependence of antibody-antigen interactions on subcellular trafficking dynamics," Mabs, 5(6):851-859.

Di Paolo et al., 2003, "A recombinant immunotoxin derived from a humanized epithelial cell adhesion molecule-specific single-chain antibody fragment has potent and selective antitumor activity," Clin Cancer Res, 9(7):2837-2848.

Di Russo et al., 2012, "pH-Dependent conformational changes in proteins and their effect on experimental pK(a)s: the case of Nitrophorin 4," PLoS Comput Biol., 8(11):e1002761.

Dohi et al., 2001, "Elimination of colonic patches with lymphotoxin receptor-Ig prevents Th2 cell-type colitis," The Journal of Immunology, 167(5):2781-2790.

Du et al., 2011, "pK(a) coupling at the intein active site: implications for the coordination mechanism of protein splicing with a conserved aspartate," J Am Chem Soc., 133(26):10275-10282.

Dudgeon et al., 2012, "General strategy for the generation of human antibody variable domains with increased aggregation resistance," Proc Natl Acad Sci USA, 109(27):10879-10884.

Edman, 1959, "Chemistry of amino acids and peptides," Annu Rev Biochem, 28:69-96.

Ewert et al., 2004, "Stability improvement of antibodies for extracellular and intracellular applications: CDR grafting to stable frameworks and structure-based framework engineering," Methods, 34(2):184-199.

Fernandes et al., 2016, "Context-dependent roles for lymphotoxin-β receptor signaling in cancer development," Biochim Biophys Acta., 1865(2):204-219.

Gingis-Velitski et al., 2004, "Heparanase uptake is mediated by cell membrane heparan sulfate proteoglycans," J Biol Chem., 279(42):44084-44092.

Gouttefangeas et al., 2014, "Flow Cytometry in Cancer Immunotherapy: Applications, Quality Assurance, and Future," N. Rezaei (ed.), Cancer Immunology: A Translational Medicine Context, Springer-Verlag Berlin Heidelberg, Chapter 25, pp. 471-490.

Guglielmi et al., 2011, "Selection for intrabody solubility in mammalian cells using GFP fusions," Protein Eng Des Sel., 24(12):873-881.

Guidotti et al., 2017, "Cell-Penetrating Peptides: From Basic Research to Clinics," Trends in Pharmacological Sciences, 38(4):406-424.

Guillard et al., 2015, "Engineering therapeutic proteins for cell entry: the natural approach," Trends in biotechnology, 33(3):163-171.

Herce et al., 2009, "Arginine-rich peptides destabilize the plasma membrane, consistent with a pore formation translocation mechanism of cell-penetrating peptides," Biophys J., 97(7):1917-1925.

Holig et al., 2004, "Novel RGD lipopeptides for the targeting of liposomes to integrin-expressing endothelial and melanoma cells," Prot Eng Des Sel, 17(5):433-441.

Hollingshead, 2008, "Antitumor efficacy testing in rodents," J Natl Cancer Inst., 100(21):1500-1510.

Horton et al., 2002, "Exploring privileged structures: the combinatorial synthesis of cyclic peptides," J Comput Aided Mol Des., 16(5-6):415-430.

International Search Report and Written Opinion dated Oct. 11, 2019 of International Patent Application No. PCT/IB2019/055193 (14 pages).

International Search Report and Written Opinion dated Oct. 7, 2015 of International Patent Application No. PCT/KR2015/007626 (published as WO 2016013870) (12 pages).

International Search Report and Written Opinion dated Sep. 29, 2017 of International Patent Application No. PCT/KR2017/005559 (published as WO 2017204606) (10 pages).

International Search Report and Written Opinion dated Sep. 30, 2015 of International Patent Application No. PCT/KR2015/007627 (published as WO 2016013871) (12 pages.).

Kamide et al., 2010, "Isolation of novel cell-penetrating peptides from a random peptide library using in vitro virus and their modifications," Int J Mol Med., 25(1):41-51.

Kim et al., 2015, "Quantitative assessment of cellular uptake and cytosolic access of antibody in living cells by an enhanced split GFP complementation assay," Biochem Biophys Res Commun., 467(4):771-777.

Kim et al., 2016, "Endosomal acidic pH-induced conformational changes of a cytosol-penetrating antibody mediate endosomal escape," J Control Release, 235:165-175.

Kim, 2014, "General Strategy for Generating Intact, full-lenght IgG antibodies that penetrate into the cytosol of living cells," KSBB, IP306, Oct. 5, 2014, XP002776743, retreived from the internet: URL:www.ksbb.or.kr/board/download.php?code=notice&num=1913 &comm= [retrieved on Dec. 11, 2017].

Korte et al., 1992, "ph-dependent hydrophobicity profile of hemagglutinin of influenza virus and its possible relevance in virus fusion," Biosci Rep., 12(5):397-406.

Kussie et al., 1994, "A single engineered amino acid substitution changes antibody fine specificity," J Immunol., 152(1):146-152.

Lee et al., 2011, "Generation of bivalent and bispecific kringle single domains by loop grafting as potent agonists against death receptors 4 and 5," J Mol Biol., 411(1):201-219.

Leem et al., 2016, "ABodyBuilder: Automated antibody structure prediction with data-driven accuracy estimation," MAbs, 8(7):1259-1268.

(56) References Cited

OTHER PUBLICATIONS

Leshchiner et al., 2015, "Direct inhibition of oncogenic KRAS by hydrocarbon-stapled SOS1 helices," Proc Natl Acad Sci USA, 112(6):1761-1766.
Li et al., 2014, "pH-Controlled two-step uncoating of influenza virus," Biophys J., 106(7):1447-1456.
Lonn et al. 2016, "Enhancing Endosomal Escape for Intracellular Delivery of Macromolecular Biologic Therapeutics," Sci Rep., 6:32301.
Marschall et al., 2011, "Targeting antibodies to the cytoplasm," MAbs, 3(1):3-16.
Mauri et al., 1998, "Light, a new member of the TNF superfamily, and lymphotoxin alpha are ligands," Immunity, 8(1):21-30.
Morita et al., 2011, "Lipid recognition propensities of amino acids in membrane proteins from atomic resolution data," BMC Biophys., 4:21 (12 pages).
Munyendo et al., 2012, "Cell penetrating peptides in the delivery of biopharmaceuticals," Biomolecules, 2(2):187-202.
Munz et al., 2009, "The emerging role of EpCAM in cancer and stem cell signaling," Cancer Res., 69(14):5627-5629.
NCBI, 2016, "Chain H, Heavy Chain of Fab Fragment Variable Region of Antibody D5," PDB: 3JAU_H, NCBI database, Feb. 10, 2016.
Patgiri et al., 2011, "An orthosteric inhibitor of the Ras-Sos interaction," Nat Chem Biol, 7(9):585-587.
Perchiacca et al., 2011, "Mutational analysis of domain antibodies reveals aggregation hotspots within and near the complementarity determining regions," Proteins, 79(9):2637-2647.
Perrimon et al., 2000, "Specificities of heparan sulphate proteoglycans in developmental processes," Nature, 404(6779):725-728.
Pimenta et al., 2014, "Role of tertiary lymphoid structures (TLS) in antitumor immunity. Potential tumor-induced cytokines/chemokines that regulate TLS formation in epithelial-derived cancers," Cancer, 6(2):969-997.
Qin et al., 1999, "Functional implications of structural differences between variants A and B of bovine beta-lactoglobulin," Protein Sci., 8(1):75-83.
Quadir et al., 2014, "PEG-polypeptide block copolymers as pH-responsive endosome-solubilizing drug nanocarriers," Mol Pharm., 11(7):2420-2430.
Rezai et al., 2006, "Testing the conformational hypothesis of passive membrane permeability using synthetic cyclic peptide diastereomers," J Am Chem Soc., 128(8):2510-2511.
Shin et al., 2017, "Antibody targeting intracellular oncogenic Ras mutants exerts anti-tumour effects after systemic administration," Nat Commun., 8:15090 (14 pages).
Simon et al., 2013, "Epithelial cell adhesion molecule-targeted drug delivery for cancer therapy, Expert opinion on drug delivery," Expert Opin Drug Deliv., 10(4):451-468.
Singh et al., 2016, "A New Triglycyl Peptide Linker for Antibody-Drug Conjugates (ADCs) with Improved Targeted Killing of Cancer Cells," Mol Cancer Ther., 15(6):1311-1320.
Sudhamsu et al., 2013, "Dimerization of LTβR by LTα1β2 is necessary and sufficient for signal transduction," Proc Natl Acad Sci USA, 110(49):19896-19901.
Supplemental European Search Report and Written Opinion of European Patent Application No. 15825508.3 dated Feb. 8, 2018.
Tanaka et al., 2003, "Intrabodies based on intracellular capture frameworks that bind the RAS protein with high affinity and impair oncogenic transformation," EMBO J., 22(5):1025-1035.
Tanaka et al., 2003, "Single domain intracellular antibodies: a minimal fragment for direct in vivo selection of antigen-specific intrabodies," J Mol Biol., 331(5):1109-1120.
Teicher, 2009, "In vivo/ex vivo and in situ assays used in cancer research: a brief review," Toxicol Pathol, 37(1):114-122.
Wang et al., 2001, "The regulation of T cell homeostasis and autoimmunity by T cell-derived Light," J Clin Invest, 108(12):1771-1780.
Weinstein, 2015, "Lymphotoxin Therapeutic Lymphoid Organogenesis in the Tumor Microenvironment," Adv Cancer Res., 128:197-233.
Went et al., 2006, "Frequent high-level expression of the immunotherapeutic target Ep-CAM in colon, stomach, prostate and lung cancers," Br J Cancer, 94(1):128-135.
Xiong et al., 2002, "Crystal structure of the extracellular segment of integrin alpha Vbeta3 in complex with an Arg-Gly-Asp ligand," Science, 296(5565):151-155.
Claro et al., 2017, "Chapter 4—Design and applications of cyclic peptides" in Peptide Applications in Biomedicine, Biotechnology and Bioengineering, Woodhead Publishing Series in Biomaterials, Nov. 27, 2017, pp. 87-129.
Kim et al., 2009, "Generation of Humanized anti-DNA Hydrolyzing Catalytic Antibodies by Complementarity Determining Region Grafting," Biochem Biophys Res Commun., 379(2):314-318 (Epub 2008).
Min et al., 2016, "Cell-free production and streamlined assay of cytosol-penetrating antibodies," Biotechnol Bioeng, 113(10):2107-2112.
Paul, 1993, "Fundamental immunology—Third Edition," New York: Raven Press, pp. 292-295.
Williams et al., 2018, "Peptide ligands for targeting the extracellular domain of EGFR: Comparison between linear and cyclic peptides," Chem Biol Drug Des., 91(2):605-619.

* cited by examiner

Fig. 2A

```
                                            CDR1                             CDR2
                      10          20     abcdef  30            40           50
m3D8 VL(Vκ8)   DLVMTQSPSSLAVSAGEKVTMSC [KSSQSLFNSRTRKNYLA] WYQQKPGQSPKLLIY [WASTRES]
hT0 VL(Vκ3)    DIVLTQSPATLSLSPGERATLSC [KSSQSLFNSRTRKNYLA] WYQQKPGQAPRLLIY [WASTRES]
hT2 VL(Vκ3)    DIVMTQSPATLSLSPGERATLSC [KSSQSLFNSRTRKNYLA] WYQQKPGQAPRLLIY [WASTRES]
hT3 VL(Vκ1)    DIVMTQSPSSLSASVGDRVTITC [KSSQSLFNSRTRKNYLA] WYQQKPGKAPKLLIY [WASTRES]

CDR3
                      60          70         80         90          100
m3D8 VL(Vκ8)   GVPDRFTGSGSGTDFTLTISSVQAEDLAVYYC [KQSYYHMYT] FGSGTKLEIKR
hT0 VL(Vκ3)    GIPDRFSGSGSGTDFTLTISSLEPEDFAVYYC [KQSYYHMYT] FGQGTKVEIKR
hT2 VL(Vκ3)    GIPDRFSGSGSGTDFTLTISSLEPEDFAVYYC [KQSYYHMYT] FGQGTKVEIKR
hT3 VL(Vκ1)    GVPSRFSGSGSGTDFTLTISSLQPEDFATYYC [KQSYYHMYT] FGQGTKVEIKR
```

Fig. 2B

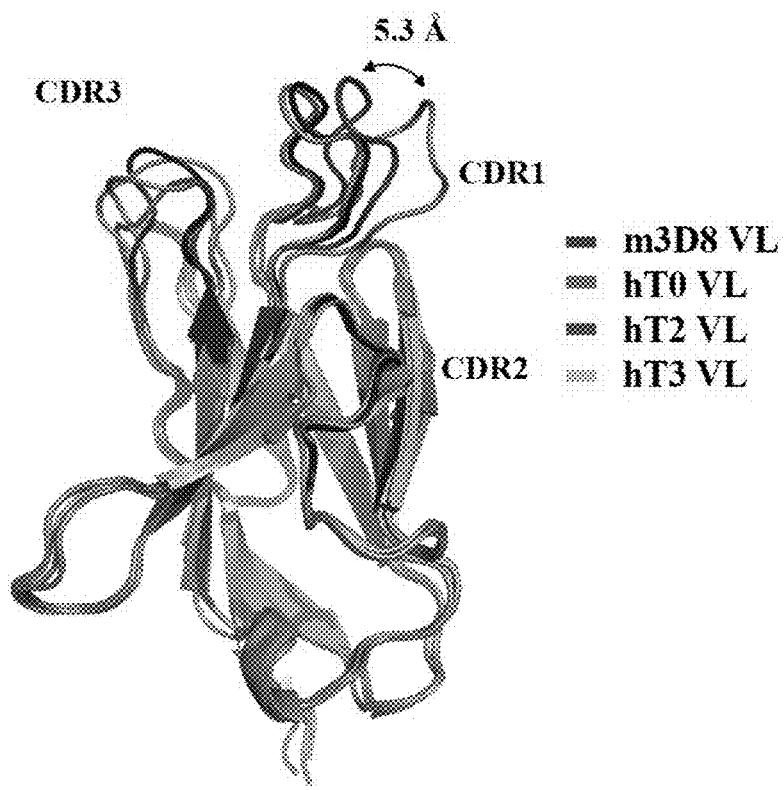

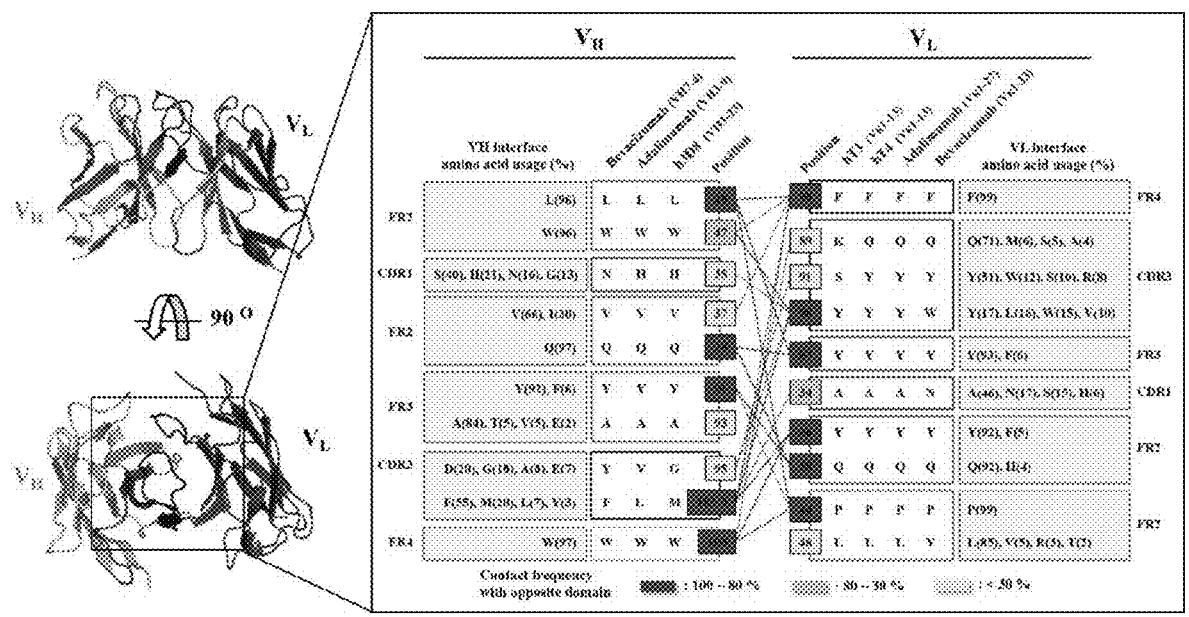

Image magnification, x100; scale bar, 20 μm.

Image magnification, 630x; scale bar, 5 μm.

Cell-penetrating & Cytosol-localizing IgG antibody (IgG cytotransmab)
(e.g., TMab4)

Cell-penetrating, Cytosol-localizing & Ras·GTP-specific targeting IgG antibody (Anti-Ras·GTP iMab)
(e.g., RT4, RT11)

M : size marker

| KRas G12D·GTP | $k_a$ (M$^{-1}$S$^{-1}$) | $k_d$ (S$^{-1}$) | $K_D$ (M) |
|---|---|---|---|
| RT4 | $2.99 \times 10^4$ | $3.5 \times 10^{-3}$ | $1.1 \times 10^{-7}$ |

Image magnification, 630x; scale bar, 5 μm.

NIH3T3 – mCherry HRas G12V

Image magnification, 630x; scale bar, 5 μm.

NIH3T3 – mCherry KRas G12V

Image magnification, 630x; scale bar, 5 μm.

METHOD FOR POSITIONING, IN CYTOPLASM, ANTIBODY HAVING COMPLETE IMMUNOGLOBULIN FORM BY PENETRATING ANTIBODY THROUGH CELL MEMBRANE, AND USE FOR SAME

CROSS REFERENCE TO RELATED APPLICATIONS

This application is a U.S. national phase under the provisions of 35 U.S.C. § 371 of International Patent Application No. PCT/KR15/07626 filed Jul. 22, 2015, which in turn claims priority of Korean Patent Application No. 10-2014-0092673 filed Jul. 22, 2014 and Korean Patent Application No. 10-2015-0103163 filed Jul. 21, 2015. The disclosures of such international patent application and Korean priority patent applications are hereby incorporated herein by reference in their respective entireties, for all purposes.

TECHNICAL FIELD

The present invention relates to a method of localizing an intact immunoglobulin-format antibody in cytosol by actively permeating membrane of cells.

The present invention also relates to a light-chain variable region that induces an intact immunoglobulin-format antibody to be localized in cytosol by permeating a membrane of cells, and relates to an antibody comprising the same.

The present invention also relates to a biologically active molecule fused to the antibody and selected from the group consisting of peptides, proteins, small-molecule drugs, nanoparticles and liposomes.

The present invention also relates to a composition for prevention, treatment or diagnosis of cancer, comprising: the antibody; or a biologically active molecule fused to the antibody and selected from the group consisting of peptides, proteins, small-molecule drugs, nanoparticles and liposomes.

The present invention also relates to a polynucleotide that encodes the light-chain variable region and the antibody.

The present invention also relates to a method for producing an antibody that is localized in cytosol by penetrating cells, the method comprising a step of replacing a light-chain variable region of an antibody with the light-chain variable region having an ability to be localized in the cytosol by penetrating cells.

BACKGROUND ART

Intact immunoglobulin-format antibody has a highly stable Y-shaped structure (molecular weight: 150 kDa) composed of two heavy-chain (50 kDa) proteins and two light-chain (25 kDa) proteins. The antibody light-chain and heavy-chain are divided into variable regions whose amino acid sequences differ between antibodies, and constant regions whose amino acid sequences are the same between antibodies. The heavy-chain constant region includes CH1, hinge, CH2 and CH3 domains, and the light-chain constant region includes a Cκ or a Cλ domain. Antibody heavy-chain and light-chain variable regions have portions whose amino acid sequences particularly differ between antibodies, and these portions constitute antigen-binding sites, and thus are also called "complementarity determining regions (CDRs)". When the three-dimensional structures of antibodies are examined, these CDRs form a loop on the antibody surface. Below the loop, a framework region that structurally supports the loop exists. In each of the heavy chain and the light chain, three loop structures exist, and these six loop structures are combined with one another and come into direct contact with antigen. The heavy-chain constant region (Fc) of antibody guarantees a long half-life in blood by its binding to FcRn (neonatal Fc receptor), and due to this characteristic, the antibody can be long-lasting in the body, unlike small-molecule drugs. Furthermore, the binding of antibody to FcγR (Fc gamma receptor) or the like makes it possible to specifically induce the death of cells which overexpress a target substance, through antibody-dependent cellular cytotoxicity and complement-dependent cellular cytotoxicity. Antibodies recently developed in various species for the purpose of treating various diseases can exhibit improved therapeutic effects through various humanization methods such as a method of CDR-grafting with a human antibody FR (framework) in order to overcome immunogenicity.

Conventional antibodies cannot directly penetrate living cells due to their large size and hydrophilic nature. Thus, most conventional antibodies specifically target extracellularly secreted proteins or cell membrane proteins (Kim S J et al., 2005). General antibodies and macromolecular biodrugs have limitations in that they cannot pass the hydrophobic cell membrane, and thus cannot bind to and inhibit various disease-related substances. Generally, commercial antibodies binding specifically to intracellular substances, which are used in experiments for studies on mechanisms such as the growth, specific inhibition, etc. of cells, cannot be used directly to treat living cells, and in order for these antibodies to bind to intracellular substances, a pretreatment process for forming pores in the cell membrane by a cell membrane permeabilization process using the amphipathic glycoside saponin is necessarily required. Small-molecule substances, nucleic acids or nanoparticles, etc., can be transported into living cells by use of various reagents or methods such as electroporation or heat shock, but proteins or antibodies can lose their activity, because the above-described most reagents and experimental conditions adversely affect the characteristic three-dimensional structures of the proteins or antibodies. Intracellular antibodies (intrabodies), which bind specifically to intracellular proteins and inhibit their activity, have been developed, but these antibodies also have no ability to penetrate the membrane of living cells, and thus may be applied only for gene therapy, and the applicability thereof in future is very limited (Manikandan J et al., 2007).

Unlike various types of antibody fragments, including intact immunoglobulin-format antibodies as described above, macromolecular substances such as recombinant proteins, etc., small-molecule substances easily and effectively penetrate living cells due to their small size and hydrophobic nature. However, in order for small-molecule drugs to bind specifically to various disease-related substances in cells, the surface of target substances is required to have a hydrophobic pocket. Target substances having this hydrophobic pocket form only about 10% of total disease-related substances in cells, and for this reason, small-molecule drugs cannot specifically target most pathogenic proteins in cells (Imai K et al., 2006).

In various diseases, including cancer, there occur the mutation and abdominal overexpression of either proteins that play an important role in intracellular protein-protein interactions (PPIs) or various proteins related to transcription or signaling. Among such proteins, particularly disease-related substances that show complex interactions through their large and flat surface are difficult to specifically inhibit by small-molecule drugs as described above (Blundell et al., 2006). As an example, RAS, which is one of cytosolic important tumor-related factors (therapeutic agents for which do not currently exist), acts as a molecular switch that transmits an extracellular signal through a cell membrane receptor to the intracellular signaling system. In about 30% of human cancers, particularly colorectal cancer and pancreatic cancer, RAS is always activated in cells due to cancer-related mutations, and such carcinogenesis-related mutations are known as major tumor-related factors that impart strong resistance to conventional anticancer therapy (Scheffzek K et al., 1997).

In an attempt to overcome current technical limitations, various studies have been conducted to impart cell-penetrating ability to antibody fragments or macromolecular substances, which can effectively inhibit protein-protein interactions. It was found that protein transduction domains (PTDs) having basic amino acid sequences and a hydrophobic or amphipathic nature have the ability to penetrate living cells (Leena N et al., 2007). Furthermore, many attempts have been made to fuse the protein transduction domains to various types of antibody fragments by genetic engineering methods in order to recognize specific intracellular proteins. However, most fusion proteins are not secreted from animal cells or are released into supernatants in only very small amounts (NaKajima O et al., 2004), and fusion proteins with a protein transduction domain rich in arginine have problems in that they are weak against host Furin protease during production (Chauhan A et al., 2007). In addition, there is a problem in that the cell-penetrating efficiency of fusion proteins is poor, making it difficult to develop these fusion proteins into therapeutic antibodies (Falnes P et al., 2001). In an attempt to overcome expression-associated problems, studies have been conducted to fuse cell-penetrating domains by chemical covalent bonds or biotin-streptavidin bonds after protein purification, but these methods result in the structural deformation of proteins.

In addition, studies conducted using some autoantibodies reported that antibodies and short-chain variable region (scFv) antibody fragments can penetrate into cells by endocytosis. Autoantibodies are anti-DNA antibodies that are found mainly in humans and mice with autoimmune disease, and some of these autoantibodies have the property of penetrating living cells (Michael R et al., 1995; Michael P et al., 1996; Jeske Zack D et al., 1996). Cell-penetrating autoantibodies reported to date mostly localize to the nucleus after their introduction into cells, and studies have been actively conducted to fuse these cell-penetrating autoantibodies with specific proteins showing effects in the nucleus (Weisbart et al., 2012). However, protein penetration into living cells by use of autoantibodies has limitations in that the protein finally localize to the nucleus, and thus cannot bind specifically to various disease-related substances in the intracellular cytosol and cannot inhibit the activity thereof.

Among naturally occurring macromolecular substances, typical substances having the property of penetrating cells include viruses (HIV, HSV), toxins (cholera toxin, diphtheria toxin), etc. It is known that these substances penetrate cells by endocytosis that is an active intracellular transport mechanism. This endocytosis is largely classified into three pathways: endocytosis by clathrin that is involved in the internalization of a receptor by ligand binding; endocytosis by caveolae that are found in some toxins such as cholera toxin; and macropinocytosis that is found in dextran, Ebola virus, etc. Endocytosis in which clathrin and caveolae are involved mainly begins when receptors distributed on the cell membrane bind to specific ligands. Clathrin localizes to the inner surface of the cell membrane. When a substance binds to a receptor, the clathrin protein makes a fibrous shell to form a vesicle which moves into cells. Caveolae form an oligomer by action of caveolin-1 protein while forming a stable vesicle (caveosome) which moves into the cytosol. In macropinocytosis, a portion of the cell membrane protrudes to surround a substance to thereby form a macropinosome which moves into the cytosol (Gerber et al., 2013). Substances that penetrated the cytosol through such endocytosis pathways are mostly degraded through a lysosomal pathway in the absence of an additional endosomal escape mechanism.

In order to avoid from being degraded through the lysosomal pathway, viruses, toxins and the like have a mechanism by which they escape from the endosome into the cytosol. Although the endosomal escape mechanism has not yet been clearly found, three hypotheses for the endosomal escape mechanism are known to date. The first hypothesis is a mechanism by which a pore is formed in the endosomal membrane. In this hypothesis, substances such as cationic amphiphilic peptides in the endosomal membrane bind to a negatively charged cellular lipid bilayer to cause internal stress or inner membrane contraction to thereby form a barrel-stave pore or a toroidal channel (Jenssen et al., 2006). The second hypothesis is a mechanism by which the endosome bursts as a consequence of the proton-sponge effect. In this hypothesis, due to the high buffering effect of a substance having a protonated amino group, the osmotic pressure of the endosome can be increased so that the endosomal membrane can be degraded (Lin and Engbersen, 2008). In the third hypothesis, a specific motif, which maintains a hydrophilic coil shape in a neutral environment but is changed into a hydrophobic helical structure in an acidic environment such as endosome, escapes from the endosome by fusion to the endosomal membrane (Horth et al., 1991). However, studies conducted to demonstrate endosome escape mechanisms for a variety of naturally occurring substances based on the above-described hypotheses are still insufficient.

Accordingly, the present inventors have developed a humanized light-chain variable (VL) single domain that penetrates cells and is localized in the cytosol. Furthermore, in order to construct a stable intact immunoglobulin-format antibody, the present inventors have improved a light-chain variable single domain (VL) antibody fragment having cytosol-penetrating ability so as to easily interact with and bind to various human heavy-chain variable regions (VH) while maintaining its ability to penetrate cells and to be localized in the cytosol, thereby developing an intact immunoglobulin-format antibody (Cytotransmab) that penetrates cells and is localized in the cytosol.

Moreover, the present inventors have screened a heavy-chain variable region (VH) library to select a heavy-chain variable region (VH) having the ability to bind specifically to activated RAS, and have replaced the heavy-chain variable region (VH) of an intact immunoglobulin-format antibody, which penetrates cells and localizes in the cytosol, with the selected heavy-chain variable region (VH), thereby constructing an intact immunoglobulin-format anti-RAS cytosol-penetrating antibody (iMab (internalizing & interfering monoclonal antibody)) that can penetrate living cells and bind specifically to activated RAS in the cytosol to thereby inhibit cell growth signaling.

In addition, the present inventors have found that the anti-RAS cytosol-penetrating monoclonal antibody penetrates various RAS-dependent cancer cell lines and inhibits cell growth by specifically neutralization of RAS in the cytosol, and have found that, even when the antibody is fused with a peptide for imparting tumor tissue specificity, it exhibits an activity of specifically inhibiting activated RAS in RAS-dependent tumors without adversely affecting the ability to penetrate the cytosol and neutralize activated RAS, thereby completing the present invention.

DISCLOSURE OF INVENTION

Technical Problem

Therefore, it is an object of the present invention to provide a method of localizing an intact immunoglobulin-format antibody in cytosol by an endosomal escape mechanism, after actively permeating membrane of living animal cells by an endocytosis process.

Another object of the present invention is to provide a light-chain variable region (VL) and an antibody comprising the same that induces an intact immunoglobulin-format antibody to be localized in cytosol by an endosomal escape mechanism, after actively permeating membrane of living animal cells by an endocytosis process.

Still another object of the present invention is to provide a biologically active molecule fused to the antibody and selected from the group consisting of peptides, proteins, small-molecule drugs, nanoparticles and liposomes.

Still another object of the present invention is to provide a composition for prevention, treatment or diagnosis of cancer, comprising: the antibody; or a biologically active molecule fused to the antibody and selected from the group consisting of peptides, proteins, small-molecule drugs, nanoparticles and liposomes.

Still another object of the present invention is to provide a polynucleotide that encodes the light-chain variable region and the antibody.

Yet another object of the present invention is to provide a method for producing an antibody that penetrates cells and is localized in the cytosol, the method comprising a step of replacing a light-chain variable region of an antibody with the light-chain variable region having the ability to actively penetrate living cells and to be localized in the cytosol by inducing an endosomal escape mechanism.

Technical Solution

To achieve the above object, the present invention provides a method of localizing an intact immunoglobulin-format antibody in cytosol by permeating membrane of cells, wherein the antibody comprises a light-chain variable region (VL) having the ability to penetrate the cytosol.

Hereinafter, the present invention will be described in detail.

According to the above-described method of the present invention, an intact immunoglobulin antibody-format can penetrate the membrane of living cells and localize in the cytosol, by a light-chain variable region (VL) capable of inducing the intact immunoglobulin-format antibody to penetrate the membrane of living cells by endocytosis and to be localized in the cytosol by inducing an endosome escape mechanism.

Specifically, the antibody of the present invention is an antibody is an intact immunoglobulin-format antibody that can exhibit both the ability to penetrate the membrane of living cells and the ability to be localized in the cytosol, and a light-chain variable region corresponding to a partial fragment of the antibody exhibits the ability to penetrate cells and to be localized in the cytosol.

FIG. 1 schematically shows the intracellular activity of an antibody or antibody light-chain variable region of the present invention.

The antibody may be a chimeric, human or humanized antibody.

The antibody may be IgG, IgM, IgA, IgD, or IgE. For example, the antibody may be IgG1, IgG2, IgG3, IgG4, IgM, IgE, IgA1, IgA5, or IgD, and may be most preferably IgG type monoclonal antibody.

In the present invention, an intact immunoglobulin-format antibody has a structure with two full-length light chains and two full-length heavy chains, and each light chain is linked to each heavy chain by a disulfide bond (SS-bond). A constant region of the antibody is divided into a heavy-chain constant region and a light-chain constant region, and the heavy-chain constant region has γ, μ, α, δ, and ε types, and γ1, γ2, γ3, γ4, α1 and α2 subclasses. The light-chain constant region has κ and λ types.

The term "heavy chain" as used herein may be interpreted to include a full-length heavy chain including variable region domain VH including an amino acid sequence having a variable region sequence sufficient to confer antigen-specificity and three constant region domains CH1, CH2 and CH3, and a fragment thereof. Also, the term "light chain" as used herein may be interpreted to include a full-length light chain including a variable region domain VL including an amino acid sequence having a variable region sequence sufficient to confer antigen-specificity and a constant region domain CL, and a fragment thereof.

The ability to penetrate the cytosol may be the ability to actively penetrate living cells by endocytosis, and then to be localized in the cytosol by endosome escape.

In one embodiment of the present invention, the light-chain variable region having the ability to penetrate the cytosol may comprise:

either a CDR1 comprising an amino acid sequence selected from the group consisting of SEQ ID NOs: 4, 7 and 10, or a sequence having a homology of at least 90% to the CDR1; and either a CDR3 comprising an amino acid sequence selected from the group consisting of SEQ ID NOs: 6, 9 and 12, or a sequence having a homology of at least 90% to the CDR3.

Information about the sequences of the CDR1, CDR2 and CDR3 is as follows.

| Names of light chain variables regions | CDR1 Sequence | | | | | | | | | | | | | | | | SEQ ID |
|---|---|---|---|---|---|---|---|---|---|---|---|---|---|---|---|---|---|
| Kabat No. | 24 | 25 | 26 | 27 | 27a | 27b | 27c | 27d | 27e | 27f | 28 | 29 | 30 | 31 | 32 | 33 | 34 | NO: |
| hT2 VL | K | S | S | Q | S | L | F | N | S | R | T | R | K | N | Y | L | A | 4 |
| hT3 VL | K | S | S | Q | S | L | F | N | S | R | T | R | K | N | Y | L | A | 7 |
| hT4 VL | K | S | S | Q | S | L | F | N | S | R | T | R | K | N | Y | L | A | 10 |

-continued

| Names of light chain variables regions | CDR2 Sequence | | | | | | | SEQ ID NO: | CDR3 Sequence | | | | | | | SEQ ID NO: |
|---|---|---|---|---|---|---|---|---|---|---|---|---|---|---|---|---|
| Kabat No. | 50 | 51 | 52 | 53 | 54 | 55 | 56 | 89 | 90 | 91 | 92 | 93 | 94 | 95 | 96 | 97 |
| hT2 VL | W | A | S | T | R | E | S | 5 | K | Q | S | Y | Y | H | W | Y | T | 6 |
| hT3 VL | W | A | S | T | R | E | S | 8 | K | Q | S | Y | Y | H | W | Y | T | 9 |
| hT4 VL | W | A | S | T | R | E | S | 11 | Q | Q | Y | Y | Y | H | W | Y | T | 12 |

More preferably, the light-chain variable region may further comprise either a CDR2 comprising an amino acid sequence selected from the group consisting of SEQ ID NOs: 5, 8 and 11, or a sequence having a homology of at least 90% to the CDR2.

In one embodiment of the present invention, the light-chain variable region may comprise CDR1 of SEQ ID NO: 4, CDR2 of SEQ ID NO: 5, and CDR3 of SEQ ID NO: 6.

In another embodiment of the present invention, the light-chain variable region may comprise CDR1 of SEQ ID NO: 7, CDR2 of SEQ ID NO: 8, and CDR3 of SEQ ID NO: 9.

In another embodiment of the present invention, the light-chain variable region may comprise CDR1 of SEQ ID NO: 10, CDR2 of SEQ ID NO: 11, and CDR3 of SEQ ID NO: 12.

In one embodiment of the present invention, the light-chain variable region may be one wherein $2^{nd}$ and $4^{th}$ amino acids, numbered starting from the N-terminus of the light-chain variable region, are substituted with leucine (L) and methionine (M), respectively.

in the FR (framework) differ from those in Trastuzumab (Herceptin) which is high stable and comprising the heavy-chain variable region of the VH3 subgroup and the light-chain variable region of the Vκ1 subgroup, among commercially available humanized antibodies approved by the FDA.

In another embodiment of the present invention, the light-chain variable region may be one wherein $89^{th}$ and $91^{st}$ amino acids, numbered starting from the N-terminus of the light-chain variable region, are substituted with glutamine (Q) and tyrosine (Y), respectively.

This light-chain variable region is obtained based on the results of analysis of VH-VL interface residues between human antibody variable regions, which indicate that two residues in the mouse CDR3 of a conventional cytosol-penetrating light-chain variable region differ.

In a preferred embodiment of the present invention, the light-chain variable region may comprise an amino acid sequence selected from the group consisting of SEQ ID NOs: 1, 2 and 3.

Information about the sequences is as follows.

| Names of light chain variable regions | Sequences | SEQ ID NOS: |
|---|---|---|
| hT2 VL | 1          10          20    abcdef 30          40          50<br>DLVMTQSPATLSLSPGERATLSCKSSQSLFNSRTRKNYLAWYQQKPGQAPRLLIYW<br>          60          70          80          90          100<br>ASTRESGIPGRFSGSGSGTDFTLTISSLEPEDFAVYYCKQSYYHMYTFGQGTKVEIKR | SEQ ID NO: 1 |
| hT3 VL | 1          10          20    abcdef 30          40          50<br>DLVMTQSPSSLSASVGDRVTITCKSSQSLFNSRTRKNYLAWYQQKPGKAPKLLIYW<br>          60          70          80          90          100<br>ASTRESGVPSRFSGSGSGTDFTLTISSLQPEDFATYYCKQSYYHMYTFGQGTKVEIKR | SEQ ID NO: 2 |
| hT4 VL | 1          10          20    abcdef 30          40          50<br>DLVMTQSPSSLSASVGDRVTITCKSSQSLFNSRTRKNYLAWYQQKPGKAPKLLIYW<br>          60          70          80          90          100<br>ASTRESGVPSRFSGSGSGTDFTLTISSLQPEDFATYYCKQSYYHMYTFGQGTKVEIKR | SEQ ID NO: 3 |

This light-chain variable region is one obtained by substituting the $2^{nd}$ and $4^{th}$ residues important to obtain a CDR structure that retains its ability to penetrate cytosol, among residues included in the CDR Vernier zone located in the FR (framework).

In one embodiment of the present invention, the light-chain variable region may be one wherein $9^{th}$, $10^{th}$, $13^{th}$, $17^{th}$, $19^{th}$, $21^{st}$, $22^{nd}$, $42^{nd}$, $45^{th}$, $58^{th}$, $60^{th}$, $79^{th}$ and $85^{th}$ amino acids numbered starting from the N-terminus of the light-chain variable region, are substituted with serine (S), serine (S), alanine (A), valine (V), aspartic acid (D), valine (V), isoleucine (I), threonine (T), lysine (K), lysine (K), valine (V), serine (S), glutamine (Q) and threonine (T), respectively.

This light-chain variable region is one obtained based on the sequencing results indicating that a total of 14 residues Names and sequences of cytosol-penetrating humanized light-chain variable region (VL) single domains All the residues indicated in SEQ ID NOs provided herein were numbered according to the Kabat numbering system (Kabat E A et al., 1991).

In one embodiment of the present invention, the cells, into which the antibody penetrate and localize in the cytosol, may be living animal cells. Namely, the antibody may actively penetrate living animal cells.

In one embodiment of the present invention, the antibody may target not only the cytosol, but also various organelles present in the cytosol, and molecules present in cells. For example, the antibody may be one that targets cytosolic, nuclear, mitochondrial, endoplasmic reticulum, and/or organelle macromolecules, but is not limited thereto.

In one embodiment of the present invention, the organelle macromolecule may be protein, lipid, DNA or RNA. More specifically, the protein may be one associated with control of cell growth, cell proliferation, cell cycle, DNA repair, DNA integrity, transcription, replication, translation, or intracellular transport. The protein may be one modified, activated or mutated with phosphate group, carboxylic acid group, methyl group, sulfate group, lipid, hydroxyl group, or amide group.

In the most preferable embodiment of the present invention, the antibody may target and bind specifically to RAS activated in the cytosol. The activated RAS may be a GTP-bound tumor related factor, and the RAS may be mutant RAS. Mutations of the RAS may be various mutations related to diseases, and examples thereof include, but are not limited to, substitution mutations at glycine 12, glycine 13 and glutamine 61 of KRas, HRas or NRas.

In one embodiment of the present invention, the binding affinity of the antibody for the activated RAS in the cytosol may be attributable to the heavy-chain variable region (VH) of the antibody.

In one embodiment of the present invention, the heavy-chain variable region may comprise:

a CDR1 of SEQ ID NO: 14 or an amino acid sequence having a homology of at least 90% thereto;

a CDR2 of SEQ ID NO: 15 or an amino acid sequence having a homology of at least 90% thereto; and a CDR3 of SEQ ID NO: 16 or an amino acid sequence having a homology of at least 90% thereto.

Information about these sequences is as follows.

In an example of the present invention, screening was performed using a library in which artificial mutations at a total of 18 residues in CDR1, CDR2 and CDR3 regions were induced in a state in which a constructed human heavy-chain variable region (VH) and a heavy-chain constant region (CH1) were fused to each other.

In an example of the present invention, using a library in which the human heavy-chain variable region (VH) and the heavy-chain constant region (CH1) were fused to each other, a heavy-chain variable region was selected, which can bind specifically to activated (GTP-bound) RAS even in a state in which it is fused to a cytosol-penetrating humanized light-chain variable region (VL).

In an example of the present invention, KRas G12D which is an activated (GTP-bound) RAS mutant was used as a target molecule. In one embodiment, cancer-associated RAS mutations occur mainly at residues 12, 13 and 61, in which residues 12 and 13 are located in the P-loop of the RAS protein, and affect the binding of GAP (GTPase-activating protein) that hydrolyzes GTP bound to the RAS protein to induce the change of the protein structure to an inactivated form. Furthermore, residue 61 binds to the hydrolytic active site of GAP to prevent the hydrolysis of GTP. Thus, various cancer-associated RAS mutations are not limited to KRas G12D mutations, because signaling-associated regions (Switch I and Switch II) thereof are equal to those of RAS G12D mutations.

In one embodiment, a catalytic domain ranging from residue 1 to residue 165 in each of NRas and HRas has a similarity of at least 85% to that in KRas. In the catalytic

| Names of light chain variables regions | CDR1 Sequence | | | | | SEQ ID NO: | CDR2 Sequence | | | | | | | | | |
|---|---|---|---|---|---|---|---|---|---|---|---|---|---|---|---|---|
| Kabat No. | 32 | 32 | 33 | 34 | 35 | | 50 | 51 | 52 | 52a | 53 | 54 | 55 | 56 | 57 | 58 | 59 |
| RT4 | S | Y | A | M | S | 14 | T | I | S | R | S | G | H | S | T | Y | Y |

| Names of light chain variables regions | CDR2 Sequence | | | | | SEQ ID NO: | CDR3 Sequence | | | | | | | | SEQ ID NO: |
|---|---|---|---|---|---|---|---|---|---|---|---|---|---|---|---|
| Kabat No. | 60 | 61 | 62 | 63 | 64 | 65 | 95 | 96 | 97 | 98 | 99 | 100 | 100a | 101 | 102 |
| RT4 | A | D | S | V | K | G | 15 | R | F | G | S | I | V | F | D | Y | 16 |

In a more preferable embodiment of the present invention, the heavy-chain variable region may comprise an amino acid sequence of SEQ ID NO: 13.

Information about this sequence is as follows.

| Names of heavy chain variable regions | Sequences | SEQ ID NOS: |
|---|---|---|
| RT4 | EVQLVESGGGLVQPGGSLRLSCAASGTFSSYAMSWVRQAPGKGLEWVSTISRSGHSTY YADSVKGRFTISRDNSKNTLYLQMNSLRAEDTAVYYCAKRFGSIVFDYWGQGTLVT- VSS | 13 |

The heavy-chain variable region, which binds specifically to RAS and inhibits the activity thereof, was screened by the following method.

189 has a similarity of 15%, but the structure thereof does not influence downstream signaling. Thus, the target molecule used is not limited to activated KRas G12D.

domain, Switch I (residues 32 to 38) and Switch II (residues 59 to 67), which bind to downstream signaling substances, are perfectly consistent with those in KRas. However, the C-terminal early domain ranging from residue 165 to residue In an example of the present invention, using a yeast cell surface display system, initial screening was performed for activated (GTP-bound) RAS in a state in which the heavy-chain variable region (VH) and the heavy-chain constant region (CH1) were expressed. Thereafter, Fab was screened by mating with yeast that expresses and secretes a light chain comprising the cytosol-penetrating light-chain variable region (VL) and the light-chain constant region (CL).

Another aspect of the present invention provides a light-chain variable region (VL) that induces an intact immunoglobulin-format antibody to penetrate the cell membrane and be localized in the cytosol.

In an example of the present invention, the light-chain variable region may comprise:

either a CDR1 comprising an amino acid sequence selected from the group consisting of SEQ ID NOs: 4, 7 and 10, or a sequence having a homology of at least 90% to the CDR1; and either a CDR3 comprising an amino acid sequence selected from the group consisting of SEQ ID NOs: 6, 9 and 12, or a sequence having a homology of at least 90% to the CDR3.

Also, in an example of the present invention, the light-chain variable region may be one wherein $2^{nd}$ and $4^{th}$ amino acids, numbered starting from the N-terminus of the light-chain variable region, are substituted with leucine (L) and methionine (M), respectively.

Also, in one embodiment of the present invention, the light-chain variable region may be one wherein $9^{th}$, $10^{th}$, $13^{th}$, $17^{th}$, $19^{th}$, $21^{st}$, $22^{nd}$, $42^{nd}$, $45^{th}$, $58^{th}$, $60^{th}$, $79^{th}$ and $85^{th}$ amino acids, numbered starting from the N-terminus of the light-chain variable region, are substituted with serine (S), serine (S), alanine (A), valine (V), aspartic acid (D), valine (V), isoleucine (I), threonine (T), lysine (K), lysine (K), valine (V), serine (S), glutamine (Q) and threonine (T), respectively.

In another embodiment of the present invention, the light-chain variable region may be one wherein $89^{th}$ and $91^{st}$ amino acids, numbered starting from the N-terminus of the light-chain variable region, are substituted with glutamine (Q) and tyrosine (Y), respectively.

In addition, in a preferred embodiment of the present invention, the light-chain variable region may comprise an amino acid sequence selected from the group consisting of SEQ ID NOs: 1, 2 and 3.

The cell-penetrating ability of the light-chain variable region according to the present invention may be the ability to penetrate cells by endocytosis, and then localize in the cytosol by escaping endosome. Still another aspect of the present invention provides an antibody comprising the light-chain variable region.

In one embodiment of the present invention, the antibody may be one that penetrates the cell membrane and localizes in the cytosol. The antibody may be a chimeric, human or humanized antibody. The antibody may be any one selected from the group consisting of IgG, IgM, IgA, IgD, and IgE. The antibody may be one that targets cytosolic, nuclear, mitochondrial, endoplasmic reticulum, and/or organelle macromolecules. The organelle macromolecule may be protein, lipid, DNA or RNA. The protein may be one associated with control of cell growth, cell proliferation, cell cycle, DNA repair, DNA integrity, transcription, replication, translation, or intracellular transport. In a preferred embodiment of the present invention, the antibody may be one that binds specifically to activated RAS in the cytosol, and may comprise a heavy-chain variable region (VH) that binds specifically to activated RAS in the cytosol. The activated RAS may be mutated RAS.

In addition, the heavy-chain variable region may comprise:

a CDR1 comprising an amino acid sequence, which has at least 90% homology with an amino acid sequence as set forth in SEQ ID No:14;

a CDR2 comprising an amino acid sequence, which has at least 90% homology with an amino acid sequence as set forth in SEQ ID No:15; and a CDR3 comprising an amino acid sequence, which has at least 90% homology with an amino acid sequence as set forth in SEQ ID No:16.

In a more preferable embodiment of the present invention, the heavy-chain variable region may comprise an amino acid sequence of SEQ ID NO: 13.

One aspect of the present also provides a biologically active molecule fused to the antibody and selected from the group consisting of peptides, proteins, small-molecule drugs, nanoparticles and liposomes.

The proteins may be antibodies, antibody fragments, immuoglubulin, peptides, enzymes, growth factors, cytokines, transcription factors, toxins, antigen peptides, hormones, carrier proteins, motor function proteins, receptors, signaling proteins, storage proteins, membrane proteins, transmembrane proteins, internal proteins, external proteins, secretory proteins, viral proteins, glycoproteins, cleaved proteins, protein complexes, chemically modified proteins, or the like.

A specific embodiment of the present invention provides an RGD4C peptide fused to the N-terminus of the light-chain variable region of an intact immunoglobulin-format antibody that binds specifically to and inhibits activated (CTP-bound) RAS by cytosolic penetration. In an embodiment, the RGD4C peptide is preferably fused to the N-terminus of the light-chain variable region by a $(G_4S)_1$ linker, but is not limited thereto.

As used herein, the term "small-molecule drugs" refers to organic compounds, inorganic compounds or organometallic compounds that have a molecular weight of less than about 1000 Da and are active as therapeutic agents against diseases. The term is used in a broad sense herein. The small-molecule drugs herein encompass oligopeptides and other biomolecules having a molecular weight of less than about 1000 Da.

As used herein, the term "nanoparticle" refers to a particle including substances ranging between 1 and 1,000 nm in diameter. The nanoparticle may be a metal nanoparticle, a metal/metal core shell complex consisting of a metal nanoparticle core and a metal shell enclosing the core, a metal/non-metal core shell consisting of a metal nanoparticle core and a non-metal shell enclosing the core, or a non-metal/metal core shell complex consisting of a non-metal nanoparticle core and a metal shell enclosing the core. According to an embodiment, the metal may be selected from gold, silver, copper, aluminum, nickel, palladium, platinum, magnetic iron and oxides thereof, but is not limited thereto, and the non-metal may be selected from silica, polystyrene, latex and acrylate type substances, but is not limited thereto.

In the present invention, liposomes include at least one lipid bilayer enclosing the inner aqueous compartment, which is capable of being associated by itself. Liposomes may be characterized by membrane type and size thereof. Small unilamellar vesicles (SUVs) may have a single membrane and may range between 20 and 50 nm in diameter. Large unilamellar vesicles (LUVs) may be at least 50 nm in diameter. Oliglamellar large vesicles and multilamellar large vesicles may have multiple, usually concentric, membrane layers and may be at least 100 nm in diameter. Liposomes with several nonconcentric membranes, i.e., several small vesicles contained within a larger vesicle, are referred to as multivesicular vesicles.

As used herein, the term "fusion" refers to unifying two molecules having the same or different function or structure, and the methods of fusing may include any physical, chemical or biological method capable of binding the tumor tissue-penetrating peptide to the protein, small-molecule drug, nanoparticle or liposome. Preferably, the fusion may be made by a linker peptide, and for example, the linker peptide may mediate the fusion with the bioactive molecules at various locations of an antibody light-chain variable region of the present invention, an antibody, or fragments thereof.

The present invention also provides a pharmaceutical composition for prevention or treatment of cancer, comprising: the antibody; or a biologically active molecule fused to the antibody and selected from the group consisting of peptides, proteins, small-molecule drugs, nanoparticles and liposomes.

The use of the composition for prevention or treatment of cancer, comprising: the antibody according to the present invention; or a biologically active molecule fused to the antibody and selected from the group consisting of peptides, proteins, small-molecule drugs, nanoparticles and liposomes can penetrate cells and remain in the cytosol, without affecting the high specificity and affinity of a human antibody heavy-chain variable region (VH) for antigens, and thus can localize in the cytosol which is currently classified as a target in disease treatment based on small-molecule drugs, and at the same time, can exhibit high effects on the treatment and diagnosis of tumor and disease-related factors that show structurally complex interactions through a wide and flat surface between protein and protein. In addition, these can selectively inhibit KRas mutants, which are major drug resistance-associated factors in the use of various conventional tumor therapeutic agents, and at the same time, can be used in combination with conventional therapeutic agents to thereby exhibit effective anticancer activity.

The cancer may be selected from the group consisting of squamous cell carcinoma, small cell lung cancer, non-small cell lung cancer, adenocarcinoma of lung, squamous cell carcinoma of lung, peritoneal cancer, skin cancer, skin or ocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatoma, gastrointestinal cancer, pancreatic cancer, glioblastoma, cervical cancer, ovarian cancer, liver cancer, bladder cancer, liver tumor, breast cancer, colon cancer, colorectal cancer, endometrial cancer or uterine cancer, salivary gland cancer, kidney cancer, liver cancer, prostate cancer, vulva cancer, thyroid cancer, liver cancer and head and neck cancer.

When the composition is prepared as a pharmaceutical composition for preventing or treating cancer or angiogenesis-related diseases, the composition may include a pharmaceutically acceptable carrier. The pharmaceutically acceptable carrier contained in the composition is typically used in the formulation. Examples of the pharmaceutically acceptable carrier included in the composition may include, but are not limited to, lactose, dextrose, sucrose, sorbitol, mannitol, starch, acacia rubber, calcium phosphate, alginate, gelatin, calcium silicate, minute crystalline cellulose, polyvinyl pyrrolidone, cellulose, water, syrup, methyl cellulose, methyl hydroxy benzoate, propyl hydroxy benzoate, talc, magnesium stearate and mineral oil, etc., but are not limited thereto. In addition to the above ingredients, the pharmaceutical composition may further include a lubricant, a wetting agent, a sweetener, a flavoring agent, an emulsifier, a suspension, a preservative, etc.

The pharmaceutical composition for preventing or treating cancer or angiogenesis-related diseases may be administered orally or parenterally. Such a parenteral administration includes intravenous injection, subcutaneous injection, intramuscular injection, intraperitoneal injection, endothelial administration, topical administration, nasal administration, intrapulmonary administration, intrarectal administration, etc. Because a protein or peptide is digested when administered orally, it is preferred that a composition for oral administration is formulated to coat an active substance or to be protected against degradation in stomach. Also, the pharmaceutical composition may be administered by any device which can transport active substances to target cells.

Proper dose of the pharmaceutical composition for preventing or treating cancer or angiogenesis-related diseases may vary according to various factors such as method for formulating, administration method, age, weight, gender, pathological state of patient, food, administration time, administration route, excretion rate and reaction sensitivity, etc. Preferably, a proper dose of the composition is within the range of 0.001 and 100 mg/kg based on an adult. The term "pharmaceutically effective dose" as used herein refers to an amount sufficient to prevent or treat cancer or angiogenesis-related diseases.

The composition may be formulated with pharmaceutically acceptable carriers and/or excipients according to a method that can be easily carried out by those skilled in the art, and may be provided in a unit-dose form or enclosed in a multiple-dose vial. Here, the formulation of the pharmaceutical composition may be in the form of a solution, a suspension, syrup or an emulsion in oily or aqueous medium, or may be extracts, powders, granules, tablets or capsules, and may further include a dispersion agent or a stabilizer. Also, the composition may be administered individually or in combination with other therapeutic agents, and may be administered sequentially or simultaneously with conventional therapeutic agents. Meanwhile, the composition includes an antibody or an antigen-binding fragment, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of antibody may be conjugated to liposome through disulphide exchange reaction. Liposome may further include chemical therapeutic agents such as Doxorubicin.

The present invention also provides a composition for diagnosis of cancer, comprising: the antibody; or a biologically active molecule fused to the antibody and selected from the group consisting of peptides, proteins, small-molecule drugs, nanoparticles and liposomes.

The term "diagnosis" as used herein refers to demonstrating the presence or characteristic of a pathophysiological condition. Diagnosing in the present invention refers to demonstrating the onset and progress of cancer.

The intact immunoglobulin-format antibody and a fragment thereof may bind to a fluorescent substance for molecular imaging in order to diagnose cancer through images.

The fluorescent substance for molecular imaging refers to all substances generating fluorescence. Preferably, red or near-infrared fluorescence is emitted, and more preferably, fluorescence with high quantum yield is emitted. However, the fluorescence is not limited thereto.

Preferably, the fluorescent substance for molecular imaging is a fluorescent substance, a fluorescent protein or other substances for imaging, which may bind to the tumor tissue-penetrating peptide that specifically binds to the intact immunoglobulin-format antibody and a fragment thereof (kds), but is not limited thereto.

Preferably, the fluorescent substance is fluorescein, BODYPY, tetramethylrhodamine, Alexa, cyanine, allopicocyanine, or a derivative thereof, but is not limited thereto.

Preferably, the fluorescent protein is Dronpa protein, enhanced green fluorescence protein (EGFP), red fluorescent protein (DsRFP), Cy5.5, which is a cyanine fluorescent substance presenting near-infrared fluorescence, or other fluorescent proteins, but is not limited thereto.

Preferably, other substances for imaging are ferric oxide, radioactive isotope, etc., but are not limited thereto, and they may be applied to imaging equipment such as MR, PET.

The present invention also provides a polynucleotide that encodes the light-chain variable region, or an antibody comprising the same, or a fragment thereof.

The term "polynucleotide" as used herein refers to a deoxyribonucleotide or ribonucleotide polymer present in a single-stranded or double-stranded form. It includes RNA genome sequence, DNA (gDNA and cDNA), and RNA sequence transcribed therefrom. Unless otherwise described, it also includes an analog of the natural polynucleotide.

The polynucleotide includes not only a nucleotide sequence encoding the above-described light-chain region, but also a complementary sequence thereto. The complementary sequence includes a sequence fully complementary to the nucleotide sequence and a sequence substantially complementary to the nucleotide sequence. For example, this means a sequence that may be hybridized with a nucleotide sequence encoding an amino acid sequence of any one of SEQ ID NO:1 to SEQ ID NO: 3 under stringent conditions known in the pertinent art.

Also, the polynucleotide may be modified. The modification includes the addition, deletion, or non-conservative substitution or conservative substitution of nucleotides. The polynucleotide encoding the amino acid sequence is interpreted to include a nucleotide sequence that has a substantial identity to the nucleotide sequence. The substantial identity may refer to a sequence having a homology of at least 80%, a homology of at least 90%, or a homology of at least 95% when aligning the nucleotide sequence to correspond to any other sequence as much as possible and analyzing the aligned sequence using an algorithm generally used in the pertinent art.

The present invention also provides a method for producing an antibody that penetrates living cells and localizes in the cytosol, the method comprising a step of replacing the light-chain variable region of an antibody with a light-chain variable region having the ability to penetrate living cells and localize in the cytosol.

One embodiment of the present invention may provide a method in which the light-chain variable region (VL) of a conventional intact immunoglobulin-format antibody is replaced with a cytosol-penetrating light-chain variable region (VL), so that the replaced intact immunoglobulin-format monoclonal antibody will have the same cytosol-penetrating property as that of the intact immunoglobulin-format monoclonal antibody having the ability to penetrate the cytosol.

In an embodiment of the present invention, an example of an intact immunoglobulin-format antibody which, by a cytosol-penetrating light-chain variable region (VL), penetrates cells and localizes in the cytosol, comprises the steps of:

(1) constructing a cytosol-penetrating light-chain expression vector cloned with nucleic acids in which a light-chain variable region (VL) in a light chain comprising the human light-chain variable region (VL) and a human light-chain constant region (CL) is replaced with a humanized light-chain variable region (VL);

(2) constructing a heavy-chain expression vector cloned with nucleic acids that encode a heavy chain which interacts with the constructed light chain in order to express an intact immunoglobulin-format antibody and which comprises a heavy-chain variable region (VH) and a heavy-chain constant region (CH1-hinge-CH2-CH3);

(3) co-transforming the constructed light-chain and heavy-chain expression vectors into a protein expression animal cell, and expressing in the cell an intact immunoglobulin-format antibody comprising a humanized light-chain variable region (VL) that penetrates cells and localizes in the cytosol; and (4) purifying and recovering the expressed intact immunoglobulin-format antibody having the ability to penetrate the cytosol.

The above-described method makes it possible to produce an intact immunoglobulin-format antibody having cytosol-penetrating ability by expressing a light-chain expressing vector and a heavy-chain expressing vector. Furthermore, transformation with a vector expressing a heavy chain comprising a heavy-chain variable region capable of recognizing a specific protein in cells makes it possible to express an antibody which is able to penetrate cells and localize in the cytosol to bind to the specific protein. The vector may be either a vector system that co-expresses the heavy chain and the light chain in a single vector or a vector system that expresses the heavy chain and the light chain in separate vectors. In the latter case, the two vectors may be introduced into a host cell by co-transformation and targeted transformation.

The term "vector" as used herein refers to a means for expressing a target gene in a host cell. For example, the vector may include plasmid vector, cosmid vector, bacteriophage vector, and virus vectors such as adenovirus vector, retrovirus vector, and adeno-associated virus vector. The vector that may be used as the recombinant vector may be produced by operating plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phages (for example, λgt4λB, λ-Charon, λΔz1 and M13, etc.), or virus (for example, CMV, SV40, etc.) commonly used in the pertinent art.

The light-chain variable region, the light-chain constant region (CL), the heavy-chain variable region (VH), and the heavy-chain constant region (CH1-hinge-CH2-CH3) of the present invention in the recombinant vector may be operatively linked to a promoter. The term "operatively linked" as used herein means a functional linkage between a nucleotide expression control sequence (such as a promoter sequence) and a second nucleotide sequence. Accordingly, the control sequence may control the transcription and/or translation of the second nucleotide sequence.

The recombinant vector may be generally constructed as a vector for cloning or a vector for expression. As the vector for expression, vectors generally used for expressing foreign protein from plants, animals or microorganisms in the pertinent art may be used. The recombinant vector may be constructed by various methods known in the pertinent art.

The recombinant vector may be constructed to be a vector that employs a prokaryotic cell or an eukaryotic cell as a host. For example, when the vector used is an expression vector and employs a prokaryotic cell as a host, the vector generally includes a strong promoter which may promote transcription (for example, pLλ promoter, trp promoter, lac promoter, tac promoter, T7 promoter, etc.), a ribosome binding site for initiation of translation, and termination sequences for transcription/translation. When the vector employs an eukaryotic cell as a host, a replication origin operating in the eukaryotic cell included in the vector may include an f1 replication origin, an SV40 replication origin, a pMB1 replication origin, an adeno replication origin, an AAV replication origin, a CMV replication origin and a BBV replication origin, etc., but is not limited thereto. In addition, a promoter derived from a genome of a mammal cell (for example, a metalthionine promoter) or a promoter derived from a virus of a mammal cell (for example, an adenovirus anaphase promoter, a vaccinia virus 7.5K promoter, a SV40 promoter, a cytomegalo virus (CMV) promoter, or a tk promoter of HSV) may be used, and the promoter generally has a polyadenylated sequence as a transcription termination sequence.

Another aspect of the present invention provides a host cell transformed with the recombinant vector.

Any kind of host cell known in the pertinent art may be used as a host cell. Examples of a prokaryotic cell include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus* and *Bascillus thuringiensis*, *Salmonella typhimurium*, intestinal flora and strains such as *Serratia marcescens* and various *Pseudomonas* Spp., etc. In addition, when the vector is transformed in an eukaryotic cell, a host cell such as yeast (*Saccharomyce cerevisiae*), an insect cell, a plant cell, and an animal cell, for example, SP2/0, CHO (Chinese hamster ovary) K1, CHO DG44, PER.C6, W138, BHK, COS-7, 293, HepG2, Huh7, 3T3, RN, and MDCK cell line, etc., may be used.

Another aspect of the present invention may provide a method for producing an intact immunoglobulin-format antibody that penetrates cells and localizes in the cytosol, the method comprising a step of culturing the above-described host cell.

A recombinant vector may be inserted into a host cell using an insertion method well known in the pertinent art. For example, when a host cell is a prokaryotic cell, the transfer may be carried out according to $CaCl_2$ method or an electroporation method, etc., and when a host cell is an eukaryotic cell, the vector may be transferred into a host cell according to a microscope injection method, calcium phosphate precipitation method, an electroporation method, a liposome-mediated transformation method, and a gene bombardment method, etc., but the transferring method is not limited thereto. When using microorganisms such as *E. coli*, etc. the productivity is higher than using animal cells. However, although it is not suitable for production of intact Ig form of antibodies due to glycosylation, it may be used for production of antigen binding fragments such as Fab and Fv.

The method for selecting the transformed host cell may be readily carried out according to a method well known in the pertinent art using a phenotype expressed by a selected label. For example, when the selected label is a specific antibiotic resistance gene, the transformant may be readily selected by culturing the transformant in a medium containing the antibiotic.

Still another aspect of the present invention may provide a method for producing an intact immunoglobulin-format antibody, which penetrates the cytosol and binds specifically to the activated (GTP-bound) tumor-associated factor RAS in the cytosol and inhibits the activity of the RAS, using an intact immunoglobulin-format antibody that penetrates living cells and localizes in the cytosol.

In an embodiment of the present invention, an intact immunoglobulin-format antibody, which penetrates animal cells and localizes in the cytosol and binds specifically to activated (GTP-bound) RAS in the cytosol, is produced using a heavy-chain variable region (VH) having the ability to bind specifically to activated (GTP-bound) RAS, and may be produced by a method comprising the steps of:

(1) constructing a heavy-chain expression vector cloned with nucleic acids comprising a human heavy-chain variable region (VH), which binds specifically to activated (GTP-bound) RAS, and a heavy-chain constant region (CH1-hinge-CH2-CH3);

(2) co-transforming the constructed heavy-chain expression vector and a cell-penetrating light-chain expression vector into a protein expression animal cell, and expressing in the cell an intact immunoglobulin-format antibody that penetrates living cells and localizes in the cytosol to specifically recognize activated (GTP-bound) RAS; and (3) purifying and recovering the expressed intact immunoglobulin-format antibody that has cytosol-penetrating ability and specifically recognizes activated (GTP-bound) RAS.

Advantageous Effects

According to the method of the present invention, which allows an intact immunoglobulin-format antibody to penetrate living cells and localize in the cytosol, the antibody can penetrate living cells and localize in the cytosol, without having to use a special external protein delivery system.

Particularly, in order to realize an intact immunoglobulin-format antibody having a stable ability to penetrate the cytosol, the present invention provides a light-chain variable region that easily interacts with and binds to a variety of human heavy-chain variable regions (VHs) and, at the same time, penetrates the cytosol and localizes in the cytosol. An intact immunoglobulin-format antibody comprising this light-chain variable region penetrates cells and localizes in the cytosol, and shows no cytotoxicity nonspecific for cells. When the heavy-chain variable region (VH) of the antibody is replaced with a heavy-chain variable region (VH) capable of specifically recognizing activated (GTP-bound) RAS, the antibody can target activated (GTP-bound) RAS in the cytosol of living cells and inhibit the activity of the RAS.

The use of the cytosol-penetrating intact immunoglobulin-format antibody according to the present invention can penetrate cells and remain in the cytosol, without affecting the high specificity and affinity of a human antibody heavy-chain variable region (VH) for antigens, and thus can localize in the cytosol which is currently classified as a target in disease treatment based on small-molecule drugs, and at the same time, can exhibit high effects on the treatment and diagnosis of tumor and disease-related factors that show structurally complex interactions through a wide and flat surface between protein and protein. In addition, these can selectively inhibit KRas mutants, which are major drug resistance-associated factors in the use of various conventional tumor therapeutic agents, and at the same time, can be used in combination with conventional therapeutic agents to thereby exhibit effective anticancer activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows the results of analysis of a sequence including a clone used in a process of obtaining the improved, cytosol-penetrating humanized light-chain variable single domain hT3 VL (SEQ ID NO: 2), which binds stably to a humanized antibody heavy-chain variable region, from the mouse light-chain variable region m3D8 VL (SEQ ID NO: 18), with sequences also shown for the humanized light-chain variable single domain hT0 VL (SEQ ID NO: 19) and its mutant hT2 VL (SEQ ID NO: 1).

FIG. 2B compares model structures using the WAM modeling of m3D8 VL, the humanized light-chain variable single domain hT0 VL and its mutants (hT2 VL and hT3 VL) by a superimposing method.

FIG. 4A shows the results of analyzing the amino acid sequence of hT3 VL (SEQ ID NO: 2) and its mutant hT4 VL (SEQ ID NO: 3), together with the amino acid sequences of light-chain variable regions (VLs) of conventional human antibody Adalimumab (HUMIRA®) (SEQ ID NO: 20) and humanized antibody Bevacizumab (AVASTIN®) (SEQ ID NO: 21), in order to confirm whether or not hT3 VL can be applied to a variety of human antibody heavy-chain variable regions.

FIG. 4B shows the results of analyzing interface residues between variable regions in order to construct stable cytotransmab that optimally interacts with a human antibody heavy-chain variable region.

BEST MODE FOR CARRYING OUT THE INVENTION

Hereinafter, the present invention will be described in further detail with reference to examples. It will be obvious to a person having ordinary skill in the art that these examples are illustrative purposes only and are not to be construed to limit the scope of the present invention.

Figure 1:
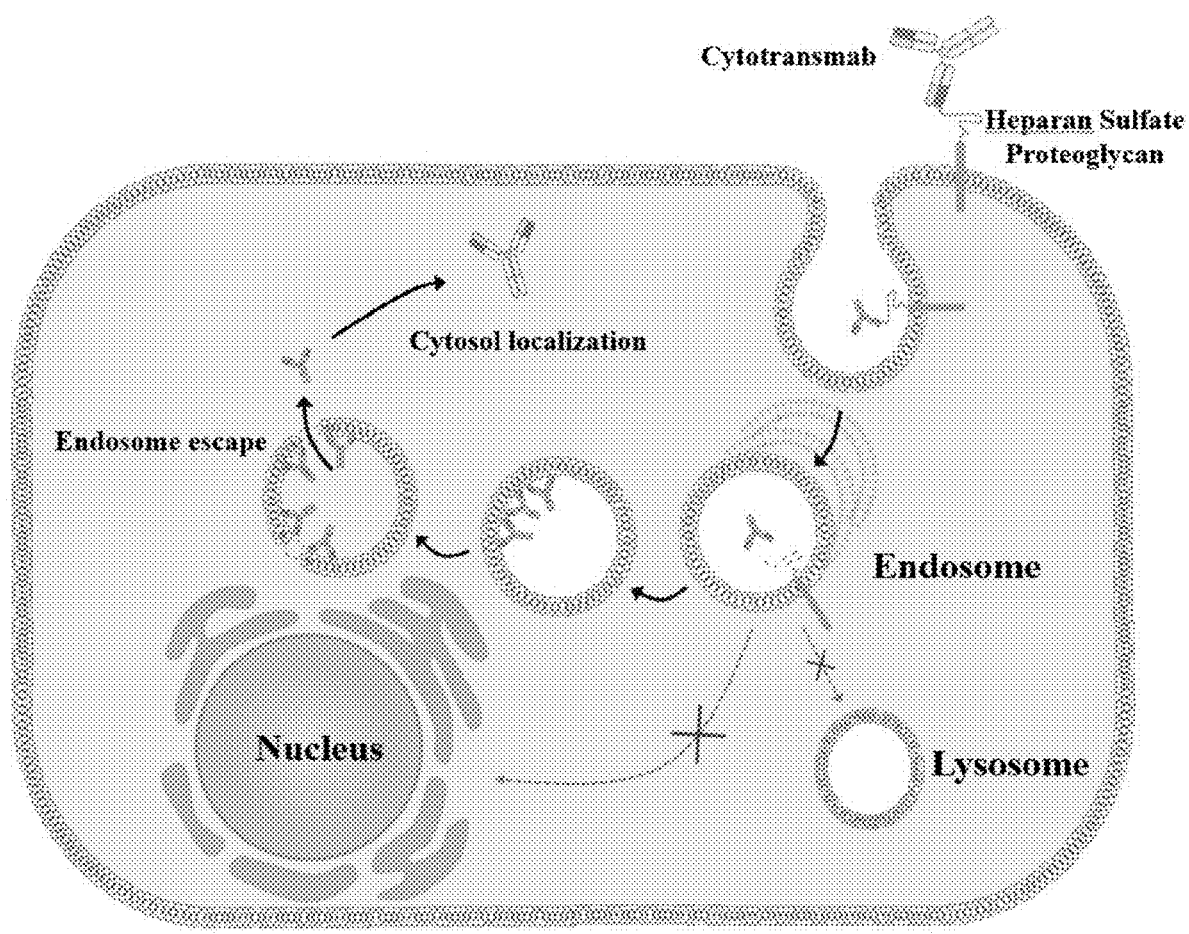
FIG. 1 is a schematic view showing the concept of an intact immunoglobulin-format antibody, named "cytotransmab", which penetrates a cell and localizes in the cytosol.

Example 1: Rationale for Development of Cytosol-Penetrating Humanized Light-Chain Variable (VL) Single Domain FIG. 1 is a schematic view showing the concept of an intact immunoglobulin antibody, named "cytotransmab", which penetrates a cell and localizes in the cytosol. To realize this antibody and understand the cytosol-penetrating ability of humanized antibody light-chain variable regions, reference was made to conventional studies on the correlations between the cytosol-penetrating ability of the mouse light-chain variable single domain m3D8 VL and CDRs corresponding to light-chain variable region fragments (Lee et al., 2013).

FIG. 2A shows the results of analysis of a sequence including a clone used in a process of obtaining the improved, cytosol-penetrating humanized light-chain variable single domain hT3 VL, which binds stably to a humanized antibody heavy-chain variable region, from the mouse light-chain variable region m3D8 VL.

Specifically, based on a comparison of cytosol-penetrating ability between the mouse light-chain variable single domain m3D8 VL and hT0 VL obtained by humanizing the single domain m3D8 VL by use of CDR-grafting technology, it was confirmed that the cytosol-penetrating ability was lost even though the CDR1 sequence of the light-variable variable region (VL) was conserved.

Thus, in order to improve the structure of CDR1 to have a structure similar to that of m3D8 VL to thereby restore the cytosol-penetrating ability of the humanized antibody light-chain variable single domain, CDR regions (Vernier zones) in the FR (framework) were comparatively analyzed. As a result, it was found that residues 2 and 4 differ from those of mouse m3D8 VL having cytosol-penetrating ability. Particularly, because residues 2 and 4 act as an upper core that greatly influence the CDR1 structure (Vernizer zone), hT2 VL having a CDR1 structure similar to that of m3D8 VL was developed by reverse mutations of hT0 VL (see FIG. 2A).

Next, in order to construct stable cytotransmab and to create a pair between VH3 and Vκ1 subgroups (that are highly prevalent in stable antibodies) to thereby develop a light-chain variable region that complementarily stably binds to a variety of human antibody heavy-chain variable regions and retains its ability to penetrate into the cytosol, the FR (framework) of hT2 VL and the light-variable region FR (framework) of the humanized therapeutic monoclonal antibody Trastuzumab (Herceptin), which has VH3 and Vκ1 subgroups and is very stable, were comparatively analyzed. As a result, it was shown that 14 residues in the FR (framework) of hT2 VL differ from those in the light chain-variable region FR (framework) of Trastuzumab. These 14 residues were mutated with the sequence of the light chain-variable region FR (framework) of Trastuzumab, thereby developing hT3 VL (see FIG. 2A).

FIG. 2B compares model structures using the WAM modeling of m3D8 VL, the humanized light-chain variable single domain hT0 VL and its mutants (hT2 VL and hT3 VL) by a superimposing method. It was found that, through reverse mutations at residues 2 and 4 as described above, the structural difference of the CDR1 region from that of m3D8 VL was reduced.

Example 2: Expression and Purification of Humanized Light-Chain Variable (VL) Single Domain Having Cytosol-Penetrating Ability To compare the actual cytosol-penetrating abilities of hT2 VL and hT3 VL designed in the above Example, humanized light-chain variable (VL) single domains were purified.

Specifically, the cytosol-penetrating light-chain variable single domain containing a Pho A signal peptide at the N-terminus and a protein A tag at the C-terminus was cloned into a pIg20 vector by NheI/BamHI restriction enzymes, and then the vector was transformed into E. coli BL21(DE3) plysE for protein expression by electroporation. The E. coli was cultured in LBA medium containing 100 ug/ml of ampicillin at 180 rpm and 37° C. until the absorbance at 600 nm reached 0.6-0.8. Then, the culture was treated with 0.5 mM of IPTG (isopropyl β-D-1-thiogalactopyronoside, and then incubated at 23° for 20 hours to express the protein. After expression, the culture was centrifuged by a high-speed centrifuge at 8,000 rpm for 30 minutes, and the supernatant was collected, and then reacted with IgG-Sepharose resin (GE Healthcare). The resin was washed with 50 ml of TBS (Tris-HCl, 137 mM NaCl, 2.7 mM KCl, pH 7.4), and then washed with 5 ml of 5 mM NH$_4$Ac (pH 5.0) buffer. Next, the protein was eluted from the resin by use of 0.1 M HAc (pH 3.0) buffer, and the buffer was replaced with TBS (pH 7.4) by dialysis. Then, the concentration of the protein was measured by a BCA (bicinchoninic acid (Pierce)) assay, and the purity of the protein was analyzed by SDS-PAGE.

Example 3: Verification of Cytosol-Penetrating Ability and Cell Penetration Mechanism of Cytosol-Penetrating Humanized Light-Chain Variable (VL) Single Domain FIG. 3A shows the results of confocal microscopy observation of the cytosol-penetrating ability of light-chain variable single domains.

Specifically, in order to verify the cytosol-penetrating abilities of m3D8 VL, hT0 VL, hT2 VL and hT3 VL, a cover slip was added to 24-well plates, and 5×10$^4$ HeLa cells per well were added to 0.5 ml of 10% FBS (Fetal bovine Serum)-containing medium and cultured for 12 hours under the conditions of 5% CO$_2$ and 37° C. When the cells were stabilized, each well was treated with 10 μM of m3D8 VL, hT0 VL, hT2 VL or hT3 VL in 0.5 ml of fresh medium, and incubated for 6 hours under the conditions of 37° C. and 5% CO$_2$. Next, the medium was removed, and each well was washed with PBS, and then treated with a weakly acidic solution (200 mM glycine, 150 mM NaCl, pH 2.5) to remove proteins from the cell surface. Next, each well was washed with PBS, and the cells were fixed in 4% paraformaldehyde at 25° C. for 10 minutes. After washing with PBS, each well was incubated with PBS buffer containing 0.1% saponin, 0.1% sodium azide and 1% BSA at 25° C. for 10 minutes to form pores in the cell membranes. After washing with PBS, each well was incubated with PBS buffer c containing 2% BSA at 25° C. for 1 hour to eliminate nonspecific binding. Then, each well was treated with rabbit-IgG (Sigma) that recognizes the protein A tag of the light-chain variable single domain, and each well was incubated at 25° C. for 2 hours, washed three times with PBS, and then treated with red fluorescence (TRITC)-labeled anti-rabbit antibody (Sigma), followed by incubation at 25° C. for 1 hour. Finally, the nucleus was blue-stained with Hoechst33342 and observed with a confocal microscope. As a result, it was shown that m3D8 VL, hT2 VL and hT3 VL, except for hT0 VL, had cell-penetrating ability.

Figure 3A:
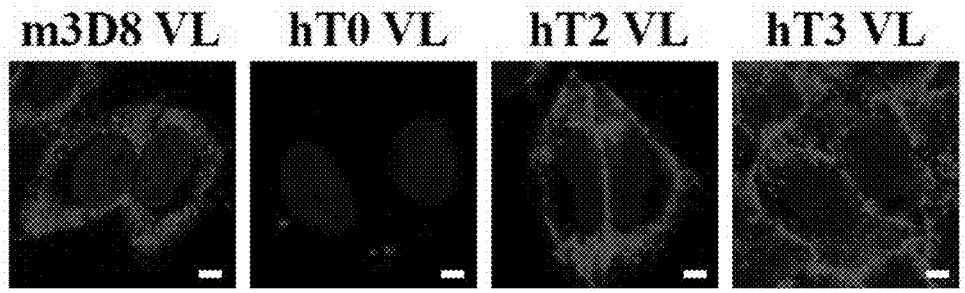
FIG. 3A shows the results of confocal microscopy observation of the cytosol-penetrating ability of light-chain variable single domains.
Figure 3B:
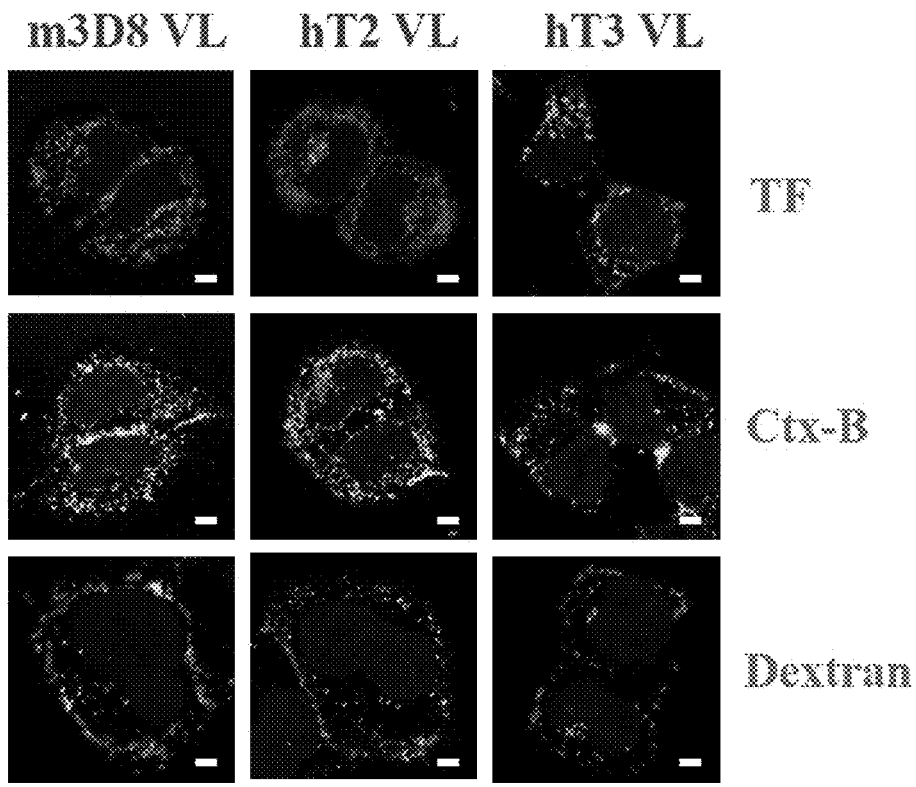
FIG. 3B shows the results of confocal microscopy observation performed to verify the cytosol-penetrating mechanisms of light-chain variable single domains.

FIG. 3B shows the results of confocal microscopy observation performed to verify the cytosol-penetrating mechanisms of light-chain variable single domains.

Specifically, when HeLa cells were prepared as shown in FIG. 3A and stabilized, a dilution of 10 μM of m3D8 VL, hT2 VL or hT3 VL and 10 ug/ml of Alexa Fluor 488-transferrin (TF, green fluorescence), FITC-cholera toxin B (Ctx-B, green fluorescence) or Oregon green-dextran (Dextran, green fluorescence) in 0.5 ml of fresh medium was added to each well and incubated for 2 hours under the conditions of 37° C. and 5% CO$_2$. Next, the light-chain variable single domains were stained as shown in FIG. 3A.

As shown in FIG. 3B, all the light-chain variable single domains were superimposed with cholera toxin-B, indicating that these domains penetrate the cytosol by caveolae.

Example 4: Development of Cytosol-Penetrating Humanized Light-Chain Variable (VL)

Single Domain That Easily Interacts with Human Antibody Heavy-Chain Variable Domain FIG. 4A shows the results of analyzing the amino acid sequence of hT3 VL together with the amino acid sequences of light-chain variable domains (VLs) of conventional human antibody Adalimumab (HUMIRA®) and humanized antibody Bevacizumab (AVASTIN®) in order to confirm whether or not hT3 VL can be applied to a variety of human antibody heavy-chain variable domains.

Specifically, VH-VL interface residues that are involved in the interaction between heavy-chain and light-chain variable domains were analyzed. As a result, it was found that lysine (K) at position 89 and serine (S) at position 91 of the CDR3 of the VL domain are consistent with glutamine (Q) at position 89 and tyrosine (Y) in human antibodies.

To construct a strategy for improving the residues, the effects of VH-VL interface residues on the CDRs of the heavy-chain variable domain and the light-chain variable region were analyzed in more detail.

FIG. 4B shows the results of analyzing interface residues between variable regions in order to construct stable cytotransmab that optimally interacts with a human antibody heavy-chain variable region.

Specifically, based on information about the positions of interface residues between human antibody variable regions, the frequency of binding to specific interface residues located in opposite variable regions, and the abundance of interface residues in human antibodies, which were reported in the literature, hT3 VL and the interface residues between the heavy chain and light chain variable regions of Bevacizumab (AVASTIN®) and Adalimumab (HUMIRA®), which are antibodies approved by the FDA, were analyzed (Vargas-Madrazo and Paz-Garcia, 2003). The results of the analysis indicated that, in the mouse CDRs of hT3 VL, residues 89 and 91 in CDR3 that is involved in association between variable regions are highly abundant in human antibodies and can influence the CDR3 structure of the heavy-chain variable region (VH). The two residues were mutated with amino acids that are highly abundant in human antibodies, thereby hT4 VL that can optimally bind to human antibody heavy-chain variable regions.

Tables 1 and 2 below show the sequences of the designed human antibody light-chain variable regions having cytosol-penetrating ability. Table 1 shows the full-length sequences of the human antibody light-chain variable regions, numbered according to the Kabat numbering system, and Table 2 shows the CDR sequences of the antibody sequences shown in Table 1.

TABLE 1

Full-length seqeunces of cytosol-penetrating human antibody light-chain variable

| Names of light chain variable regions | Sequences | SEQ ID NOS: |
|---|---|---|
| hT2 VL | 1           10          20       abcdef  30          40            50<br>DLVMTQSPATLSLSPGERATLSCKSSQSLFNSRTRKNYLAWYQQKPGQAPRLLIYW<br>             60          70          80          90         100<br>ASTRESGIPGRFSGSGSGTDFTLTISSLEPEDFAVYYCKQSYYHMYTFGQGTKVEIKR | SEQ ID NO: 1 |

TABLE 1-continued

Full-length seqeunces of cytosol-penetrating human antibody light-chain variable

| Names of light chain variable regions | Sequences | SEQ ID NOS: |
|---|---|---|
| hT3 VL | ```
         1         10        20    abcdef  30        40        50
         DLVMTQSPSSLSASVGDRVTITCKSSQSLFNSRTRKNYLAWYQQKPGKAPKLLIYW
                   60        70        80        90       100
         ASTRESGVPSRFSGSGSGTDFTLTISSLQPEDFATYYCKQSYYHMYTFGQGTKVEIKR
``` | SEQ ID NO: 2 |
| hT4 VL | ```
         1         10        20    abcdef  30        40        50
         DLVMTQSPSSLSASVGDRVTITCKSSQSLFNSRTRKNYLAWYQQKPGKAPKLLIYW
                   60        70        80        90       100
         ASTRESGVPSRFSGSGSGTDFTLTISSLQPEDFATYYCKQSYYHMYTFGQGTKVEIKR
``` | SEQ ID NO: 3 |

TABLE 2

CDR sequences of cytosol-penetrating human antibody light-chain variable regions.

| Names of light chain variables regions Kabat No. | 24 | 25 | 26 | 27 | 27a | 27b | 27c | 27d | 27e | 27f | 28 | 29 | 30 | 31 | 32 | 33 | 34 | SEQ ID NO: | 50 | 51 | 52 | 53 | 54 | 55 | 56 | SEQ ID NO: |
|---|---|---|---|---|---|---|---|---|---|---|---|---|---|---|---|---|---|---|---|---|---|---|---|---|---|---|
| | | | | | CDR1 Sequence | | | | | | | | | | | | | | | | | CDR2 Sequence | | | | |
| hT2 VL | K | S | S | Q | S | L | F | N | S | R | T | R | K | N | Y | L | A | 4 | W | A | S | T | R | E | S | 5 |
| hT3 VL | K | S | S | Q | S | L | F | N | S | R | T | R | K | N | Y | L | A | 7 | W | A | S | T | R | E | S | 8 |
| hT4 VL | K | S | S | Q | S | L | F | N | S | R | T | R | K | N | Y | L | A | 10 | W | A | S | T | R | E | S | 11 |

| Names of light chain variables regions Kabat No. | 89 | 90 | 91 | 92 | 93 | 94 | 95 | 96 | 97 | SEQ ID NO: |
|---|---|---|---|---|---|---|---|---|---|---|
| | | | | CDR3 Sequence | | | | | | |
| hT2 VL | K | Q | S | Y | Y | H | W | Y | T | 6 |
| hT3 VL | K | Q | S | Y | Y | H | W | Y | T | 9 |
| hT4 VL | Q | Q | Y | Y | Y | H | W | Y | T | 12 |

Figure 5:
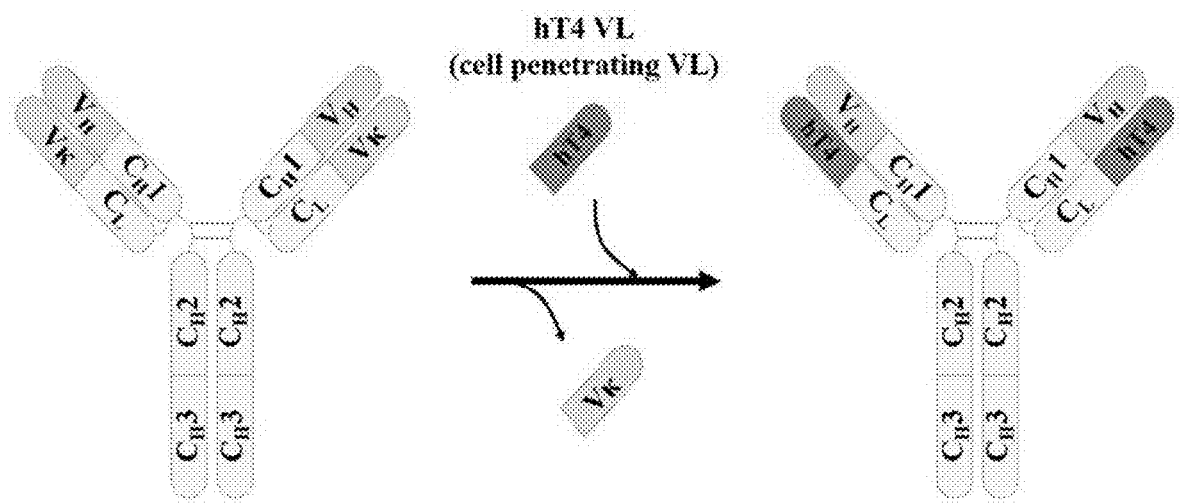
FIG. 5 is a schematic view showing a method of substituting a light-chain variable region having no cell-penetrating ability with a humanized light-chain variable region having cytosol-penetrating ability in order to construct cytotransmab.

Example 5: Development of Cytotransmab by Substitution with Cytosol-Penetrating Humanized Light-Chain Region (VL), and Expression and Purification of Cytotransmab FIG. 5 is a schematic view showing a method of substituting a light-chain variable region having no cell-penetrating ability with a humanized light-chain variable region having cytosol-penetrating ability in order to construct cytotransmab.

Specifically, in order to construct a heavy-chain expression vector for producing an intact IgG-format monoclonal antibody, a DNA encoding a heavy chain comprising an antibody heavy-chain variable region (Bevacizumab VH, Adalimumab VH, or humanized hT0 VH) and a heavy-chain constant region (CH1-hinge-CH2-CH3), which has a secretion signal peptide-encoding DNA fused to the 5' end, was cloned into a pcDNA3.4 vector (Invitrogen) by NotI/HindIII. Furthermore, in order to construct a vector that expresses a light chain, a DNA encoding either a cytosol-penetrating light-chain variable region (hT4 VL) or the light-chain variable region (Bevacizumab VL, or Adalimumab VL) and light-chain constant region (CL) of a model antibody, which a secretion signal peptide-encoding DNA fused to the 5' end, was cloned into a pcDNA3.4 vector (Invitrogen) by use of NotI/HindIII.

The light-chain and heavy-chain expression vectors were transiently transfected, and the proteins were expressed and purified, followed by comparison of the yield of the proteins. In a shaking flask, HEK293-F cells (Invitrogen) suspension-growing in serum-free Free Style 293 expression medium (Invitrogen) were transfected with a mixture of plasmid and polyethylenimine (PEI) (Polyscience). After 200 mL transfection in a shaking flask (Corning), HEK293-F cells were seeded into 100 ml of medium at a density of $2.0 \times 10^6$ cells/ml, and cultured at 150 rpm and in 8% $CO_2$. To produce each monoclonal antibody, a suitable heavy-chain and light-chain plasmid were diluted in 10 ml of FreeStyle 293 expression medium (Invitrogen) (125 µg heavy chain, 125 µg light chain, a total of 250 µg (2.5 µg/ml)), and the dilution was mixed with 10 ml of medium containing 750 µg (7.5 µg/ml) of PEI, and the mixture was incubated at room temperature for 10 minutes. The incubate medium mixture was added to 100 ml of the seeded cell culture which was then cultured at 150 rpm in 8% $CO_2$ for 4 hours, after which 100 ml of Free Style 293 expression was added to the cell culture, followed by culture for 6 days. In accordance with the standard protocol, the protein was purified from the collected cell culture supernatant. The antibody was applied to a Protein A Sepharose column (GE Healthcare), and washed with PBS (pH 7.4). The antibody was eluted using 0.1 M glycine buffer (pH 3.0), and then immediately neutralized with 1M Tris buffer. The eluted antibody fraction was concentrated while the buffer was replaced with PBS (pH 7.4) by dialysis. The purified protein was quantified by measuring the absorbance at 280 nm and the absorption coefficient.

Table 3 below shows the yields of purified cytotransmabs and proteins produced per liter of culture volume. Three measurements were statistically processed, and ± indicates standard deviation values. With respect to the yields of the obtained proteins, cytotransmabs, including hT4 VL improved to facilitate its interaction with a human heavy-chain variable region (VH), did not greatly differ from the wild-type monoclonal antibodies.

TABLE 3

Comparison of the purification yields of Cytotransmabs with those of wild-type IgG-format monoclonal antibodies (Adalimumab, and Bevacizumab)

| IgG clone | VH | VL | IgG purification yield (mg/1-liter of transfected cells) |
| --- | --- | --- | --- |
| TMab2 | h3D8 VH | hT2 VL | 8.0 ± 0.7 |
| TMab3 | h3D8 VH | hT3 VL | 8.2 ± 0.5 |
| TMab4 | h3D8 VH | hT4 VL | 10.8 ± 1.0 |
| Adalimumab | Adalimumab VH | Adalimumab VL | 11.6 ± 0.3 |
| HuT2 | Adalimumab VH | hT2 VL | 2.1 ± 0.6 |
| HuT3 | Adalimumab VH | hT3 VL | 3.5 ± 0.8 |
| HuT4 | Adalimumab VH | hT4 VL | 10.9 ± 0.8 |
| Bevacizumab | Bevacizumab VH | Bevacizumab VL | 8.8 ± 0.4 |
| AvaT4 | Bevacizumab VH | hT4 VL | 8.0 ± 1.1 |

These results indicate that the humanized light-chain variable region (hT4 VL) obtained by additionally modifying interface residues can optimally interact with a humanized antibody heavy-chain variable region, and thus can be stably expressed and purified.

Figure 6A:
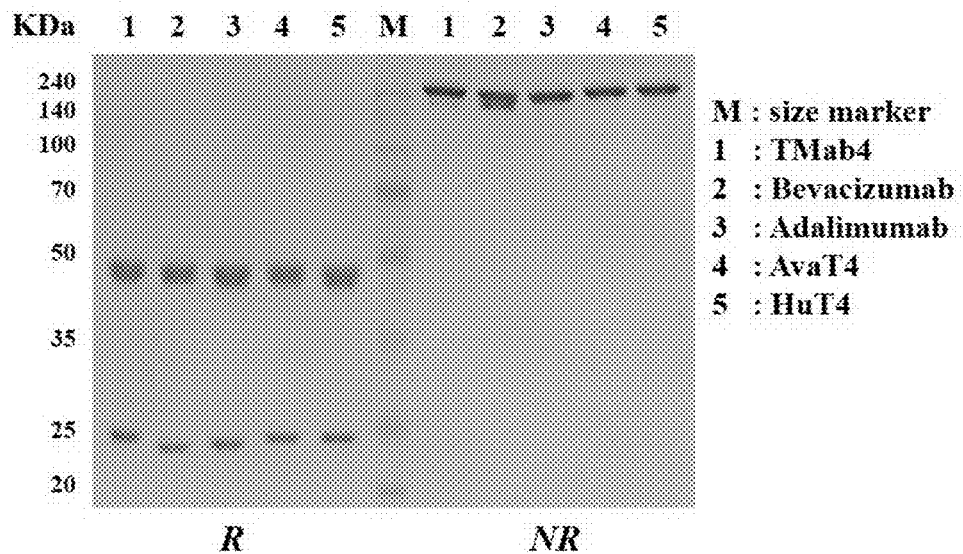
FIG. 6A shows the results of analyzing cytotransmab by reductive or non-reductive SDS-PAGE after purification.

FIG. 6A shows the results of analyzing cytotransmab by reductive or non-reductive SDS-PAGE after purification.

Specifically, in a non-reductive condition, a molecular weight of about 150 kDa appeared, and in a reductive condition, the heavy chain showed a molecular weight of about 50 kDa, and the light-chain showed a molecular weight of about 25 kDa. This suggests that the purified cytotransmab and monoclonal antibodies are present as monomers in a solution state, and do not form a dimer or an oligomer by a non-natural disulfide bond.

Figure 6B:
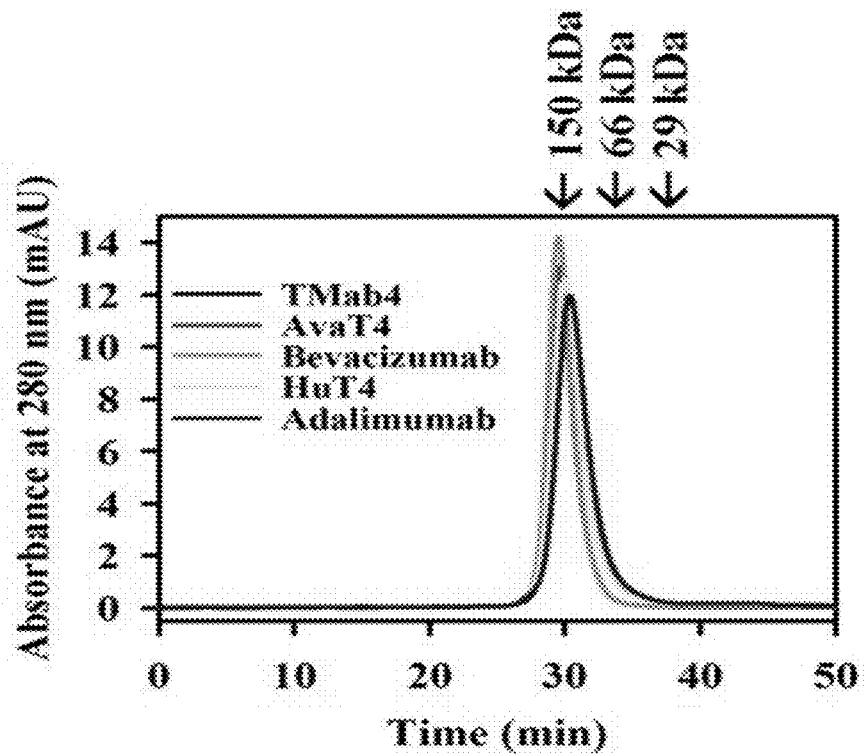
FIG. 6B shows the results of an experiment performed using a size exclusion chromatography column (Superdex™200 10/300GC) (GE Healthcare) by HPLC (high performance liquid chromatography) (The Agilent 1200 Series LC systems and Modules) (Agilent) in order to confirm that cytotransmab is present as a monomer in a natural environment.

FIG. 6B shows the results of an experiment performed using a size exclusion chromatography column (Superdex™200 10/300GC) (GE Healthcare) by HPLC (high performance liquid chromatography) (The Agilent 1200 Series LC systems and Modules) (Agilent) in order to confirm that cytotransmab is present as a monomer in a natural environment.

Specifically, high-salt elution buffer (12 mM phosphate, pH 7.4, 500 mM NaCl, 2.7 mM KCl) (SIGMA) was used at a flow rate of 0.5 ml/min in order to eliminate the nonspecific binding to resin caused by electrical attraction due to basic residues. The proteins used as protein size markers were dehydrogenase (150 kDa), albumin (66 kDa), and carbonic anhydrase (29 kDa). A single extreme point was measured in all the monoclonal antibodies and cytotransmab, indicating that these antibodies are present as monomers.

Example 6: Analysis of Affinity of Heavy-Chain Variable Region of Cytotransmab and Analysis of DNA Hydrolysis Ability of Light-Chain Variable Region (VL)

Figure 6C:
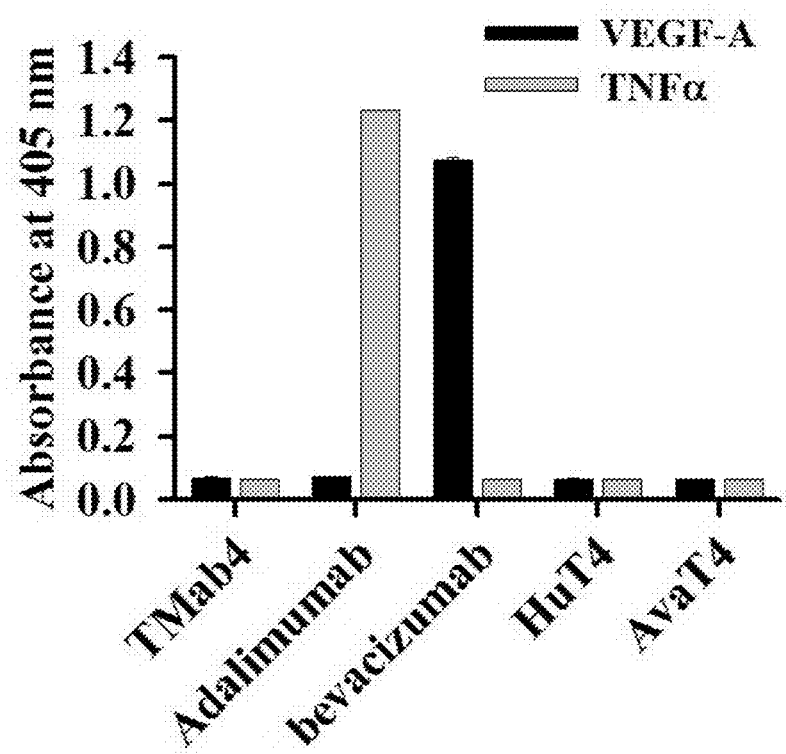
FIG. 6C shows the results of ELISA (enzyme linked immunosorbent assay) performed to measure the affinities of the heavy-chain variable regions of cytotransmab (TMab4, HuT4 or AvaT4) and IgG antibodies (Bevacizumab (AVASTIN®) and Adalimumab (HUMIRA®)) for target molecules.

FIG. 6C shows the results of ELISA (enzyme linked immunosorbent assay) performed to measure the affinities of the heavy-chain variable regions of cytotransmab (TMab4, HuT4 or AvaT4) and monoclonal antibodies (Bevacizumab (AVASTIN®) and Adalimumab (HUMIRA®)) for target molecules.

Specifically, a target molecule (VEGF-A, or TNF-α) was incubated in a 96-well EIA/RIA plate (COSTAR Corning) at 37° C. for 1 hour, and then washed three times with 0.1% PBST PBST (0.1% Tween20, pH 7.4, 137 mM NaCl, 12 mM phosphate, 2.7 mM KCl) (SIGMA) for 10 minutes. After incubation with 5% PBSS PBSS (5% Skim milk, pH 7.4, 137 mM NaCl, 12 mM phosphate, 2.7 mM KCl) (SIGMA) for 1 hour, the target molecule was washed three times with 0.1% PBST for 10 minutes. Next, each of cytotransmab and monoclonal antibodies (TMab4, Bevacizumab, Adalimumab, AvaT4, and HuT4) was bound to the target molecule, followed by washing three times with 0.1% PBST for 10 minutes. As a marker antigen, goat alkaline phosphatase-conjugated anti-human mAb (SIGMA) was used. Each of the resulting material was reacted with pNPP (p-nitrophenyl palmitate) (SIGMA), and the absorbance at 405 nm was measured.

As shown in FIG. 6C, AvaT4 and HuT4 lost their affinity for the target molecule. In the case of Adalimumab and TNF-α, it was shown that the antigen recognition site was involved in all the CDRs located in the heavy chain and the light chain (Shi et al., 2013). In the case of Bevacizumab, it was found that the CDR3 of the heavy-chain variable region (VH) plays an important role in binding to antigen, but the analysis results shown in FIG. 8B indicated that Bevacizumab has the VH7 subgroup. In addition, it was found that residue 96 of the light-chain variable region of Bevacizumab, which greatly influences the heavy-chain variable region (VH) CDR3, did greatly differ from that of hT4 VL (Charlotte et al., 2007).

Figure 6D:
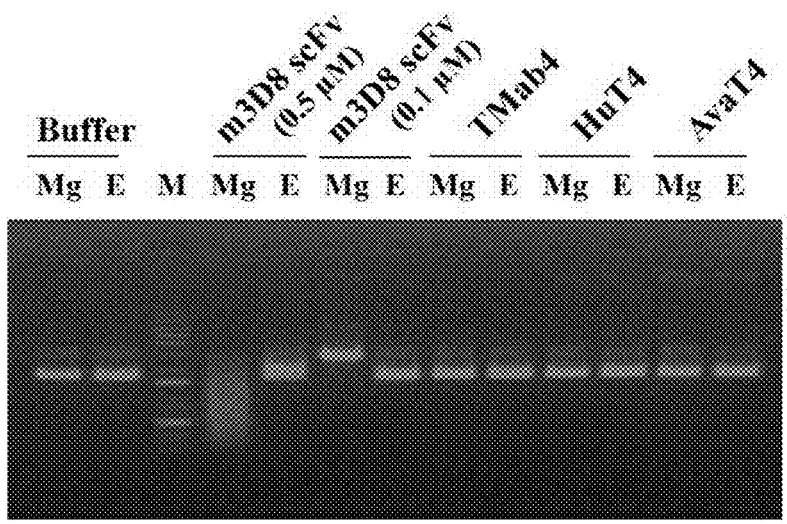
FIG. 6D shows the results of an agarose gel nucleic acid hydrolysis experiment performed to examine the hydrolysis of nucleic acids in cytotransmab obtained by substitution with a cell-penetrating human light-chain variable region (hT4) grafted with the CDR of an autoimmune mouse antibody.

FIG. 6D shows the results of an agarose gel nucleic acid hydrolysis experiment performed to examine the hydrolysis of nucleic acids in cytotransmab obtained by replacement with a cell-penetrating human light-chain variable region (hT4) grafted with the CDR of an autoimmune mouse antibody.

Specifically, in a total mixture volume of 10 µl, a purified pUC19 substrate (2.2 nM) and either m3D8 scFv protein (0.5 µM and 0.1 µM) known to have the ability to hydrolyze nucleic acids, or each of cytotransmab and monoclonal antibodies (TMab4, AvaT4, HuT4 (0.1 µM)), were incubated in TBS reaction buffer (50 mM Tris-HCl, 50 mM NaCl, pH 7.4) (SIGMA). Herein, the TBS buffer contained 2 mM $MgCl_2$, and another buffer contained 50 mM EDTA (SIGMA) and was used as a control. The prepared samples were incubated at 37° C. After 1 hour, the samples were observed.

As shown in FIG. 6D, the results of the observation indicated that TMab4, AvaT4 and HuT4 had no nucleic acid-hydrolyzing ability at 0.1 µM. This suggests that when these antibodies penetrate the cytosol and remain in the cytosol, they no cause nonspecific cytotoxicity.

Example 7: Verification of Cytosol-Penetrating Abilities of Cytotransmab

Figure 7A:
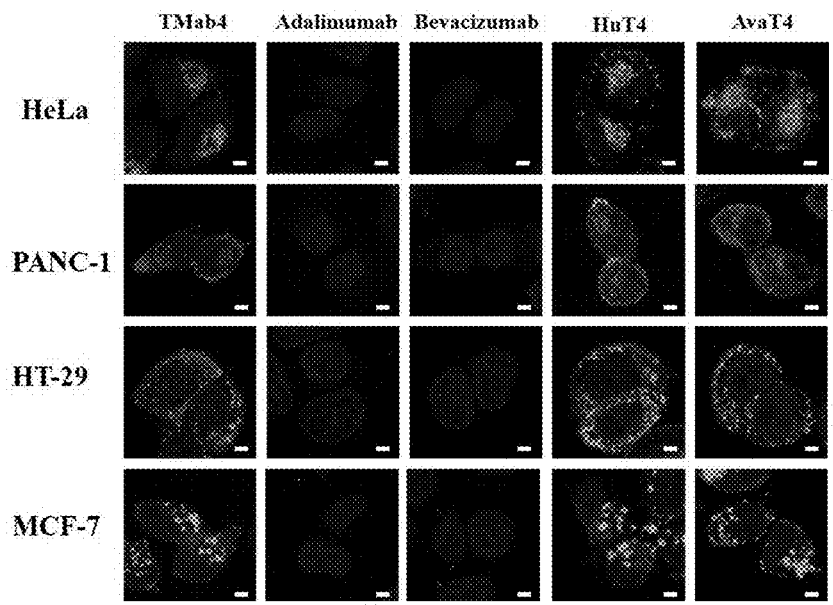
FIG. 7A shows the results of observing 1-2 cells in various cell lines by confocal microscopy in order to verify the cytosol-penetrating ability of cytotransmabs having a light-chain variable region substituted with the cytosol-penetrating light-chain region hT4 VL.

FIG. 7A shows the results of observing 1-2 cells in various cell lines by confocal microscopy in order to verify the cytosol-penetrating abilities of cytotransmabs having a light-chain variable region replaced with the cytosol-penetrating light-chain region hT4 VL.

Specifically, in a 24-well plate, $5 \times 10^4$ HeLa, PANC-1, HT29 or MCF-7 cells per well were added to 0.5 ml of 10% FBS-containing medium, and cultured for 12 hours under the conditions of 5% $CO_2$ and 37° C. When the cells were stabilized, each well was incubated with a dilution of each of 1 µM of TMab4, Adalimumab (HUMIRA®), Bevacizumab (AVASTIN®), HuT4 or AvaT4 in 0.5 ml of fresh medium for 6 hours under the conditions of 37° C. and 5% $CO_2$. Next, the medium was removed, and each well was washed with PBS, and then treated with a weakly acidic solution (200 mM glycine, 150 mM NaCl (pH 2.5)) to remove proteins from the cell surface. After washing with PBS, the cells were fixed in 4% paraformaldehyde at 25° C. for 10 minutes. Next, each well was washed with PBS, and incubated with PBS buffer containing 0.1% saponin, 0.1% sodium azide and 1% BSA at 25° C. for 10 minutes to pores in the cell membranes. Next, each well was washed with PBS, and then incubated with PBS buffer containing 2% BSA at 25° C. for 1 hour in order to eliminate nonspecific binding. Thereafter, each well was incubated with FITC (green fluorescence)-labeled antibody (Sigma), which specifically recognizes human Fc, at 25° C. for 1.5 hours, and the nucleus was blue-stained with Hoechst33342, and observed with a confocal microscope. Unlike IgG-format monoclonal antibodies (Adalimumab and Bevacizumab) which target extracellularly secreted proteins, TMab4, HuT4 and AvaT4 showed green fluorescence in the cells.

Figure 7B:
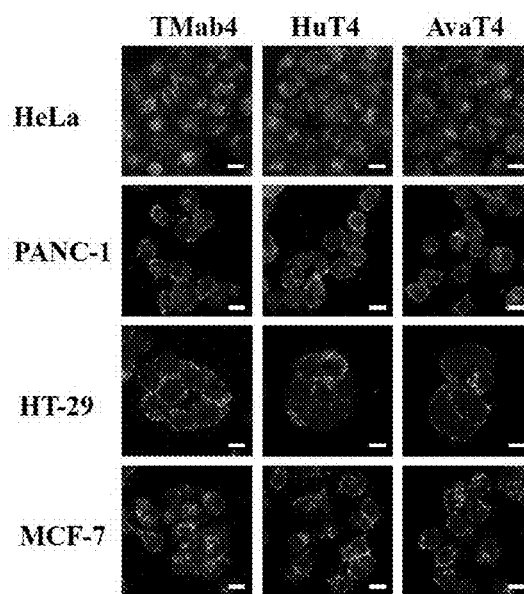
FIG. 7B shows the results of examining cytosol-penetrating ability for several cells, performed at a reduced magnification in order to examine cell-penetrating efficiency in the cytosol-penetrating ability examination experiment by confocal microscopy observation as shown in FIG. 7A.

FIG. 7B shows the results of examining cytosol-penetrating ability for several cells, performed at a reduced magnification in order to examine cell-penetrating efficiency in the cytosol-penetrating ability examination experiment by confocal microscopy observation as shown in FIG. 7A.

It was shown that the cytotransmab introduced with the cytosol-penetrating humanized light-chain variable region penetrated the cytosol of all the cells and localized in the cytosol.

Figure 8A:
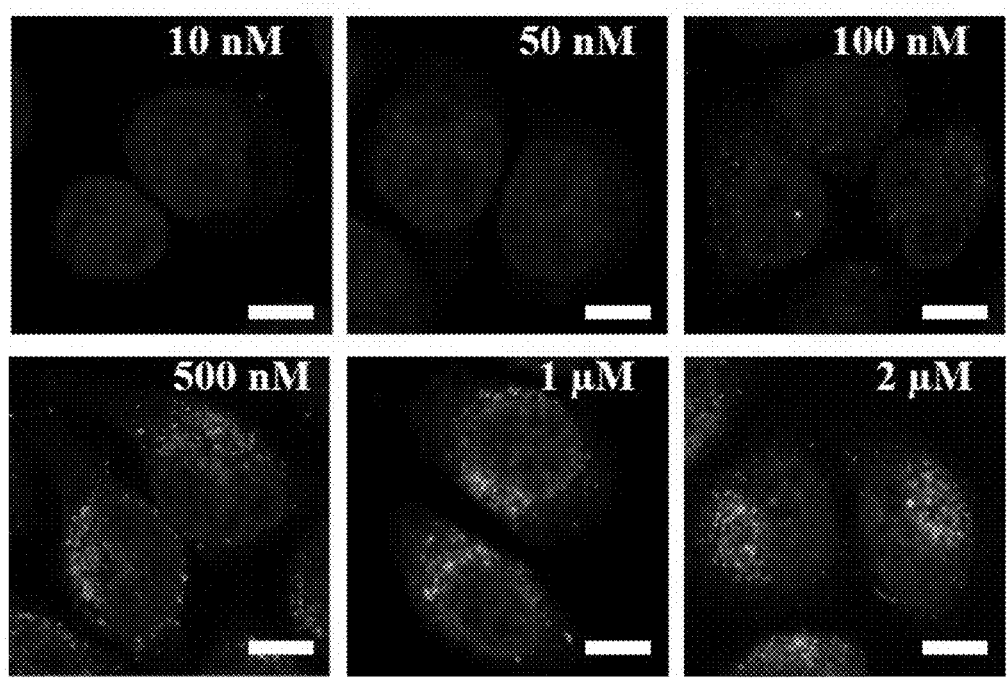
FIG. 8A shows the results of observing the degree of cell penetration of TMab4 as a function of the concentration of TMab4 by confocal microscopy.

FIG. 8A shows the results of observing the degree of cell penetration of TMab4 as a function of the concentration of TMab4 by confocal microscopy. HeLa cells were treated with 10 nM, 50 nM, 100 nM, 500 nM, 1 µM and 2 µM of TMab4, and cultured at 37° C. for 6 hours. In the same manner as described above, the cells were observed with a confocal microscope. When TMab4 was incubated for 6 hours, green fluorescence was observed in the cells, starting from a concentration of 100 nM. As the concentration increased from 100 nM, green fluorescence in the cells increased.

Figure 8B:
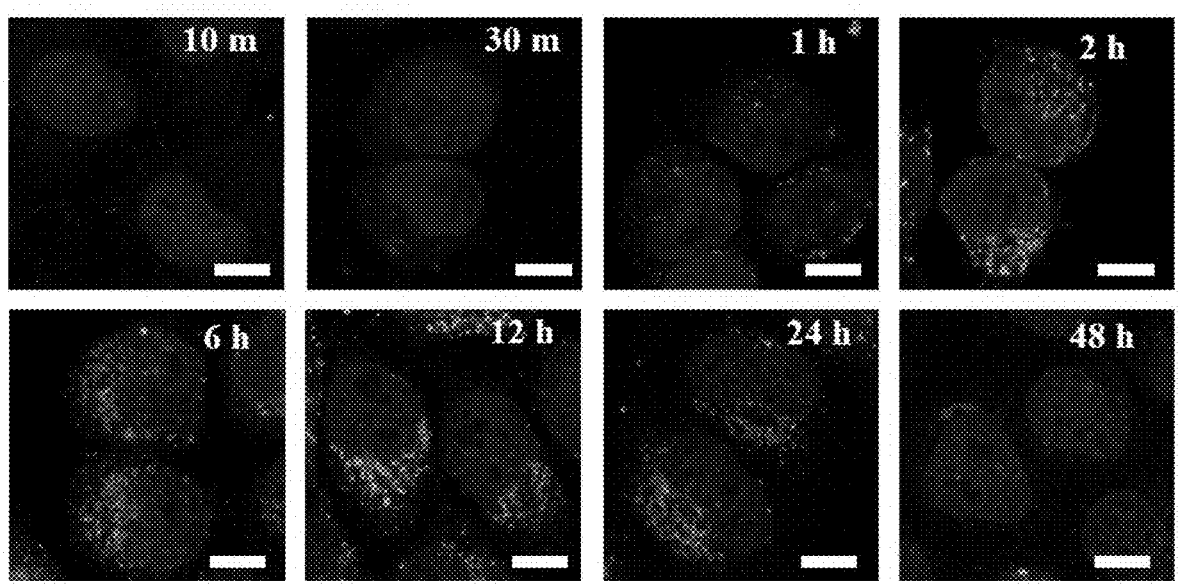
FIG. 8B shows the results of observing the degree of cell penetration of TMab4 as a function of time after TMab4 treatment by confocal microscopy.

FIG. 8B shows the results of observing the degree of cell penetration of TMab4 as a function of time after TMab4 treatment by confocal microscopy. HeLa cells were treated with 1 µM of TMab4, and then cultured at 37° C. for 10 min, 30 min, 1 hour, 2 hours, 6 hours, 12 hours 24 hours and 48 hours. The cultured cells were stained in the same manner as described in the above Example, and were observed with a confocal microscope.

Starting from 30 minutes, TMab4 showed weak green fluorescence in the cells. The green fluorescence gradually increased, and was the strongest at 6 hours. Thereafter, the fluorescence gradually decreased, and became very weak at 48 hours.

Example 8: Evaluation of Cytotoxicity of Cytotransmabs

In order to examine whether or not the cytotransmabs confirmed to have cytosol-penetrating ability in Example 7 would have cytotoxicity in vitro, HeLa or PANC-1 cells were treated with each of TMab4, HuT4, Adalimumab, AvaT4 and Bevacizumab, and the inhibition of growth of the cells was examined by an MTT assay (Sigma).

Specifically, in a 96-well plate, $1 \times 10^4$ HeLa or PANC-1 cells per well were cultured in 0.1 ml of 10% FBS-containing medium for 12 hours under the conditions of 37° C. and 5% $CO_2$. Then, each well was treated with 1 µM of each of TMab4, HuT4, Adalimumab, AvaT4 and Bevacizumab for 20 hours or 44 hours, and then 20 µl of MTT solution (1 mg/ml PBS) was added to each well, followed by incubation for 4 hours. The formed formazan was dissolved in 200 µl of DMSO (dimethyl sulfoxide), and the absorbance at 595 nm was measured to determine cell viability.

Figure 9A:
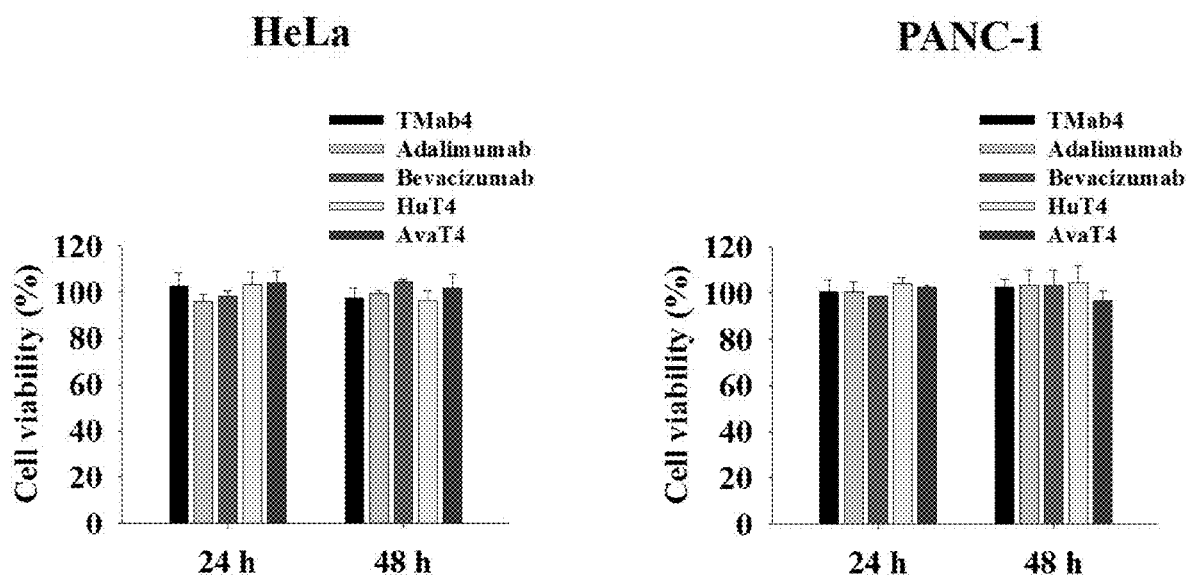
FIG. 9A is a graph showing the results obtained by treating HeLa and PANC-1 cell lines with cytotransmab and evaluating the inhibition of growth of the cells in vitro.
Figure 9B:
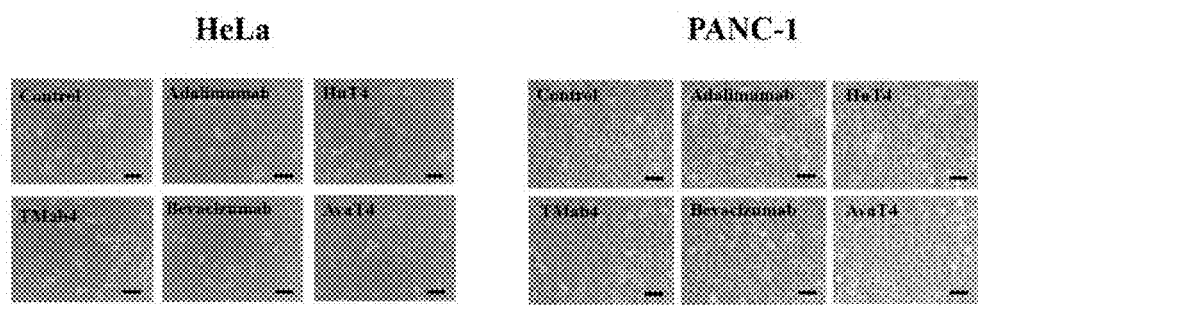
FIG. 9B is an image showing the results obtained by treating HeLa and PANC-1 cell lines with cytotransmab and evaluating the inhibition of growth of the cells in vitro.

FIG. 9A is a graph showing the results obtained by treating HeLa and PANC-1 cell lines with cytotransmab and evaluating the inhibition of growth of the cells in vitro. FIG. 9B is an image showing the results obtained by treating HeLa and PANC-1 cell lines with cytotransmab and evaluating the degree of inhibition of the cells in vitro. As shown in FIGS. 9A and 9B, all the antibodies showed no cytotoxicity. As shown in Example 6 above, cytotransmabs had no nucleic acid-hydrolyzing ability, unlike m3D8 scFv, and thus had no cytotoxicity.

Figure 10:
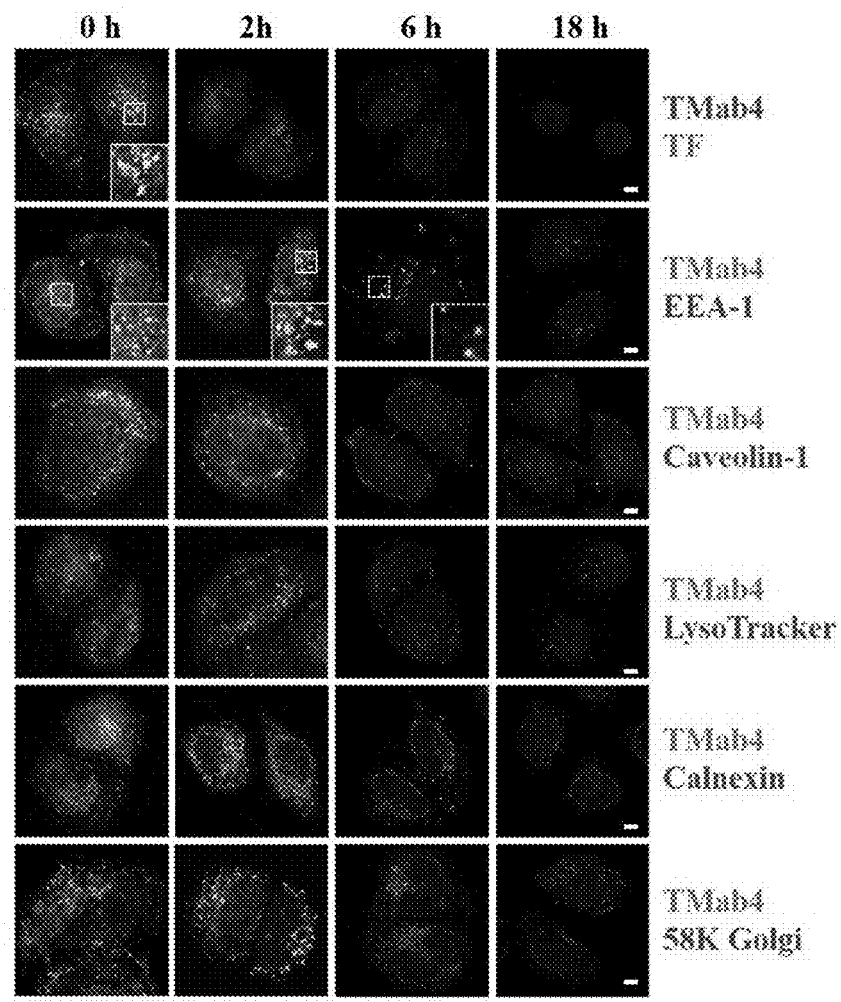
FIG. 10 shows the results of observing the transport and stability of intracellularly introduced TMab4 by pulse-chase and confocal microscopy.

Example 9: Verification of Intracellular Transport and Degradation Mechanisms of Cytotransmab FIG. 10 shows the results of observing the transport and stability of intracellularly introduced TMab4 by pulse-chase and confocal microscopy.

Specifically, HeLa cells were prepared in the same manner as described above. The prepared cells were treated with 3 μM of TMab4 at 37° C. for 30 minutes, and then washed quickly three times with PBS, and cultured in medium at 37° C. for 2 hours, 6 hours and 18 hours. The cells were washed with PBS and a weakly acidic solution in the same manner as described in the above Example, and then subjected to cell fixation, cell perforation and blocking processes. TMab4 was stained with green fluorescence (FITC) or red fluorescence (TRITC)-labeled antibody that specifically recognizes human Fc. Furthermore, the cells were incubated with anti-EEA1 antibody against the early endosome marker EEA1 (Early Endosome Antigen1), anti-caveolin-1 antibody against the caveosome marker caveolin-1, anti-calnexin antibody against the endoplasmic reticulum marker calnexin, or anti-58K Golgi antibody (Santa Cruz) against the Golgi marker 58K Golgi protein, at 4° C. for 12 hours, and incubated with red fluorescence (TRITC)-labeled secondary antibody at 25° C. for 1 hour. At 30 minutes before cell fixation, the cells being cultured were treated directly with 1 μM of LysoTracker® Red DND-99 or 10 μg/ml of Alexa Fluor 488-transferrin. After the staining process, the cells were analyzed with a confocal microscope. As a result, TMab4 was more stable in the cells than transferrin, and penetrated into the cytosol by clathrin and localized in the early endosome up to 2 hours, after which it was not transported into the lysosome and not superimposed with any organelle.

Figure 11A:
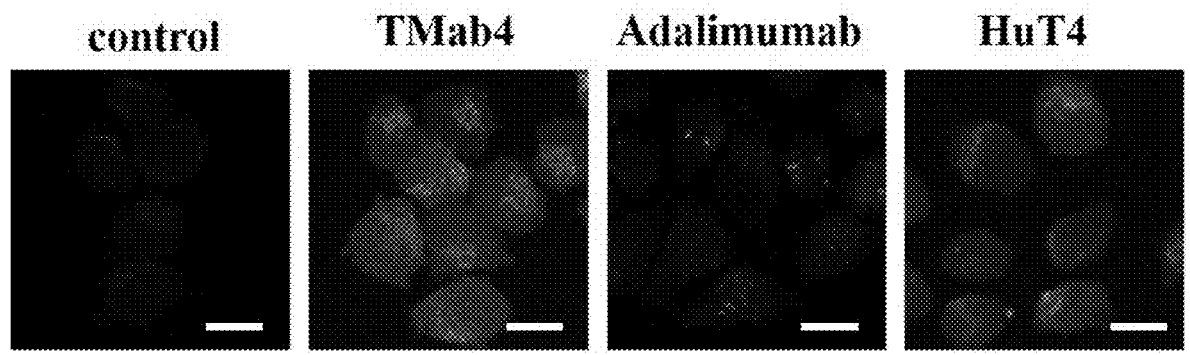
FIG. 11A shows the results of confocal microscopy observation performed using calcein to indirectly confirm the cytosolic localization of cytotransmab TMab4 or HuT4.

FIG. 11A shows the results of observing the cytosolic localization of cytotransmab TMab4 or HuT4 by confocal microscopy.

Specifically, HeLa cells were prepared in the same manner as described above. The prepared cells were incubated with 5 μM of PBS, TMab4, Adalimumab or HuT4 in serum-free medium at 37° C. for 4 hours. After 4 hours, each well containing PBS or the antibody was treated with 50 μM of calcein and incubated at 37° C. for 2 hours. After washing with PBS, the cells were fixed in the same manner as described above and were observed with a confocal microscope. As a result, it was shown that TMab4 and HuT4 showed the green fluorescence of calcein which escaped from the endosome into the cytosol. However, Adalimumab showed no green fluorescence in the cytosol.

Figure 11B:
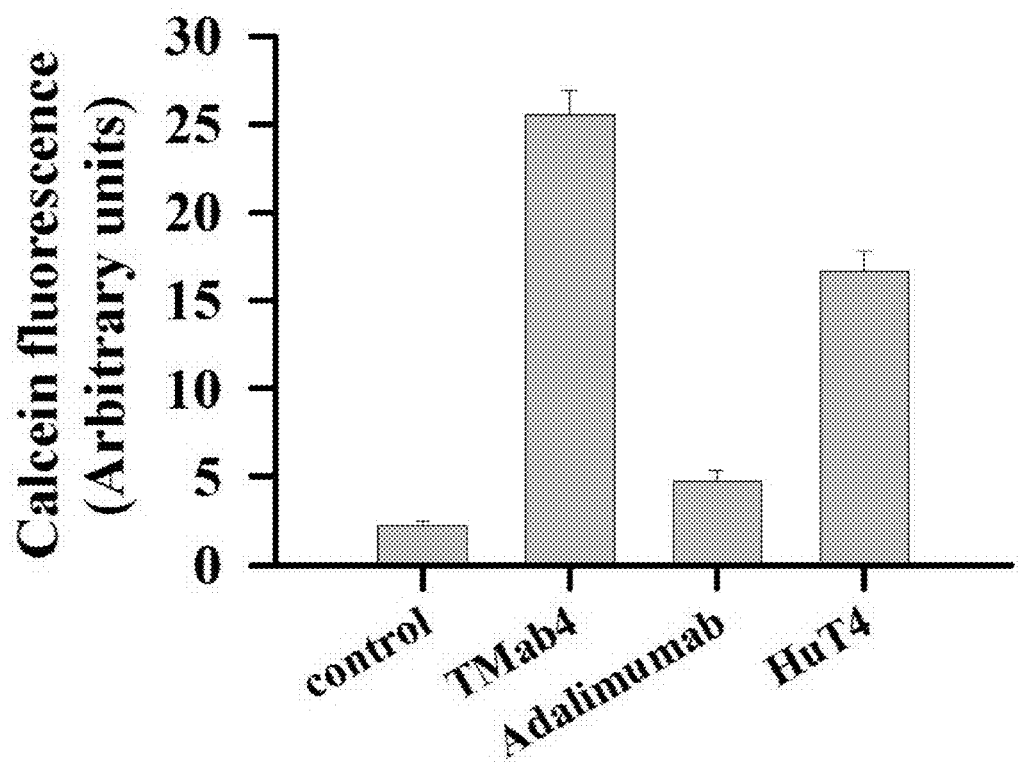
FIG. 11B is a bar graph showing the results of quantifying the calcein fluorescence of the confocal microscope images shown in FIG. 11A.

FIG. 11B is a bar graph showing the results of quantifying the calcein fluorescence of the confocal microscope images shown in FIG. 11A.

Specifically, using Image J software (National Institutes of Health, USA), 15 cells were selected in each condition, and then the obtained mean values of fluorescence are graphically shown.

Figure 12A:
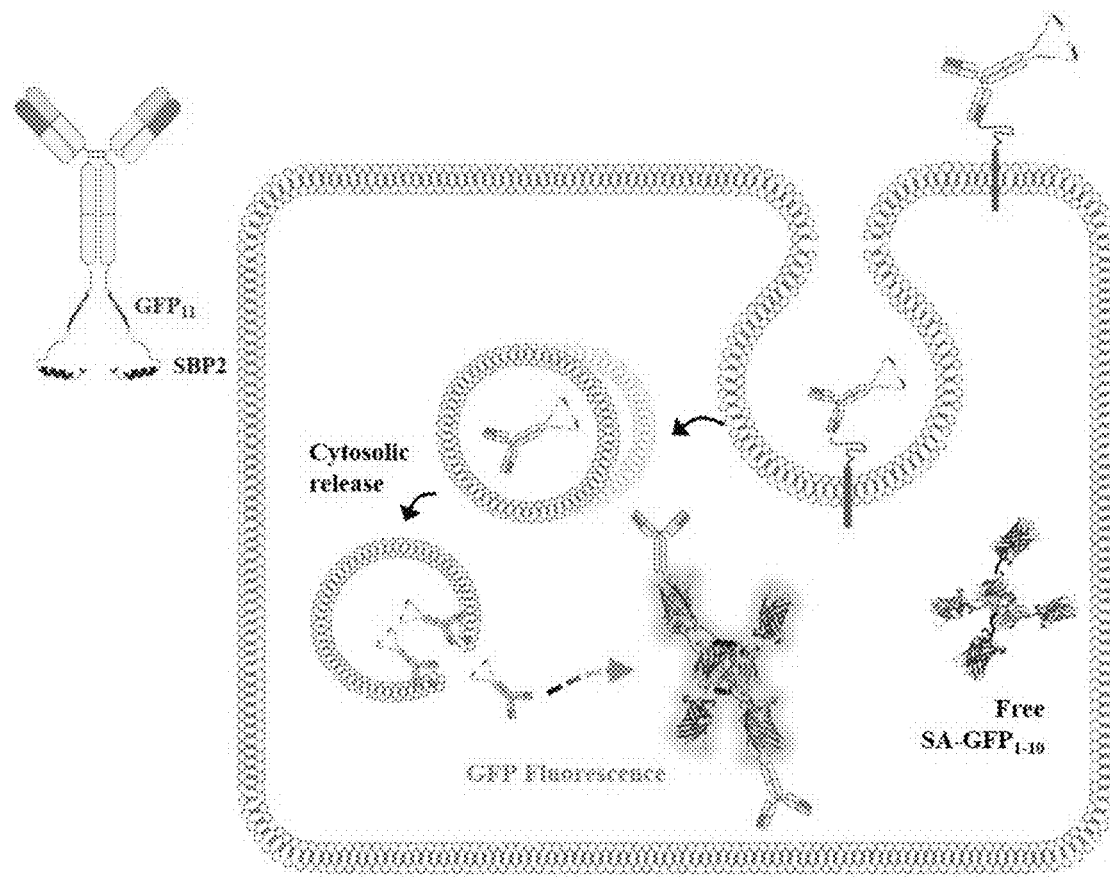
FIG. 12A is a schematic view showing a process in which GFP fluorescence by complementary association of split-GFP is observed when cytotransmab localizes in the cytosol.

Example 10: Examination of Cytosolic Retention of Cytotransmab by Recombination of GFP Fragments FIG. 12A is a schematic view showing a process in which GFP fluorescence by complementary association of split-GFP is observed when cytotransmab localizes in the cytosol.

Specifically, to directly confirm that cytotransmab localizes in the cytosol, a split-GFP system was used. If the green fluorescence protein GFP is split into two fragments (GFP 1-10 and GFP 11), the fluorescence property will be removed, and if the distance between the two fragments becomes closer so that they bind to each other, the florescence property can be restored (Cabantous et al., 2005). Based on such characteristics, the GFP 1-10 fragment is expressed in the cytosol, and the GFP 11 fragment is fused to the C-terminus of the heavy chain of Cytotransmab. Thus, the observation of GFP fluorescence indicates that Cytotransmab localizes in the cytosol.

In addition, in order to assist in the complementary association of split GFP, streptavidin-SBP2 (streptavidin binding peptide 2) with a higher affinity was used (Barrette-Ng et al., 2013). SBP2 with a smaller size was fused to the C-terminus of the GFP 11 fragment via three GGGGS linkers by a genetic engineering method. Furthermore, streptavidin was fused to the N-terminus of the GFP 1-10 fragment via three GGGGS linkers by a genetic engineering method. To realize this system, a stable transgenic cell line expressing streptavidin-GFP1-10 was developed.

Specifically, a DNA encoding Streptavidin-GFP1-10 was cloned into the Lenti virus vector pLJM1 (Addgene) by SalI/EcoRI. In a cell culture dish, $3 \times 10^6$ HEK293T cells were added to 1 ml of 10% FBS-containing medium and cultured for 12 hours under the conditions of 5% $CO_2$ and 37° C. 40 μl of Lipofectamine 2000 (Invitrogen, USA) was added to 600 μl of Opti-MEM media (Gibco), and the constructed Lenti virus vector and a virus packaging vector (pMDL, pRSV, or pVSV-G (Addgene)) were carefully added thereto and incubated at room temperature for 20 minutes, and then added to the dish. In addition, 9 ml of antibiotic-free DMEM medium was added to the cells which were then cultured for 6 hours under the conditions of 37° C. and 5% $CO_2$, after which the medium was replaced with 10 ml of 10% FBS-containing DMEM medium, followed by culture for 72 hours. After 60 hours, $1 \times 10^5$ HeLa cells were added to 1 ml of 10% FBS-containing medium and cultured for 12 hours under the conditions of 37° C. and 5% $CO_2$. The medium transiently transfected with the Lenti virus vector was completely filtered, and the viral particles in the medium were added to the prepared cell culture dish containing HeLa cells. To measure antibiotic resistance, puromycin resistance gene was used as a selection marker.

Figure 12B:
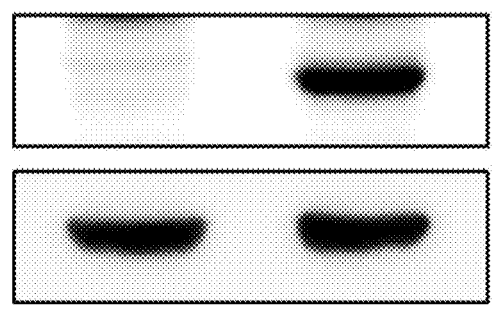
FIG. 12B shows the results of Western blot analysis performed to examine the expression level of streptavidin-GFP1-10 in a constructed stable cell line.

FIG. 12B shows the results of Western blot analysis performed to analyze the expression level of streptavidin-GFP1-10 in a constructed stable cell line.

Specifically, in a 6-well plate, $1 \times 10^5$ HeLa cells per well were added to 1 ml of 10% FBS-containing medium and cultured for 12 hours under the conditions of 37° C. and 5% $CO_2$. After culture, lysis buffer (10 mM Tris-HCl pH 7.4, 100 mM NaCl, 1% SDS, 1 mM EDTA, Inhibitor cocktail (sigma)) was added to the cells to obtain a cell lysate. The cell lysate was quantified using a BCA protein assay kit (Pierce). After SDS-PAGE, the gel was transferred to a PVDF membrane and incubated with antibodies (Santa Cruz) that recognize streptavidin and β-actin, respectively, at 25° C. for 2 hours, after which it was incubated with HRP-conjugated secondary antibody (Santa Cruz) at 25° C. for 1 hour, followed by detection. Analysis was performed using ImageQuant LAS4000 mini (GE Healthcare).

Example 11: Expression and Purification of GFP11-SBP2-Fused Cytotransmab

For expression of GFP11-SBP2-fused cytotransmab in animal cells, GFP11-SBP2 was fused to the C-terminus of the heavy chain via three GGGGS linkers. Next, an animal expression vector encoding the cytosol-penetrating light-chain and the cytosol-penetrating light-chain with improved endosomal escape and an animal expression vector expressing the GFP11-SBP2-fused heavy-chain were transiently co-transfected into HEK293F protein expression cells. Next, purification of the GFP11-SBP2-fused cytosol-penetrating monoclonal antibody was performed in the same manner as described in Example 5.

Figure 12C:
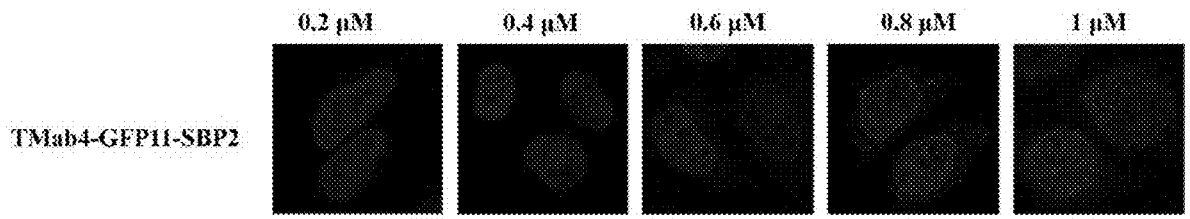
FIG. 12C shows the results of confocal microscopy observation of the GFP fluorescence of GFP11-SBP2-fused cytotransmab by complementary association of split GFP.

Example 12: Examination of GFP Fluorescence of GFP11-SBP2-Fused Cytotransmab by Cytosolic Localization FIG. 12C shows the results of confocal microscopy observation of the GFP fluorescence of GFP11-SBP2-fused cytotransmab by complementary association of split GFP.

Specifically, HeLa cells were prepared in the same manner as described in Example 7. When the cells were stabilized, these cells were cultured with 0.2, 0.4, 0.6, 0.8 and 1 μM of PBS or TMab4-GFP11-SBP2 at 37° C. for 6 hours. According to the same method as described in Example 7, the cells were washed with PBS and a weakly acidic solution, and then fixed. Furthermore, the nucleus was blue-stained with Hoechst33342 and observed with a confocal microscope. It was observed that TMab4 showed GFP fluorescence at 0.8 μM and 1 μM.

The above results clearly indicate that cytotransmab TMab4 penetrates cells and localizes in the cytosol.

Figure 13:
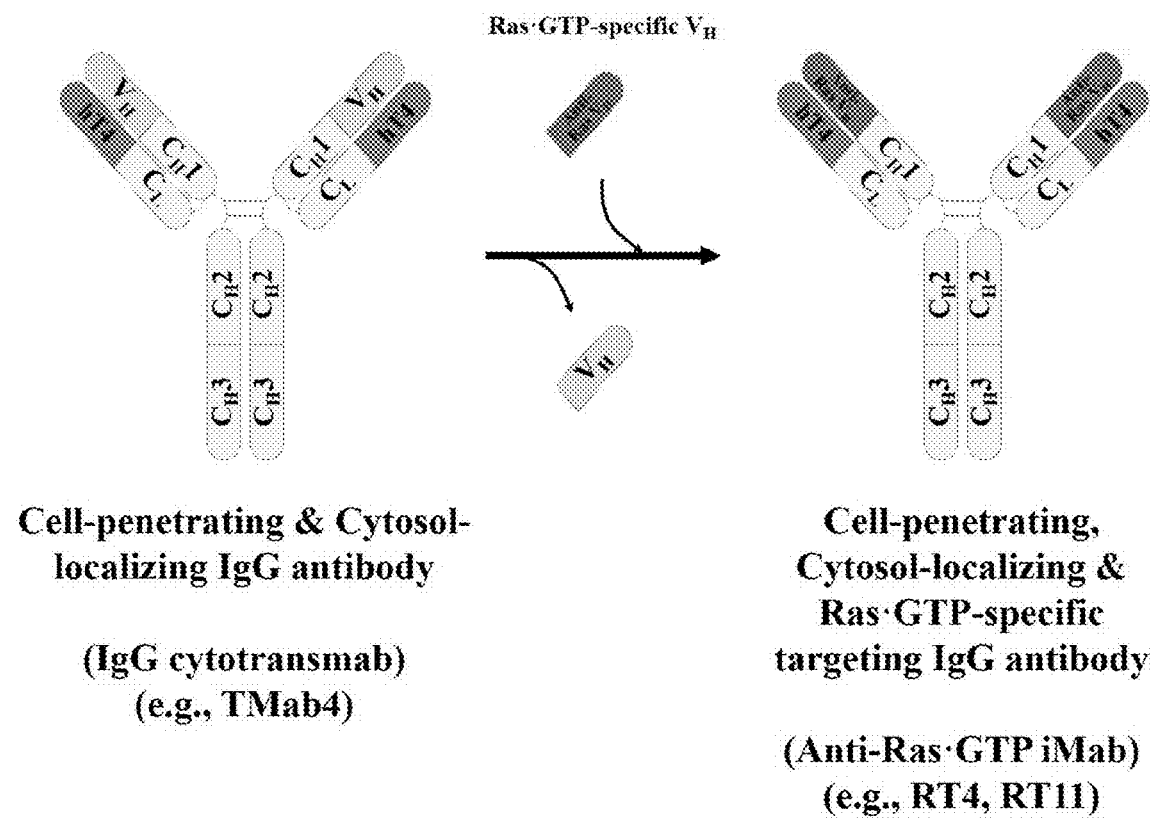
FIG. 13 is a schematic view showing a process of constructing anti-Ras•GTP iMab by replacing the heavy-chain variable region (VH) of an intact IgG-format Cytotransmab having only cytosol-penetrating ability with a heavy-chain variable region (VH) that binds specifically to GTP-bound KRas.

Example 13: Selection of Heavy-Chain Variable Region (VH), which Binds Specifically to GTP-Bound KRas, by High-Diversity Human VH Library FIG. 13 is a schematic view showing a process of constructing anti-Ras•GTP iMab by replacing the heavy-chain variable region (VH) of an intact IgG-format Cytotransmab having only cytosol-penetrating ability with a heavy-chain variable region (VH) that binds specifically to GTP-bound KRas.

Figure 14:
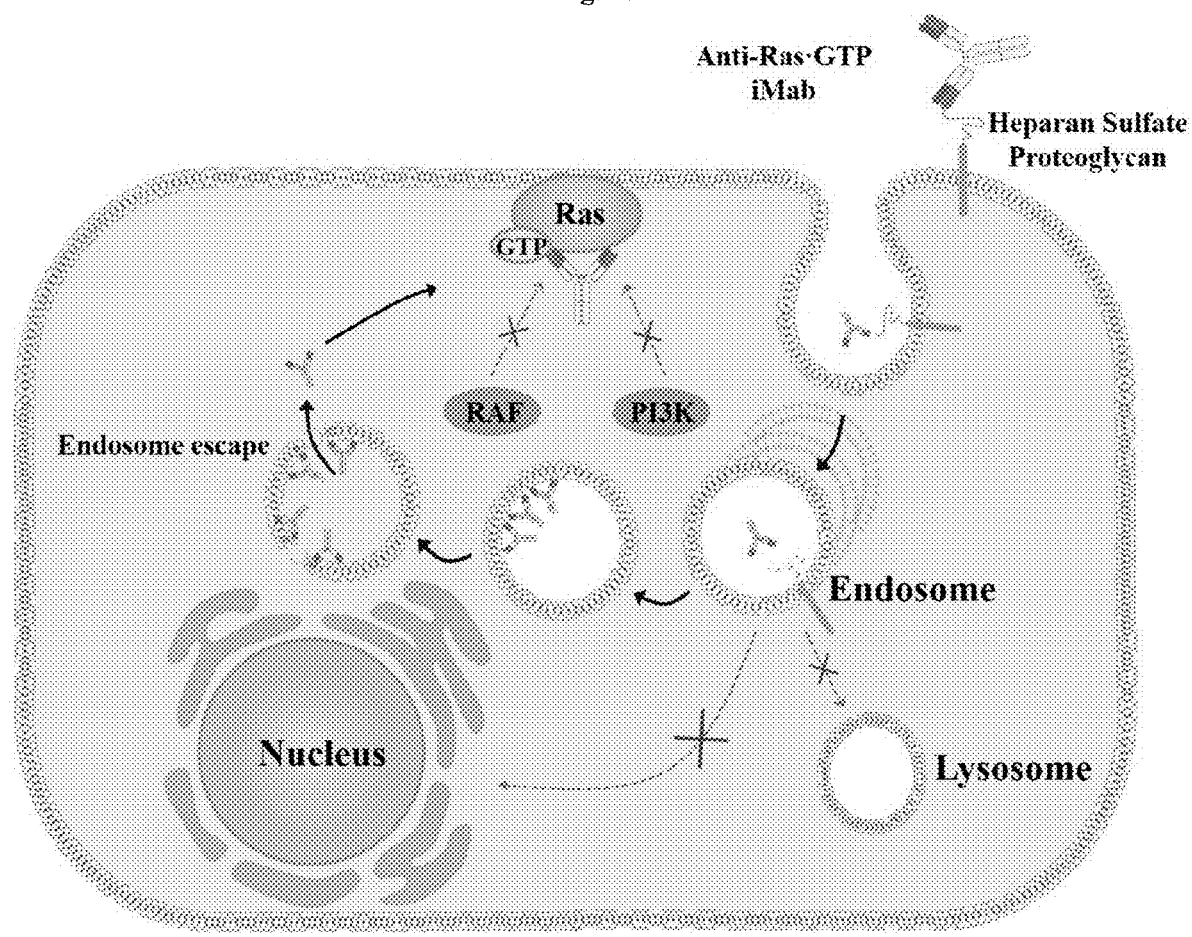
FIG. 14 shows the application of an IgG-format cytotransmab having only cytosol-penetrating ability, and is a schematic view showing a strategy of inducing cytotoxicity specific for Ras mutant cells by use of a monoclonal antibody (anti-Ras•GTP iMab: internalizing & interfering monoclonal antibody) which has a heavy-chain variable region (VH) replaced with a heavy-chain variable region (VH) binding specifically to GTP-bound KRas and which penetrates cells and binds specifically to GTP-bound Ras in the cells.

FIG. 14 shows the application of an IgG-format cytotransmab having only cytosol-penetrating ability, and is a schematic view showing a strategy of inducing cytotoxicity specific for Ras mutant cells by use of a monoclonal antibody (anti-Ras•GTP iMab: internalizing & interfering monoclonal antibody) which has a heavy-chain variable region (VH) replaced with a heavy-chain variable region (VH) binding specifically to GTP-bound KRas and which penetrates cells and binds specifically to GTP-bound Ras in the cells.

In order to select a stable humanized heavy-chain variable single domain (VH) which is to be introduced into the anti-Ras•GTP iMab and which binds specifically to GTP-bound KRas, a yeast expression VH library constructed through a previous study was used (Baek and Kim, 2014).

Specifically, the FR (framework) of the library used was the V gene IGHV3-23*04, $J_H4$ which is most commonly used in conventional antibodies, and the CDR3 in the library had 9 residues. The construction of the library and a yeast surface display method are described in detailed in a previously reported paper (Baek and Kim, 2014).

Example 14: Preparation of GTP-Bound KRas G12D Protein

Expression in *E. coli* and purification, performed to prepare GTP-bound KRas G12D antigen for library screening and affinity analysis, are described in detail in a previously reported paper (Tanaka T et al., 2007).

Specifically, a DNA encoding residues 1 to 188, which comprises the CAAX motif of each of wild-type KRas and mutant KRas G12D, KRas G12V and KRas G13D (listed in the order of higher to lower mutation frequency), was cloned into the *E. coli* expression vector pGEX-3X by use of the restriction enzymes BamHI/EcoRI. Herein, the expression vector was designed to have a T7 promoter-GST-KRas. All KRas mutations were induced using an overlap PCR technique, and the expression vector was constructed using the above-described method. The pGEX-3X-KRas vector was transformed into *E. coli* by electroporation, and selected in a selection medium. The selected *E. coli* was cultured in LB medium in the presence of 100 μg/ml of an ampicillin antibiotic at 37° C. until the absorbance at 600 nm reached 0.6. Then, 0.1 mM IPTG was added thereto for protein expression, and then the *E. coli* cells were further cultured at 30° C. for 5 hours. Thereafter, the *E. coli* cells were collected by centrifugation, and then disrupted by sonication (SONICS). The disrupted *E. coli* cells were removed by centrifugation, and the remaining supernatant was collected and purified using glutathione resin (Clontech) that specifically purifies GST-tagged protein. The glutathione resin was washed with 50 ml of washing buffer (140 mM NaCl, 2.7 mM KCl, 10 mM $NaH_2PO_4$, 1.8 mM $KH_2PO_4$, 1 mM EDTA, 2 mM $MgCl_2$ pH 7.4) (SIGMA), and then protein was eluted with elution buffer (50 mM Tris-HCl pH8.0, 10 mM reduced glutathione, 1 mM DTT, 2 mM $MgCl_2$) (SIGMA). The eluted protein was dialyzed to replace the buffer with storage buffer (50 mM Tris-HCl pH8.0, 1 mM DTT, 2 mM $MgCl_2$) (SIGMA). The purified protein was quantified by measuring the absorbance at a wavelength of 280 nm and the absorption coefficient. SDS-PAGE analysis indicated that the protein had a purity of about 98% or higher.

Next, in order to bind a GTPλS (Millipore) or GDP (Millipore) substrate to KRas protein, KRas and a substrate at a molecular ratio of 1:20 were reacted in a reaction buffer (50 mM Tris-HCl pH8.0, 1 mM DTT, 5 mM $MgCl_2$, 15 mM EDTA) (SIGMA) at 30° C. for 30 minutes, and 60 mM $MgCl_2$ was added thereto to stop the reaction, and then stored at −80° C.

Figure 15:
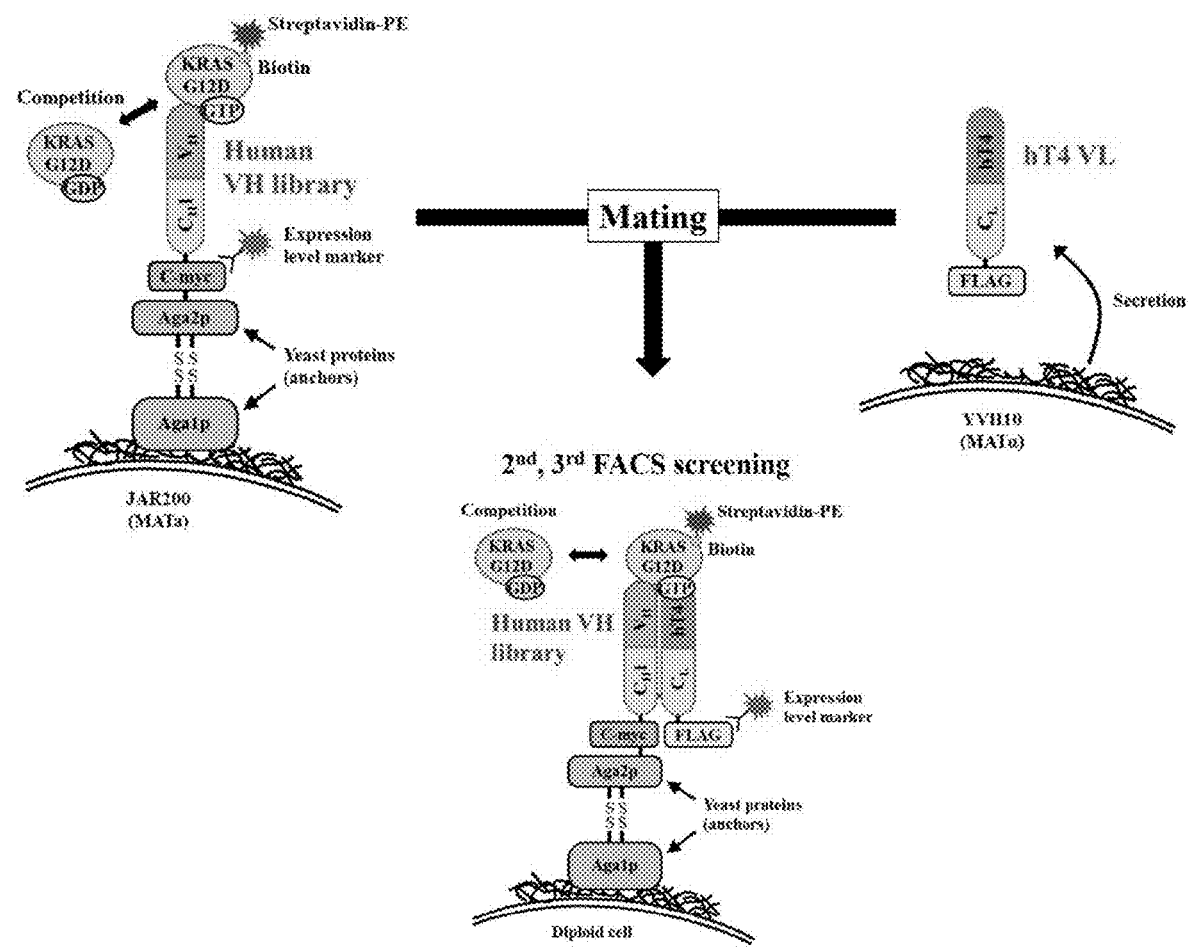
FIG. 15 is a schematic view showing a library screening strategy for obtaining a humanized antibody heavy-chain variable single domain having a high affinity only for GTP-bound KRas G12D protein.

Example 15: Selection of Heavy-Chain Variable Region (VH) Specific for GTP-Bound KRas G12D FIG. 15 is a schematic view showing a library screening strategy for obtaining a humanized antibody heavy-chain variable single domain having a high affinity only for GTP-bound KRas G12D protein.

Specifically, GTP-bound KRas G12D purified in Example 14 was biotinylated (EZ-LINK™ Sulfo-NHS-LC-Biotinylation kit (Pierce Inc., USA)), and then reacted with a heavy-chain variable region library displayed on the yeast cell surface at room temperature for 1 hour. The heavy-chain variable region library on the yeast cell surface, which reacted with the biotinylated GTP-bound KRas G12D, was reacted with Streptavidin (Microbead™ (Miltenyi Biotec) at 4° C. for 20 minutes, and then yeast displaying a heavy-chain variable region having a high affinity for the GTP-KRAS G12D was enriched using MACS (magnetic activated cell sorting). The selected library-displaying yeast was cultured in a selection medium and cultured in SG-CAA+URA (20 g/L Galactose, 6.7 g/L Yeast nitrogen base without amino acids, 5.4 g/L Na2HPO$_4$, 8.6 g/L NaH$_2$PO$_4$, 5 g/L casamino acids, 0.2 mg/L Uracil) (SIGMA) medium to induce protein expression. Next, the yeast was incubated with a yeast displaying the library competitively with GTP-bound KRas G12D alone or non-biotinylated GTP-bound KRas G12D antigen at a concentration 10-fold higher than GTP-bound KRas G12D, at room temperature for 1 hour, after which it was reacted with PE-conjugated Streptavidin (Streptavidin-R-phycoerythrin conjugate (SA-PE) (Invitrogen), and enriched by FACS (fluorescence activated cell sorting) (FACS Caliber) (BD biosciences). After selection of screening conditions by FACS analysis, antigen was bound to the yeast displaying the enriched library under the same conditions as described, and then the yeast was enriched using a FACS aria II sorter. The humanized heavy-chain region library enriched by the first MACS and first FACS screening was mated with a yeast secreting the cytosol-penetrating light-chain variable single domain (hT4 VL), and displayed on the yeast surface in the form of Fab, and then subjected to second FACS and third FACS screening.

Specifically, in order to construct a yeast which is to be mated with the heavy-chain variable domain (VH) library and which secretes the cytosol-penetrating light-chain variable domain (VL), a DNA encoding the cytosol-penetrating hT4 VL was cloned into the light-chain variable domain yeast secretion vector pYDS-K by the restriction enzymes NheI and BsiWI, thereby obtaining pYDS-K-hT4 VL. The obtained pYDS-K-hT4 VL was transformed into the mating α-type yeast mating strain YVH10 by electroporation, and mated with a yeast cultured in the selection medium SD-CAA+Trp (20 g/L Glucose, 6.7 g/L Yeast nitrogen base without amino acids, 5.4 g/L Na2HPO$_4$, 8.6 g/L NaH$_2$PO$_4$, 5 g/L casamino acids, 0.4 mg/L tryptophan) (SIGMA).

Specifically, in the case of yeast mating, there are $1 \times 10^7$ yeast cells when the absorbance at 600 nm is 1. Among the cultured yeast cells, $1.5 \times 10^7$ yeast cells expressing the selected heavy-chain variable domain library and $1.5 \times 10^7$ yeast cells containing hT4 VL were added to GTP-bound KRas G12D, and washed three times with YPD YPD (20 g/L Dextrose, 20 g/L peptone, 10 g/L yeast extract, 14.7 g/L sodium citrate, 4.29 g/L citric acid, pH 4.5) (SIGMA). Then, the yeast cells were re-suspended in 100 µl of YPD, and dropped onto an YPD plate so as not to spread, after which these yeast cells were dried and cultured at 30° C. for 6 hours. Next, the dried yeast-coated portion was washed three times with YPD medium, and then incubated in the selection medium SD-CAA at 30° C. for 24 hours to a final yeast concentration of $1 \times 10^6$ cells or less, and only mated yeast cells were selected. The selected yeast cells were incubated in SG-CAA medium to induce expression of a humanized antibody Fab fragment, and enriched by second and third FACS such that the yeast cells would be 100-fold competitive with GDP-bound KRas G12D at a GTP-bound KRas G12D concentration of 100 nM.

Figure 16:
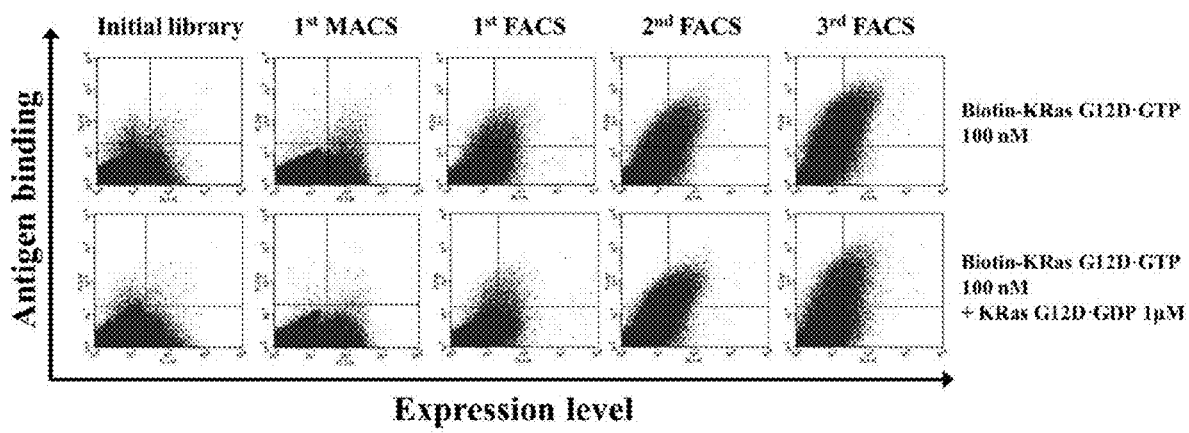
FIG. 16 shows the results of FACS analysis of binding under a condition of GTP-bound KRas G12D alone and a condition competitive with GTP-bound KRas G12D in each step of the above-described process for obtaining a high affinity for GTP-bound KRas G12D.

FIG. 16 shows the results of FACS analysis of binding under a condition of GTP-bound KRas G12D alone and a condition competitive with GTP-bound KRas G12D in each step of the above-described screening process for obtaining a high affinity for GTP-bound KRas G12D. Accordingly, it was found that it is possible to select a library that can bind specifically to GTP-bound KRas G12D in a manner dependent on the heavy-chain variable domain (VH).

Through the high-throughput screening as described above, an RT4 clone was finally selected from the library having a high affinity and specificity for GTP-bound KRas G12D protein by individual clone analysis.

Tables 4 and 5 below show the sequence information and SEQ ID NO of the heavy-chain variable domain RT4 that binds to activated RAS. Table 4 shows the full-length sequence of RT4, numbered according to the Kabat numbering system, and Table 5 shows the CDR sequence of the antibody sequence shown in Table 4.

TABLE 4

| Full-length sequence of heavy-chain variable domain RT4 that binds to activated RAS | | |
| --- | --- | --- |
| Names of heavy chain variable regions | Sequence | SEQ ID NO: |
| RT4 | 10        20        30        40        50 A<br>EVQLVESGGGLVQPGGSLRLSCAASGTFSSYAMSWVRQAPGKGLEWVSTISRSGHSTY<br>60        70        80 abc      90       a100      110<br>YADSVKGRFTISRDNSKNTLYLQMNSLRAEDTAVYYCAKRFGSIVFDYWGQGTLVT-<br>VSS | 13 |

TABLE 5

| CDR sequence of heavy-chain variable domain RT4 that binds to activated RAS | | | | | | | | | | | | | | | | |
| --- | --- | --- | --- | --- | --- | --- | --- | --- | --- | --- | --- | --- | --- | --- | --- | --- |
| Names of light chain variables regions | CDR1 Sequence | | | | | SEQ ID NO: | CDR2 Sequence | | | | | | | | | |
| Kabat No. | 32 | 32 | 33 | 34 | 35 | | 50 | 51 | 52 | 52a | 53 | 54 | 55 | 56 | 57 | 58 | 59 |
| RT4 | S | Y | A | M | S | 14 | T | I | S | R | S | G | H | S | T | Y | Y |

TABLE 5-continued

CDR sequence of heavy-chain variable domain RT4 that binds to activated RAS

| Names of light chain variables regions | CDR2 Sequence | | | | | | SEQ ID NO: | CDR3 Sequence | | | | | | | SEQ ID NO: |
|---|---|---|---|---|---|---|---|---|---|---|---|---|---|---|---|
| Kabat No. | 60 | 61 | 62 | 63 | 64 | 65 | | 95 | 96 | 97 | 98 | 99 | 100 | 100a | 101 | 102 | |
| RT4 | A | D | S | V | K | G | 15 | R | F | G | S | I | V | F | D | Y | 16 |

Example 16: Expression and Purification of Anti-Ras•GTP iMab, and Analysis of Affinity for KRas Mutations In order to express, in animal cells, anti-Ras•GTP iMab that can penetrate cells and specifically target GTP-bound Ras in the cells as a result of replacing the heavy-chain variable region (VH) of cell-penetrating and cytosol-localizing cytotransmab with RT4 VH selected in Example 13, as described in Example 5 above, a DNA, which has a secretion peptide-encoding DNA fused to the 5' end and comprises an RT4 heavy-chain variable region that binds specifically to GTP-bound KRas and a heavy-chain constant region (CH1-hinge-CH2-CH3), was cloned into a pcDNA3.4 vector (Invitrogen) by NotI/HindIII. Next, an animal expression vector encoding the cytosol-penetrating light-chain, and the constructed animal expression vector encoding a heavy chain comprising a heavy-chain variable region that binds specifically to GTP-bound KRas, were transiently co-transfected into protein-expressing HEK293F cells. Next, purification of anti-Ras•GTP iMab was performed in the same manner as described in Example 5.

Figure 17:
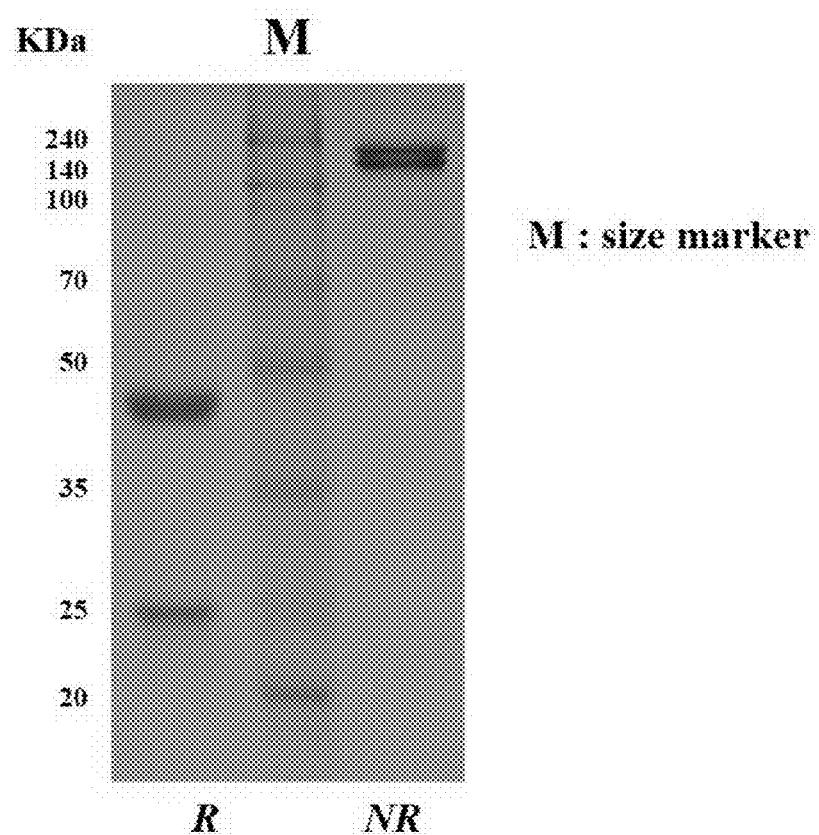
FIG. 17 shows the results of analyzing anti-Ras•GTP iMab RT4 by 12% SDS-PAGE under reductive or non-reductive conditions after purification.

FIG. 17 shows the results of analyzing anti-Ras•GTP iMab RT4 by 12% SDS-PAGE under reductive or non-reductive conditions after purification.

Specifically, in a non-reductive condition, a molecular weight of about 150 kDa appeared, and in a reductive condition, a heavy-chain molecular weight of about 50 kDa and a light-chain molecular weight of about 25 kDa appeared. This indicates that the expressed and purified anti-Ras•GTP iMab is present as a monomer in a solution state free of a non-covalent bond, and does not form a dimer or an oligomer by a non-natural disulfide bond.

Figure 18:
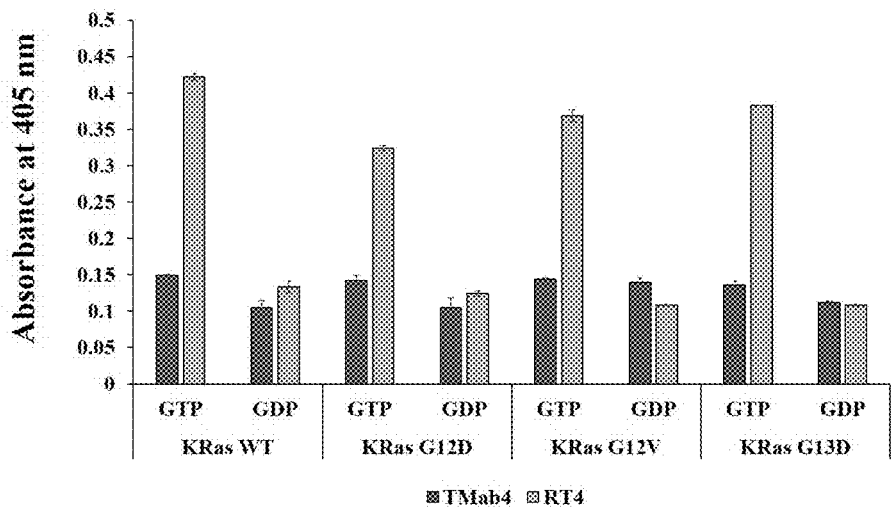
FIG. 18 shows the results of ELISA performed to measure affinity for GTP-bound and GDP-bound wild-type KRas and GTP-bound and GDP-bound KRas mutants (KRas G12D, KRas G12V, and KRas G13D).

FIG. 18 shows the results of ELISA performed to measure affinity for GTP-bound and GDP-bound wild-type KRas and GTP-bound and GDP-bound KRas mutants (KRas G12D, KRas G12V, and KRas G13D).

Specifically, each of GTP-bound KRas mutants and GDP-bound KRas mutants, which are target molecules, was incubated in a 96-well EIA/RIA plate (COSTAR Corning) at 37° C. for 1 hour, and then the plate was washed three times with 0.1% TBST (0.1% Tween20, pH 7.4, 137 mM NaCl, 12 mM Tris, 2.7 mM KCl, 5 mM $MgCl_2$) (SIGMA) for 10 minutes. Next, each well of the plate was incubated with 4% TBSB (4% BSA, pH7.4, 137 mM NaCl, 12 mM Tris, 2.7 mM KCl, 10 mM $MgCl_2$) (SIGMA) for 1 hour, and then washed three times with 0.1% TBST for 10 minutes. Thereafter, each well was incubated with anti-Ras•GTP iMab RT4 (and cytotransmab TMab4 having cytosol-penetrating ability only without Ras-binding ability) diluted in 4% TBSB at various concentrations, after which each well was washed three times with 0.1% PBST for 10 minutes. As a marker antibody, goat alkaline phosphatase-conjugated anti-human mAb (SIGMA) was used. Each well was treated with pNPP (p-nitrophenyl palmitate) (SIGMA), and the absorbance at 405 nm was measured.

In order to further quantitatively analyze the affinity of anti-Ras•GTP iMab RT4 for GTP-bound KRas G12D, SPR (Surface plasmon resonance) was performed using a Biacore 2000 instrument (GE healthcare).

Specifically, anti-Ras•GTP iMab RT4 was diluted in 10 mM Na-acetate buffer (pH 4.0), and immobilized on a CM5 sensor chip (GE Healthcare) at a concentration of about 1100 response units (RU). For analysis, Tris buffer (20 mM Tris-HCl, pH 8.0, 100 mM NaCl, 5 mM $MgCl_2$, 0.005% Tween 20) was flushed at a flow rate of 30 µl/min, and GTP-bound KRas G12D was used at a concentration ranging from 1000 nM to 62.5 nM. After analysis of association and dissociation, regeneration of the CM5 chip was performed by flushing a buffer (10 mM NaOH, 1M NaCl, pH10.0) at a flow rate of 30 µl/min for 1.5 minutes. Each of sensorgrams obtained at 3 min of association and 3 min of dissociation was normalized and subtracted from a blank cell, thereby determining affinity.

Figure 19:
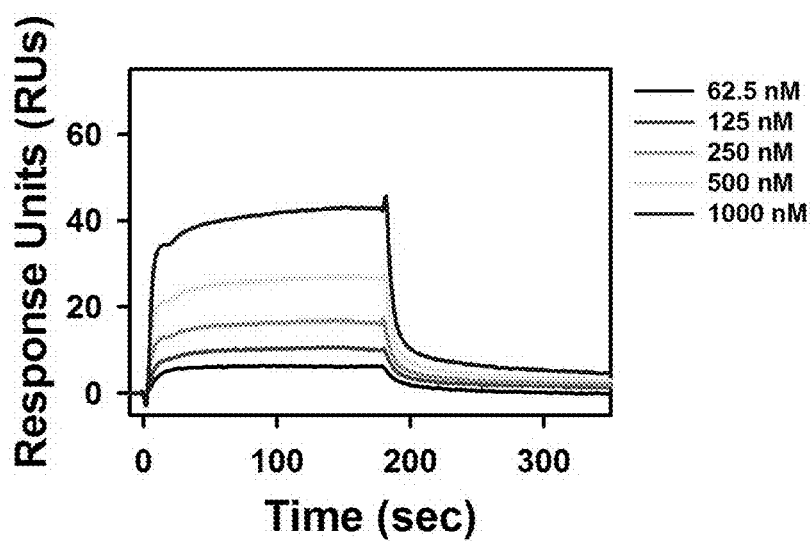
FIG. 19 shows the results of analyzing the affinity of anti-Ras•GTP iMab RT4 for GTP-bound KRAS G12D by use of SPR (BIACORE 2000) (GE healthcare).

FIG. 19 shows the results of analyzing the affinity of anti-Ras•GTP iMab RT4 for GTP-bound KRAS G12D by use of SPR (BIACORE 2000) (GE Healthcare).

Example 17: Examination of Cytosol-Penetrating Ability of Anti-Ras•GTP iMab RT4

Figure 20:
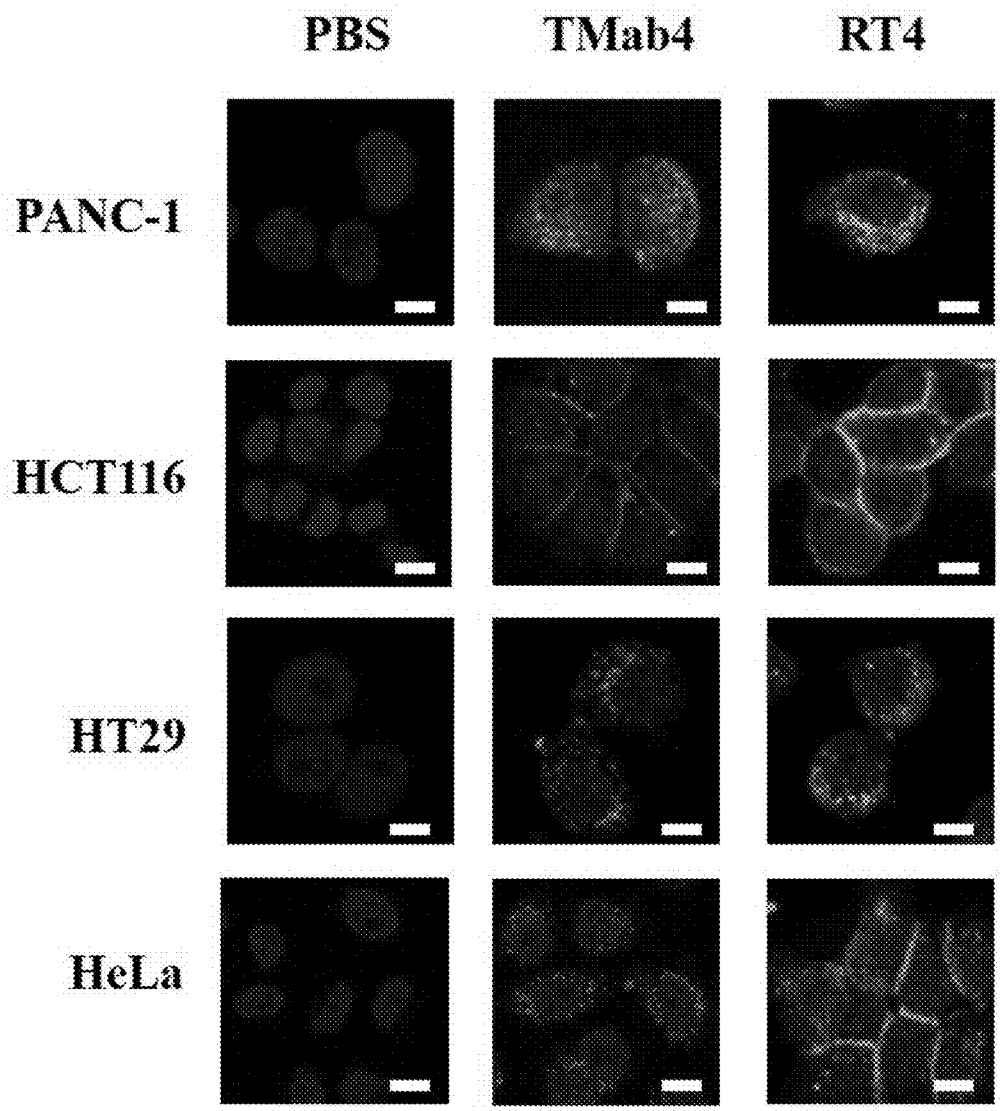
FIG. 20 shows the results of confocal microscopy observation performed to examine the cytosol-penetrating ability of anti-Ras•GTP iMab RT4.

FIG. 20 shows the results of confocal microscopy observation performed to examine the cytosol-penetrating ability of anti-Ras•GTP iMab RT4.

In cells lines (PANC-1, and HCT116) having mutant KRas and cell lines (HT29, HeLa) having wild-type KRas, the cell-penetrating ability of anti-Ras•GTP iMab RT4 was analyzed.

Specifically, each cell line was added to a 24-well plate at a density of $5 \times 10^4$ cells per well and cultured in 0.5 ml of 10% FBS-containing medium for 12 hours under the conditions of 5% $CO_2$ and 37° C. When the cells were stabilized, each of TMab4 and RT4, diluted in 0.5 ml of fresh medium at a concentration of 1 µM, was added to each well, followed by incubation for 6 hours under the conditions of 37° C. and 5% $CO_2$. A subsequent procedure was performed in the same manner as that of the staining procedure described in Example 7. It was observed that anti-Ras•GTP iMab showed fluorescence in the cells, indicating that cytotransmab did not lose its cytosol-penetrating ability, even after it was substituted with the heavy-chain variable region that binds specifically to GTP-bound KRas.

Example 18: Evaluation of Cytotoxicity of Anti-Ras•GTP iMab RT4

Figure 21:
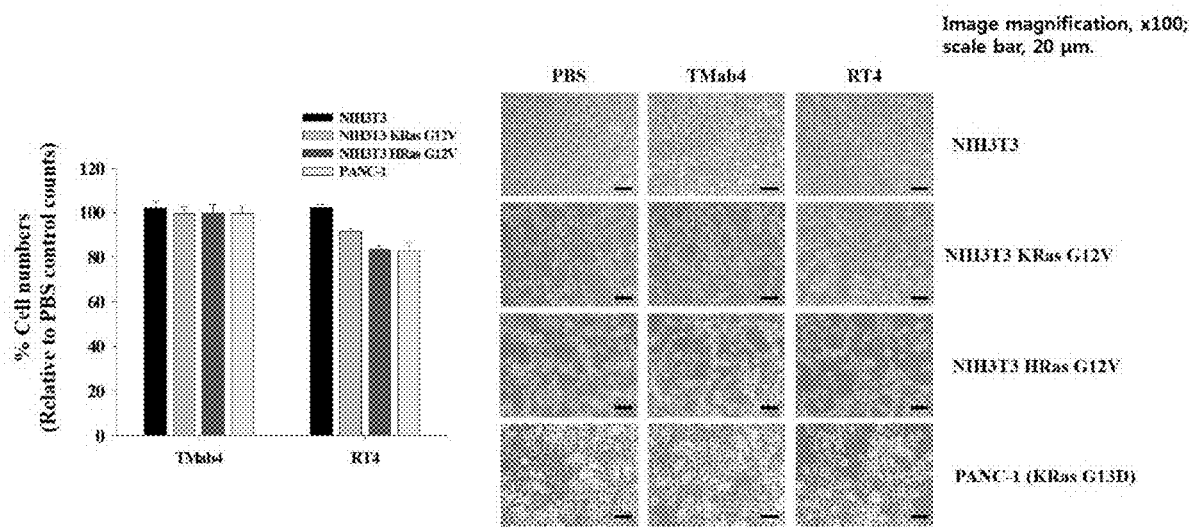
FIG. 21 shows the results obtained by treating NIH3T3, NIH3T3 KRas G12V and NIH3T3 HRas G12V cell lines with anti-Ras•GTP iMab RT4 and evaluating the inhibition of growth of the cells in vitro.

(1) Evaluation of the Effect of Anti-Ras•GTP iMab on Inhibition of Growth of Adherent Cells FIG. 21 shows the results obtained by treating NIH3T3, NIH3T3 KRas G12V and NIH3T3 HRas G12V cell lines with anti-Ras•GTP iMab RT4 and evaluating the inhibition of growth of the cells in vitro.

Specifically, in order to examine whether anti-Ras•GTP iMab has cytotoxicity specific for KRas mutant-dependent cells in vitro, wild-type KRas NIH3T3 mouse fibroblast cells, NIH3T3 KRas G12V cells having artificially overexpressed Ras mutant, NIH3T3 HRas G12V mutant cells, and KRas G13D mutant human pancreatic cells (PANC-1), were treated with 1 μM of each of TMab4 and RT4, and the inhibition of growth of adherent cells was evaluated.

Specifically, each type of NIH3T3 and PANC-1 cells was added to a 24-well plate at a density of $2 \times 10^3$ cells per well and cultured in 0.5 ml of 10% FBS-containing medium for 12 hours under the conditions of 37° C. and 5% $CO_2$. Next, the cells were treated twice with 1 μM of TMab4 or RT4 for 72 hours each time and observed for a total of 144 hours, and then the number of viable cells was counted, thereby determining the degree of growth of the cells.

As shown in FIG. 21, the cells treated with TMab4 showed no cytotoxicity, whereas RT4 inhibited the growth of the KRas mutant cell lines (NIH3T3 KRas G12V, and NIH3T3 HRas G12V), and the NIH3T3 cells showed no cytotoxicity. In addition, the growth of the KRas G13D mutant PANC-1 cells was inhibited. Thus, TMab4 had no cytotoxicity, whereas RT4 inhibited cell growth.

Figure 22:
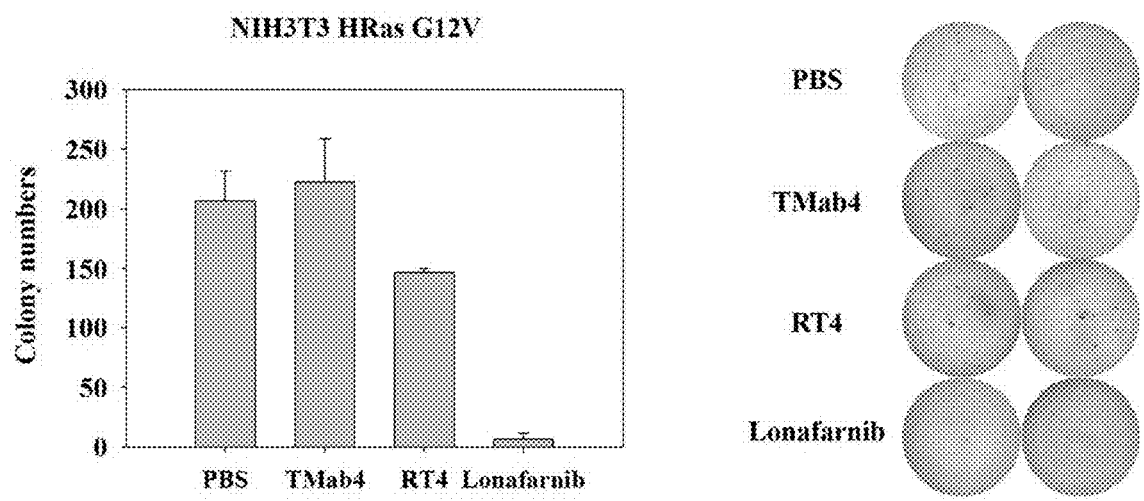
FIG. 22 shows the results of evaluating the inhibition of growth of non-adherent cells in an NIH3T3 HRas G12V cell line.

(2) Evaluation of the Effect of Anti-Ras•GTP iMab RT4 on Inhibition of Growth of Non-Adherent Cells FIG. 22 shows the results of evaluating the inhibition of growth of non-adherent cells in an NIH3T3 HRas G12V cell line.

Specifically, in order to examine whether anti-Ras•GTP iMab inhibits the growth of non-adherent cells in KRas mutant cells, NIH3T3 HRas G12V mutant cells were analyzed by a colony formation assay. Specifically, a mixture of 0.5 ml of 2×DMEM medium and 0.5 ml of 1% agrose solution was plated on a 12-well plate and hardened to form 0.5% gel. Then, 0.4 ml of 2×DMEM medium, 0.5 ml of 0.7% agarose, and 0.05 ml of $1 \times 10^3$ NIH3T3 HRas G12V cells were mixed with 0.05 ml (20 μM) of PBS, TMab4, RT4 or Lonafarnib (20 μM), and the mixture was plated on the 0.5% agarose gel and hardened. Thereafter, the 0.35% agarose gel was treated with a dispersion of 1 μM of PBS, TMab4, RT4 or Lonafarnib in 0.5 ml of 1×DMEM at 3-day intervals for a total of 21 days. On day 21, the cells were stained with NBT (nitro-blue tetrazolium) solution, and then the number of colonies was counted.

Similarly to the results of the above-described experiment on the inhibition of growth of adherent cells, RT4 inhibited colony formation, whereas TMab4 did not inhibit colony formation.

The above results indicate that anti-Ras•GTP iMab RT4 bind specifically to Ras mutants in the cytosol and inhibits the growth of adherent and non-adherent cells.

Figure 23:
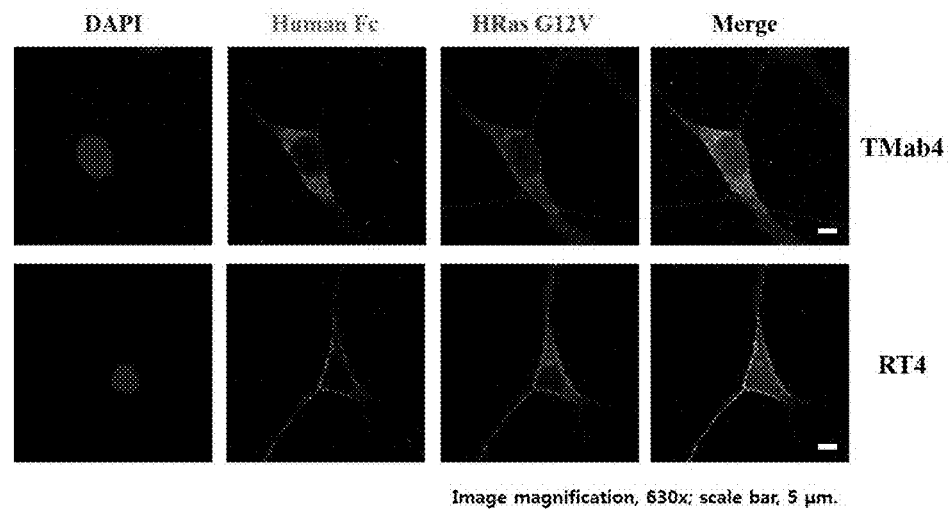
FIG. 23 shows the results of confocal microscopy observation of whether anti-Ras•GTP iMab RT4 is superimposed with activated HRas G12V mutants in cells.
Figure 24:
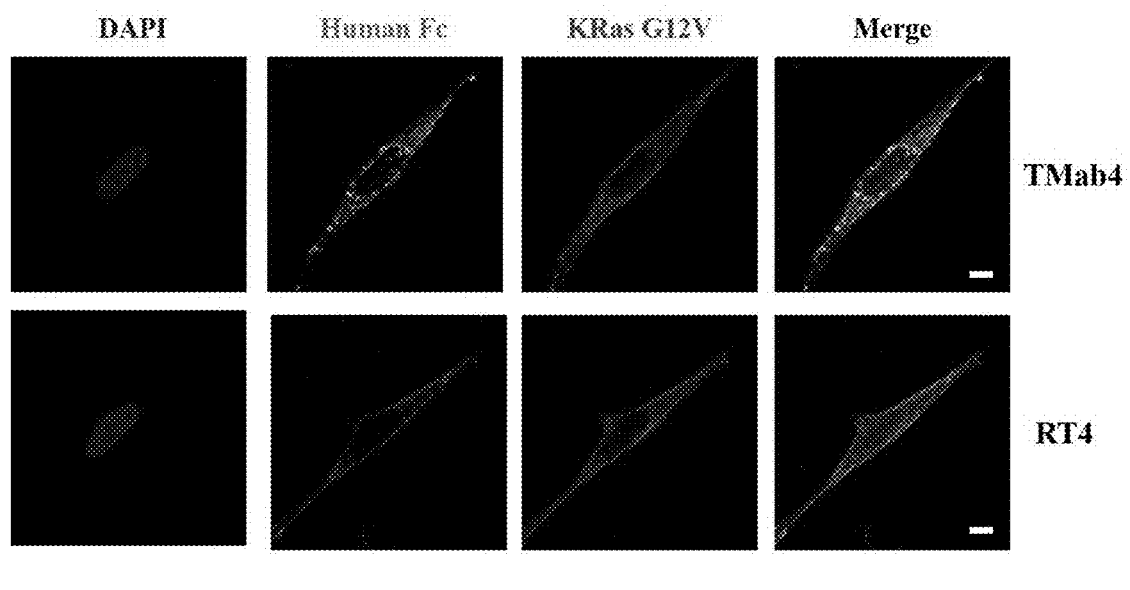
FIG. 24 shows the results of confocal microscopy observation of whether anti-Ras•GTP iMab RT4 is superimposed with GTP-bound KRas G12V mutants in cells.

Example 19: Examination of Whether Anti-Ras•GTP iMab RT4 Binds Specifically to GTP-Bound KRas in Cells FIG. 23 shows the results of whether anti-Ras•GTP iMab RT4 is superimposed with activated HRas G12V mutants in cells. FIG. 24 shows the results of confocal microscopy observation of whether anti-Ras•GTP iMab RT4 is superimposed with GTP-bound KRas G12V mutants in cells.

Specifically, 24-well plates were coated with fibronectin (Sigma), and then a dilution of 0.5 ml of NIH3T3 cells expressing mCherry (red fluorescence) HRas G12V or mCherry (red fluorescence) KRas G12V was added to the plate at a density of $2 \times 10^4$ cells per well, and cultured for 12 hours under the conditions of 37° C. and 5% $CO_2$. Next, the cells were treated with 2 μM of each of TMab4 and RT4 and cultured at 37° C. for 12 hours. Thereafter, the cells were stained under the same conditions as those described in Example 7, and were observed with a confocal microscope.

As shown in FIGS. 23 and 24, green fluorescent RT4 was superimposed with the cellular inner membrane in which red-fluorescent activated Ras was located, whereas TMab was not superimposed.

The above experimental results indicate that anti-Ras•GTP iMab RT4 bind specifically to GTP-bound Ras in the cells.

Example 20: Evaluation of Cytotoxicity of RGD-Fused Anti-Ras•GTP iMab RT4

For in vivo experiments, it is required to impart tumor tissue specificity. Conventional cytotransmabs bind to HSPG on the cell surface, and have no specificity for any other tumor tissue, and for this reason, cannot specifically inhibit the growth of tumors in in vivo experiments. To overcome this problem, an RGD4C peptide (CDCRGDCFC; SEQ ID NO: 17) having specificity for integrin αvβ3 which is overexpressed in angiogenetic cells and various tumors was fused to the N-terminus of the light chain via one GGGGS linker by a genetic engineering method. The RGD4C peptide is characterized in that it has affinity higher than conventional RGD peptides and can be fused using a genetic engineering method, and the specific structure thereof can be maintained even when it is fused to the N-terminus (Koivunen E et al., 1995).

Figure 25:
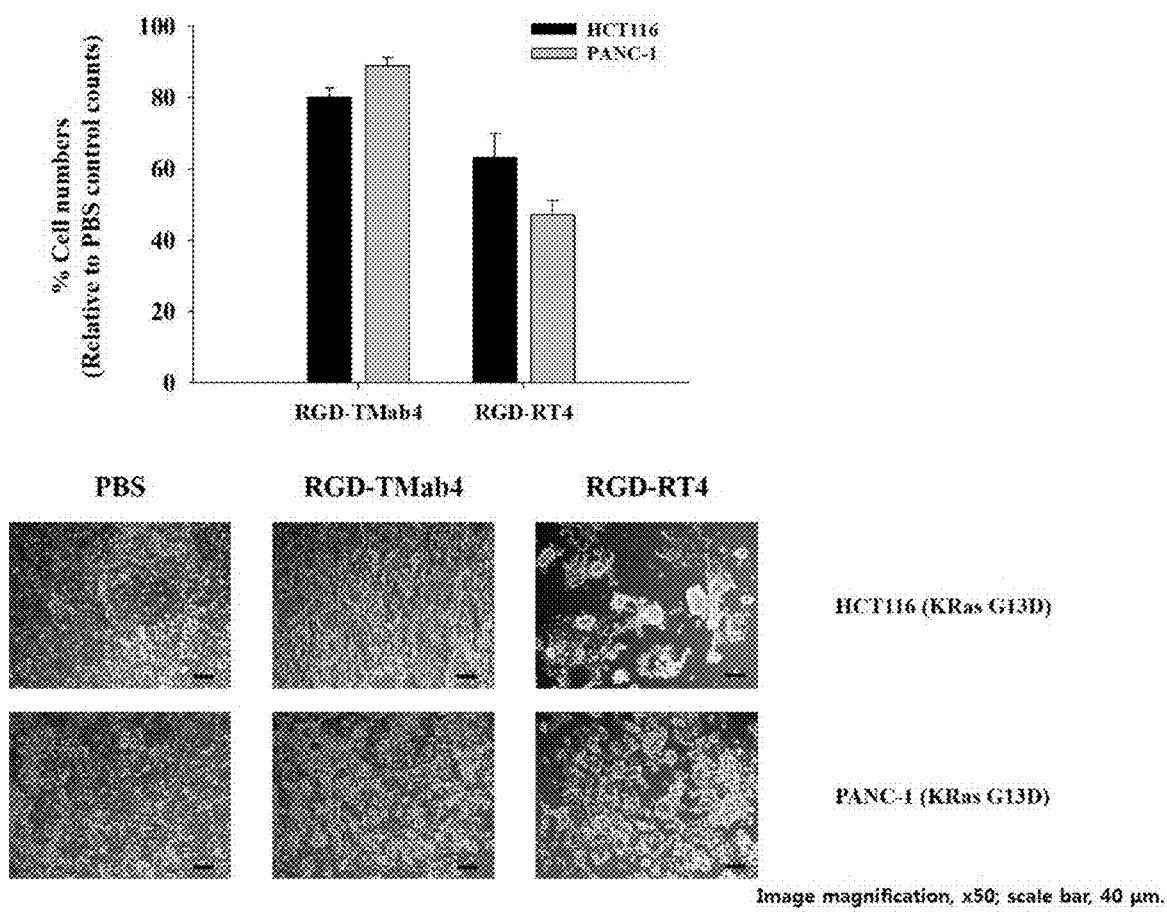
FIG. 25 shows the results obtained by treating HCT116 and PANC-1 cell lines with RGD-TMab4 and RGD-RT4 and evaluating the inhibition of growth of the cells in vitro.

FIG. 25 shows the results obtained by treating HCT116 and PANC-1 cell lines with RGD-TMab4 and RGD-RT4 and evaluating the inhibition of growth of the cells in vitro.

In order to examine whether RGD-TMab4 and RGD-RT4 themselves have cytotoxicity in vitro, human colorectal cancer HCT116 cells having a KRas G13D mutant, and human pancreatic cancer PANC-1 cells having a KRas G12D mutant, were treated with each of RGD-TMab4 and RGD-RT4, and the inhibition of growth of the cells was evaluated.

Specifically, each type of HCT116 and PANC-1 cells was added to a 24-well plate at a density of $5 \times 10^3$ cells per well, and cultured in 0.5 ml of 10% FBS-containing medium for 12 hours under the conditions of 37° C. and 5% $CO_2$. Next, the cells were treated twice with 1 μM of each of RGD-TMab4 and RGD-RT4 for 72 hours each time, and observed for a total of 144 hours, and then the number of the cells was counted, thereby determining the degree of growth of the cells.

As shown in FIG. 25, RGD-TMab4 inhibited the growth of HCT116 cells by about 20% and inhibited the growth of PANC-1 cells by about 15%, and RGD-RT4 inhibited the growth of HCT116 and PANC-1 cells by about 40% and about 50%, respectively. According to previous studies, the RGD4C peptide has an affinity for integrin αvβ5, which is about 3 times lower than that for integrin αvβ3. However, integrin αvβ3 is overexpressed mainly in angiogenetic cells, and integrin αvβ5 is expressed in various tumor cells. Thus, the RGD4C peptide has the ability to bind αvβ5 of HCT116 and PANC-1 cells to thereby inhibit cell adhesion (Cao L et al., 2008).

Thus, RGD4C peptide-fused TMab4 does not appear to have cytotoxicity. In addition, a comparison between RGD-TMab4 and RGD-RT4 indirectly confirmed that TMab4 can inhibit Ras-specific cell growth even when the RGD is fused thereto.

Figure 26A:
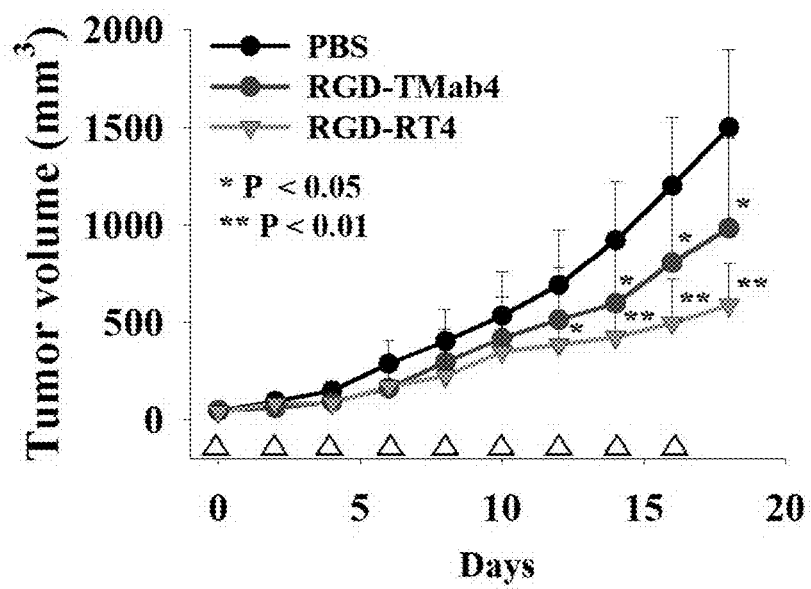
FIG. 26A shows the results of analyzing the tumor growth inhibitory effect of RGD-fused anti-Ras•GTP iMab RT4 in mice xenografted with HCT116 cells.
Figure 26B:
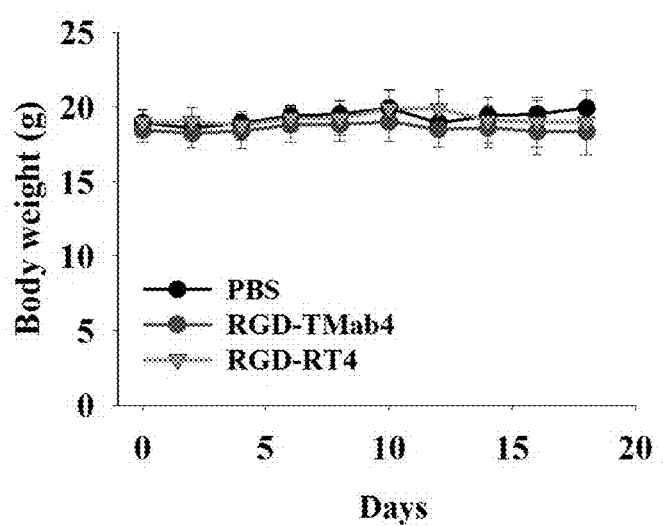
FIG. 26B is a graph showing the results of measuring the body weight of mice in order to examine the non-specific side effects of RGD-fused anti-Ras•GTP iMab RT4.

Example 21: Examination of the Effect of RGD-Fused Anti-Ras•GTP iMab on Inhibition of Tumor Growth FIG. 26A shows the results of analyzing the tumor growth inhibitory effect of RGD-fused anti-Ras•GTP iMab RT4 in mice xenografted with HCT116 cells. FIG. 26B is a graph showing the results of measuring the body weight of mice in order to examine the non-specific side effects of RGD-fused anti-Ras•GTP iMab RT4.

Specifically, in order to examine the tumor growth inhibitory effect of RGD-RT4 in vivo based on the in vitro experiment results of Example 20, KRas G13D mutant human colorectal HCT116 cells were injected subcutaneously into Balb/c nude mice at a density of $5 \times 10^6$ cells per mice. After about 6 days when the tumor volume reached about 50 mm$^3$, the mice were injected intravenously with 20 mg/kg of each of PBS, RGD-TMab4 and RGD-RT4. The injection was performed a total of 9 times at 2-day intervals, and the tumor volume was measured using a caliper for 18 days.

As shown in FIG. 26A, unlike the control PBS, RGD-TMab4 and RGD-RT4 inhibited the growth of cancer cells, and RGD-RT4 more effectively inhibited tumor growth compared to RGD-TMab4. In addition, as shown in FIG. 26B, there was no change in the body weight of the test group treated with RGD-RT4, indicating that RGD-RT4 has no other toxicities.

The invention claimed is:

1. A method of localizing an intact immunoglobulin-type antibody in the cytosol of a cell displaying at its surface heparin sulfate proteoglycan comprising:

contacting the cell with an intact immunoglobulin-type antibody whereby said antibody penetrates the membrane of the cell and localizes in the cell's cytosol, wherein the antibody comprises a light-chain variable region (VL) comprising:

a CDR1 comprising the amino acid sequence as set forth in SEQ ID NO: 4;
a CDR2 comprising the amino acid sequence as set forth in SEQ ID NO: 5; and
a CDR3 comprising the amino acid sequence as set forth in SEQ ID NO: 6;

wherein the 2nd and 4th amino acids starting from the N-terminus of the light-chain variable region are substituted with leucine (L) and methionine (M), respectively;

wherein the antibody comprises a heavy-chain variable region (VH) that comprises:

a CDR1 comprising the amino acid sequence as set forth in SEQ ID No: 14:

a CDR2 comprising the amino acid sequence as set forth in SEQ ID NO: 15: and a CDR3 comprising the amino acid sequence as set forth in SEQ ID NO: 16, and wherein the antibody specifically binds to a GTP-bound RAS ("RAS-GTP") in the cytosol of the cell.

2. The method of claim 1, wherein the antibody penetrates the cell membrane by undergoing endocytosis and subsequently escapes an endosome.

3. The method of claim 1, wherein the 9th, 10th, 13$^{th}$, 15th, 17th, 19th, 21st, 22nd, 42nd, 45th, 58th, 60th, 79th and 85th amino acids starting from the N-terminus of the light-chain variable region (VL) are substituted with serine (S), serine (S), alanine (A), valine (V), aspartic acid (D), valine (V), isoleucine (I), threonine (T), lysine (K), lysine (K), valine (V), serine (S), glutamine (Q) and threonine (T), respectively (wherein the positions of the amino acids are numbered according to the Kabat numbering system).

4. The method of claim 1, wherein the light-chain variable region (VL) comprises an amino acid sequence as forth in SEQ ID NO: 1.

5. The method of claim 1, wherein the heavy chain variable region (VH) comprises the amino acid sequence as set forth in SEQ ID NO: 13.

6. An antibody comprising
(i) a light-chain variable region (VL) comprising:
a CDR1 comprising the amino acid sequence as set forth in SEQ ID NO: 4;
a CDR2 comprising the amino acid sequence as set forth in SEQ ID NO: 5; and
a CDR3 comprising the amino acid sequence as set forth in SEQ ID NO: 6:
and a leucine residue at position 2 and a methionine at position 4 (as determined by Kabat numbering); and
(ii) a heavy-chain variable region (VH) comprising:
a CDR1 comprising the amino acid sequence as set forth in SEQ ID NO: 14;
a CDR2 comprising the amino acid sequence as set forth in SEQ ID NO: 15; and
a CDR3 comprising the amino acid sequence as set forth in SEQ ID NO: 16,
wherein the antibody specifically binds RAS-GTP.

7. The light antibody of claim 6, wherein the antibody penetrates the cell membrane by undergoing endocytosis and subsequently escapes an endosome.

8. The antibody of claim 6, wherein the 9th, 10th, 13th, 15th, 17th, 19th, 21st, 22nd, 42nd, 45th, 58th, 60th, 79th and 85th amino acids starting from the N-terminus of the light-chain variable region (VL) are substituted with serine (S), serine (S), alanine (A), valine (V), aspartic acid (D), valine (V), isoleucine (I), threonine (T), lysine (K), lysine (K), valine (V), serine (S), glutamine (Q) and threonine (T), respectively, (wherein the positions of the amino acids are numbered according to the Kabat numbering system).

9. The antibody of claim 6, wherein the light-chain variable region comprises an amino acid sequence as set forth in SEQ ID NO: 1.

10. The antibody of claim 6, wherein the heavy chain variable region (VH) comprises the amino acid sequence as set forth in SEQ ID NO: 13.

11. A polynucleotide that encodes the light chain variable region of the antibody of claim 6.

12. A polynucleotide that encodes the antibody of claim 6.

* * * * *

```
                       SEQUENCE LISTING

<160> NUMBER OF SEQ ID NOS: 21

<210> SEQ ID NO 1
<211> LENGTH: 114
<212> TYPE: PRT
<213> ORGANISM: Artificial Sequence
<220> FEATURE:
<223> OTHER INFORMATION: hT2 VL

<400> SEQUENCE: 1

Asp Leu Val Met Thr Gln Ser Pro Ala Thr Leu Ser Leu Ser Pro Gly
1               5                   10                  15

Glu Arg Ala Thr Leu Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Lys Gln
                85                  90                  95

Ser Tyr Tyr His Met Tyr Thr Phe Gly Gln Gly Thr Lys Val Glu Ile
            100                 105                 110

Lys Arg

<210> SEQ ID NO 2
<211> LENGTH: 114
<212> TYPE: PRT
<213> ORGANISM: Artificial Sequence
<220> FEATURE:
<223> OTHER INFORMATION: hT3 VL

<400> SEQUENCE: 2

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
```

50                  55                  60
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Lys Gln
                 85                  90                  95

Ser Tyr Tyr His Met Tyr Thr Phe Gly Gln Gly Thr Lys Val Glu Ile
            100                 105                 110

Lys Arg

<210> SEQ ID NO 3
<211> LENGTH: 114
<212> TYPE: PRT
<213> ORGANISM: Artificial Sequence
<220> FEATURE:
<223> OTHER INFORMATION: hT4 VL

<400> SEQUENCE: 3

Asp Leu Val Met Thr Gln Ser Pro Ser Ser Leu Ser Ala Ser Val Gly
 1               5                  10                  15

Asp Arg Val Thr Ile Thr Cys Lys Ser Ser Gln Ser Leu Phe Asn Ser
                 20                  25                  30

Arg Thr Arg Lys Asn Tyr Leu Ala Trp Tyr Gln Gln Lys Pro Gly Lys
             35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Tyr His Met Tyr Thr Phe Gly Gln Gly Thr Lys Val Glu Ile
            100                 105                 110

Lys Arg

<210> SEQ ID NO 4
<211> LENGTH: 17
<212> TYPE: PRT
<213> ORGANISM: Artificial Sequence
<220> FEATURE:
<223> OTHER INFORMATION: hT2 VL CDR1

<400> SEQUENCE: 4

Lys Ser Ser Gln Ser Leu Phe Asn Ser Arg Thr Arg Lys Asn Tyr Leu
 1               5                  10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: hT2 VL CDR2

<400> SEQUENCE: 5

Trp Ala Ser Thr Arg Glu Ser
 1               5

<210> SEQ ID NO 6
<211> LENGTH: 9
<212> TYPE: PRT
<213> ORGANISM: Artificial Sequence

```
<220> FEATURE:
<223> OTHER INFORMATION: hT2 VL CDR3

<400> SEQUENCE: 6

Lys Gln Ser Tyr Tyr His Met Tyr Thr
1               5

<210> SEQ ID NO 7
<211> LENGTH: 17
<212> TYPE: PRT
<213> ORGANISM: Artificial Sequence
<220> FEATURE:
<223> OTHER INFORMATION: hT3 VL CDR1

<400> SEQUENCE: 7

Lys Ser Ser Gln Ser Leu Phe Asn Ser Arg Thr Arg Lys Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: hT3 VL CDR2

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: hT3 VL CDR3

<400> SEQUENCE: 9

Lys Gln Ser Tyr Tyr His Met Tyr Thr
1               5

<210> SEQ ID NO 10
<211> LENGTH: 17
<212> TYPE: PRT
<213> ORGANISM: Artificial Sequence
<220> FEATURE:
<223> OTHER INFORMATION: hT4 VL CDR1

<400> SEQUENCE: 10

Lys Ser Ser Gln Ser Leu Phe Asn Ser Arg Thr Arg Lys Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: hT4 VL CDR2

<400> SEQUENCE: 11

Trp Ala Ser Thr Arg Glu Ser
1               5

<210> SEQ ID NO 12
```

```
<211> LENGTH: 9
<212> TYPE: PRT
<213> ORGANISM: Artificial Sequence
<220> FEATURE:
<223> OTHER INFORMATION: hT4 VL CDR3

<400> SEQUENCE: 12

Gln Gln Tyr Tyr Tyr His Met Tyr Thr
1               5

<210> SEQ ID NO 13
<211> LENGTH: 118
<212> TYPE: PRT
<213> ORGANISM: Artificial Sequence
<220> FEATURE:
<223> OTHER INFORMATION: RT4

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly His Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Phe Gly Ser Ile Val Phe Asp Tyr Trp Gly Gln Gly Thr
            100                 105                 110

Leu Val Thr Val Ser Ser
        115

<210> SEQ ID NO 14
<211> LENGTH: 5
<212> TYPE: PRT
<213> ORGANISM: Artificial Sequence
<220> FEATURE:
<223> OTHER INFORMATION: RT4 CDR1

<400> SEQUENCE: 14

Ser Tyr Ala Met Ser
1               5

<210> SEQ ID NO 15
<211> LENGTH: 17
<212> TYPE: PRT
<213> ORGANISM: Artificial Sequence
<220> FEATURE:
<223> OTHER INFORMATION: RT4 CDR2

<400> SEQUENCE: 15

Thr Ile Ser Arg Ser Gly His Ser Thr Tyr Tyr Ala Asp Ser Val Lys
1               5                   10                  15

Gly

<210> SEQ ID NO 16
<211> LENGTH: 9
<212> TYPE: PRT
<213> ORGANISM: Artificial Sequence
<220> FEATURE:
```

<223> OTHER INFORMATION: RT4 CDR3

<400> SEQUENCE: 16

Arg Phe Gly Ser Ile Val Phe Asp Tyr
1               5

<210> SEQ ID NO 17
<211> LENGTH: 9
<212> TYPE: PRT
<213> ORGANISM: Artificial Sequence
<220> FEATURE:
<223> OTHER INFORMATION: RGD4C

<400> SEQUENCE: 17

Cys Asp Cys Arg Gly Asp Cys Phe Cys
1               5

<210> SEQ ID NO 18
<211> LENGTH: 113
<212> TYPE: PRT
<213> ORGANISM: Artificial Sequence
<220> FEATURE:
<223> OTHER INFORMATION: m3D8 VL

<400> SEQUENCE: 18

Asp Leu Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr His Met Tyr Thr Phe Gly Ser Gly Thr Lys Leu Glu Ile
            100                 105                 110

Lys

<210> SEQ ID NO 19
<211> LENGTH: 113
<212> TYPE: PRT
<213> ORGANISM: Artificial Sequence
<220> FEATURE:
<223> OTHER INFORMATION: hT0 VL

<400> SEQUENCE: 19

Asp Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Lys Gln

```
                          85                  90                  95
Ser Tyr Tyr His Met Tyr Thr Phe Gly Gln Gly Thr Lys Val Glu Ile
                100                 105                 110
Lys

<210> SEQ ID NO 20
<211> LENGTH: 107
<212> TYPE: PRT
<213> ORGANISM: Artificial Sequence
<220> FEATURE:
<223> OTHER INFORMATION: Adalimumab VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
                100                 105

<210> SEQ ID NO 21
<211> LENGTH: 107
<212> TYPE: PRT
<213> ORGANISM: Artificial Sequence
<220> FEATURE:
<223> OTHER INFORMATION: Bevacizumab VL

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
                100                 105
```